US008895311B1

(12) United States Patent
Handique et al.

(10) Patent No.: US 8,895,311 B1
(45) Date of Patent: Nov. 25, 2014

(54) METHODS AND SYSTEMS FOR CONTROL OF GENERAL PURPOSE MICROFLUIDIC DEVICES

(75) Inventors: Kalyan Handique, Ann Arbor, MI (US); Karthik Ganesan, Ann Arbor, MI (US); Sundaresh N. Brahmasandra, Ann Arbor, MI (US)

(73) Assignee: HandyLab, Inc., Franklin Lakes, NJ (US)

( * ) Notice: Subject to any disclaimer, the term of this patent is extended or adjusted under 35 U.S.C. 154(b) by 889 days.

(21) Appl. No.: 10/246,814

(22) Filed: Sep. 18, 2002

Related U.S. Application Data

(63) Continuation-in-part of application No. 09/819,105, filed on Mar. 28, 2001, now Pat. No. 7,010,391.

(51) Int. Cl.
*G01N 35/00* (2006.01)
(52) U.S. Cl.
USPC ............ 436/43; 422/67; 422/502; 422/504; 422/509; 702/22; 702/31
(58) Field of Classification Search
USPC ............ 422/67, 502, 504, 509; 436/43, 180; 702/22, 31
See application file for complete search history.

(56) References Cited

U.S. PATENT DOCUMENTS

| | | | |
|---|---|---|---|
| 1,434,314 A | 10/1922 | Raich | |
| 1,733,401 A | 8/1930 | Lovekin | |
| D189,404 S | 12/1960 | Nicolle | |
| 3,813,316 A | 5/1974 | Chakrabarty et al. | |
| 3,985,649 A | 10/1976 | Eddelman | |
| 4,018,089 A | 4/1977 | Dzula et al. | |
| 4,018,652 A | 4/1977 | Lanham et al. | |
| 4,038,192 A | 7/1977 | Serur | |

(Continued)

FOREIGN PATENT DOCUMENTS

| | | |
|---|---|---|
| CA | 2294819 | 1/1999 |
| DE | 19929734 | 12/1999 |

(Continued)

OTHER PUBLICATIONS

Bollet, C. et al., "A simple method for the isolation of chromosomal DNA from Gram positive or acid-fast bacteria", Nucleic Acids Research, vol. 19, No. 8 (1991), p. 1955.

(Continued)

*Primary Examiner* — Jan Ludlow
(74) *Attorney, Agent, or Firm* — Knobbe Martens Olson & Bear LLP

(57) ABSTRACT

The present invention provides control methods, control systems, and control software for microfluidic devices that operate by moving discrete micro-droplets through a sequence of determined configurations. Such microfluidic devices are preferably constructed in a hierarchical and modular fashion which is reflected in the preferred structure of the provided methods and systems. In particular, the methods are structured into low-level device component control functions, middle-level actuator control functions, and high-level micro-droplet control functions. Advantageously, a microfluidic device may thereby be instructed to perform an intended reaction or analysis by invoking micro-droplet control function that perform intuitive tasks like measuring, mixing, heating, and so forth. The systems are preferably programmable and capable of accommodating microfluidic devices controlled by low voltages and constructed in standardized configurations. Advantageously, a single control system can thereby control numerous different reactions in numerous different microfluidic devices simply by loading different easily understood micro-droplet programs.

28 Claims, 23 Drawing Sheets

(56) References Cited

U.S. PATENT DOCUMENTS

| | | |
|---|---|---|
| 4,055,395 A | 10/1977 | Honkawa et al. |
| D249,706 S | 9/1978 | Adamski |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Teraski et al. |
| 4,612,873 A | 9/1986 | Eberle |
| D288,478 S | 2/1987 | Carlson et al. |
| 4,647,432 A | 3/1987 | Wakatake |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,841,786 A | 6/1989 | Schulz |
| D302,294 S | 7/1989 | Hillman |
| 4,871,779 A | 10/1989 | Killat et al. |
| 4,895,650 A | 1/1990 | Wang |
| 4,919,892 A | 4/1990 | Plumb |
| 4,921,809 A | 5/1990 | Schiff et al. |
| 4,935,342 A | 6/1990 | Seligson et al. |
| D310,413 S | 9/1990 | Bigler et al. |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,048,554 A | 9/1991 | Kremer |
| 5,060,823 A | 10/1991 | Perlman |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| D328,135 S | 7/1992 | Fan et al. |
| D328,794 S | 8/1992 | Frenkel et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,223,226 A | 6/1993 | Wittmer et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,487 A | 4/1994 | Wilding et al. |
| D347,478 S | 5/1994 | Pinkney |
| 5,311,896 A | 5/1994 | Kaartinen |
| 5,311,996 A | 5/1994 | Duffy et al. |
| 5,316,727 A | 5/1994 | Suzuki et al. |
| 5,327,038 A | 7/1994 | Culp |
| D351,475 S | 10/1994 | Gerber |
| D351,913 S | 10/1994 | Hieb et al. |
| 5,364,591 A | 11/1994 | Green et al. |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,414,245 A | 5/1995 | Hackleman |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,516,410 A | 5/1996 | Schneider et al. |
| 5,529,677 A | 6/1996 | Schneider et al. |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |
| 5,582,884 A | 12/1996 | Ball et al. |
| 5,585,069 A | 12/1996 | Zanzucchi et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| D378,782 S | 4/1997 | LaBarbera et al. |
| 5,628,890 A | 5/1997 | Carter et al. |
| 5,630,920 A | 5/1997 | Friese et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,699,157 A | 12/1997 | Parce |
| 5,700,637 A | 12/1997 | Southern |
| 5,726,026 A | 3/1998 | Wilding et al. |
| 5,726,404 A | 3/1998 | Brody |
| 5,726,944 A | 3/1998 | Taft et al. |
| 5,744,366 A | 4/1998 | Kricka et al. |
| 5,747,666 A | 5/1998 | Willis |
| 5,755,942 A | 5/1998 | Zanzucchi et al. |
| 5,770,388 A | 6/1998 | Vorpahl |
| 5,779,868 A | 7/1998 | Parce et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |

(56) References Cited

U.S. PATENT DOCUMENTS

| | | |
|---|---|---|
| 5,858,187 A | 1/1999 | Ramsey et al. |
| 5,858,188 A | 1/1999 | Soane et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,623 A | 2/1999 | Stabile et al. |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,470 A | 3/1999 | Parce et al. |
| 5,900,130 A | 5/1999 | Benvegnu et al. |
| 5,912,124 A | 6/1999 | Kumar |
| 5,916,776 A | 6/1999 | Kumar |
| 5,919,646 A | 7/1999 | Okun et al. |
| 5,922,591 A | 7/1999 | Anderson et al. |
| 5,928,880 A | 7/1999 | Wilding et al. |
| 5,929,208 A | 7/1999 | Heller et al. |
| D413,391 S | 8/1999 | Lapeus et al. |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 6,001,229 A | 12/1999 | Ramsey |
| 6,001,231 A | 12/1999 | Kopf-Sill |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,156,199 A | 12/2000 | Zuk, Jr. |
| 6,158,269 A | 12/2000 | Dorenkott et al. |
| 6,167,910 B1 | 1/2001 | Chow |
| 6,171,850 B1 | 1/2001 | Nagle et al. |
| 6,180,950 B1 | 1/2001 | Olsen |
| D438,311 S | 2/2001 | Yamanishi et al. |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Lines et al. |
| 6,238,626 B1 | 5/2001 | Higuchi et al. |
| 6,254,826 B1 | 7/2001 | Acosta et al. |
| 6,259,635 B1 | 7/2001 | Torelli et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 * | 9/2001 | Becker et al. ................ 204/450 |
| 6,302,134 B1 | 10/2001 | Kellogg et al. |
| 6,302,304 B1 | 10/2001 | Spencer |
| 6,303,343 B1 | 10/2001 | Kopf-Sill |
| 6,306,273 B1 | 10/2001 | Wainright et al. |
| 6,306,590 B1 | 10/2001 | Mehta et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-Sill et al. |
| 6,366,924 B1 | 4/2002 | Parce |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Majer et al. |
| 6,401,552 B1 | 6/2002 | Elkins |
| 6,403,338 B1 | 6/2002 | Knapp et al. |

(56) References Cited

U.S. PATENT DOCUMENTS

| | | |
|---|---|---|
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | Mcreynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-Sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | Mcreynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| 6,750,661 B2 | 6/2004 | Brooks et al. |
| 6,752,966 B1 | 6/2004 | Chazan |
| 6,756,019 B1 | 6/2004 | Dubrow et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D500,142 S | 12/2004 | Crisanti et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,977,163 B1 | 12/2005 | Mehta |
| D516,221 S | 2/2006 | Wohlstadter et al. |
| 7,004,184 B2 | 2/2006 | Handique et al. |
| 7,010,391 B2 | 3/2006 | Handique et al. |
| 7,024,281 B1 | 4/2006 | Unno |
| 7,037,416 B2 | 5/2006 | Parce et al. |
| 7,040,144 B2 | 5/2006 | Spaid et al. |
| 7,049,558 B2 | 5/2006 | Baer et al. |
| 7,060,171 B1 | 6/2006 | Nikiforov et al. |
| 7,105,304 B1 | 9/2006 | Nikiforov et al. |
| 7,150,814 B1 | 12/2006 | Parce et al. |
| 7,150,999 B1 | 12/2006 | Shuck |
| 7,169,277 B2 | 1/2007 | Ausserer et al. |
| 7,169,618 B2 | 1/2007 | Skold |
| 7,192,557 B2 | 3/2007 | Wu et al. |
| 7,235,406 B1 | 6/2007 | Woudenberg et al. |
| 7,270,786 B2 | 9/2007 | Parunak et al. |
| 7,303,727 B1 | 12/2007 | Dubrow et al. |
| 7,323,140 B2 | 1/2008 | Handique et al. |
| 7,338,760 B2 | 3/2008 | Gong et al. |
| 7,351,377 B2 | 4/2008 | Chazan et al. |
| 7,374,949 B2 | 5/2008 | Kuriger |
| 7,390,460 B2 | 6/2008 | Osawa et al. |
| 7,670,559 B2 | 3/2010 | Chien et al. |
| 7,674,431 B2 | 3/2010 | Ganesan |
| 7,723,123 B1 | 5/2010 | Murphy et al. |
| D637,737 S | 5/2011 | Wilson et al. |

(56) References Cited

U.S. PATENT DOCUMENTS

| | | |
|---|---|---|
| 8,088,616 B2 | 1/2012 | Handique |
| 8,105,783 B2 | 1/2012 | Handique |
| 8,133,671 B2 | 3/2012 | Williams |
| 8,182,763 B2 | 5/2012 | Duffy et al. |
| 8,273,308 B2 | 9/2012 | Handique et al. |
| D669,597 S | 10/2012 | Cavada et al. |
| 8,287,820 B2 | 10/2012 | Williams |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D692,162 S | 10/2013 | Lentz et al. |
| 8,679,831 B2 | 3/2014 | Handique et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| 2001/0012492 A1 | 8/2001 | Acosta et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0046702 A1 | 11/2001 | Schembri |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0015667 A1 | 2/2002 | Chow |
| 2002/0021983 A1 | 2/2002 | Comte et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0068357 A1 | 6/2002 | Mathies et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155477 A1 | 10/2002 | Ito |
| 2002/0169518 A1 | 11/2002 | Luoma et al. |
| 2002/0187557 A1 | 12/2002 | Hobbs et al. |
| 2003/0019522 A1 | 1/2003 | Parunak |
| 2003/0022392 A1 | 1/2003 | Hudak |
| 2003/0049174 A1 | 3/2003 | Ganesan |
| 2003/0049833 A1 | 3/2003 | Chen et al. |
| 2003/0064507 A1 | 4/2003 | Gallagher et al. |
| 2003/0070677 A1 | 4/2003 | Handique et al. |
| 2003/0073106 A1 | 4/2003 | Johansen et al. |
| 2003/0083686 A1* | 5/2003 | Freeman et al. ............. 606/181 |
| 2003/0087300 A1 | 5/2003 | Knapp et al. |
| 2003/0096310 A1 | 5/2003 | Hansen et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0190608 A1 | 10/2003 | Blackburn |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0018119 A1 | 1/2004 | Massaro |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0086427 A1 | 5/2004 | Childers et al. |
| 2004/0086956 A1 | 5/2004 | Bachur, Jr. |
| 2004/0141887 A1 | 7/2004 | Mainquist et al. |
| 2004/0200909 A1 | 10/2004 | McMillan et al. |
| 2004/0235154 A1 | 11/2004 | Oh et al. |
| 2005/0013737 A1 | 1/2005 | Chow et al. |
| 2005/0041525 A1 | 2/2005 | Pugia et al. |
| 2005/0042639 A1 | 2/2005 | Knapp et al. |
| 2005/0058574 A1 | 3/2005 | Bysouth et al. |
| 2005/0129580 A1 | 6/2005 | Swinehart et al. |
| 2005/0142036 A1 | 6/2005 | Kim et al. |
| 2005/0186585 A1 | 8/2005 | Juncosa et al. |
| 2006/0177855 A1 | 8/2006 | Utermohlen et al. |
| 2006/0210435 A1 | 9/2006 | Alavie et al. |
| 2007/0243626 A1 | 10/2007 | Windeyer et al. |
| 2008/0017306 A1 | 1/2008 | Liu et al. |
| 2008/0056948 A1 | 3/2008 | Dale et al. |
| 2008/0069729 A1 | 3/2008 | McNeely |
| 2008/0226502 A1 | 9/2008 | Jonsmann et al. |
| 2009/0189089 A1 | 7/2009 | Bedingham et al. |
| 2011/0008825 A1 | 1/2011 | Ingber et al. |
| 2011/0158865 A1 | 6/2011 | Miller et al. |
| 2012/0171759 A1 | 7/2012 | Williams et al. |
| 2012/0258463 A1 | 10/2012 | Duffy et al. |
| 2013/0037564 A1 | 2/2013 | Williams et al. |
| 2013/0071851 A1 | 3/2013 | Handique et al. |
| 2013/0096292 A1 | 4/2013 | Brahmasandra et al. |
| 2013/0101990 A1 | 4/2013 | Handique et al. |
| 2013/0164832 A1 | 6/2013 | Ganesan et al. |
| 2013/0217013 A1 | 8/2013 | Steel et al. |
| 2013/0217102 A1 | 8/2013 | Ganesan et al. |
| 2013/0251602 A1 | 9/2013 | Handique et al. |
| 2013/0280131 A1 | 10/2013 | Handique et al. |
| 2013/0288358 A1 | 10/2013 | Handique et al. |

FOREIGN PATENT DOCUMENTS

| | | |
|---|---|---|
| EP | 0766256 | 4/1997 |
| EP | 1541237 A2 | 6/2005 |
| EP | 2372367 A1 | 10/2011 |
| FR | 2672301 | 8/1992 |
| FR | 2795426 | 12/2000 |
| JP | 58212921 A | 12/1983 |
| JP | H07-290706 | 11/1995 |
| JP | 2001-509437 | 7/2001 |
| JP | A-2001-527220 | 12/2001 |
| JP | 2002-503331 | 1/2002 |
| JP | 2002-215241 | 7/2002 |
| JP | A-2003-500674 | 1/2003 |
| JP | 2003-047839 A | 2/2003 |
| JP | 2004-150797 A | 5/2004 |
| JP | 2004-531360 A | 10/2004 |
| JP | 2005-514718 | 5/2005 |
| JP | 2005-518825 | 6/2005 |
| JP | 2005-176613 A | 7/2005 |
| JP | A-2005-204661 | 8/2005 |
| JP | 2005-291954 A | 10/2005 |
| JP | 2005-532043 | 10/2005 |
| JP | 2006-021156 A | 1/2006 |
| JP | 2006-094866 A | 4/2006 |
| JP | 2007-514405 A | 6/2007 |
| WO | WO 88/06633 | 9/1988 |
| WO | WO 90/12350 | 10/1990 |
| WO | WO 92/05443 | 4/1992 |
| WO | WO 94/11103 | 5/1994 |
| WO | WO 96/04547 | 2/1996 |
| WO | WO 97/05492 | 2/1997 |
| WO | WO 97/21090 | 6/1997 |
| WO | WO 98/00231 | 1/1998 |
| WO | WO 98/22625 | 5/1998 |
| WO | WO 98/49548 | 11/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/072264 | 9/2002 |
| WO | WO 02/078845 | 10/2002 |
| WO | WO 03/012325 | 2/2003 |

(56) References Cited

FOREIGN PATENT DOCUMENTS

| WO | WO 03/012406 | 2/2003 |
|---|---|---|
| WO | WO 03/048295 | 6/2003 |
| WO | WO 03/055605 | 7/2003 |
| WO | WO 03/076661 | 9/2003 |
| WO | WO 2004/007081 | 1/2004 |
| WO | WO 2004/055522 | 7/2004 |
| WO | WO 2004/074848 | 9/2004 |
| WO | WO 2006/010584 | 2/2006 |
| WO | WO 2006/066001 | 6/2006 |
| WO | WO 2006/119280 | 11/2006 |
| WO | WO 2007/044917 | 4/2007 |
| WO | WO 2007/050327 | 5/2007 |
| WO | WO 2007/064117 | 6/2007 |
| WO | WO 2008/030914 | 3/2008 |
| WO | WO 2010/118541 | 10/2010 |

OTHER PUBLICATIONS

Broyles, et al., "Sample Filtration, Concentration, and Separation Integrated on Microfluidic Devices" Analytical Chemistry (American Chemical Society), vol. 75 No. 11: pp. 2761-2767.

Carlen et al., "Paraffin Actuated Surface Micromachined Valve," in IEEE MEMS 2000 Conference, p. 381-385, Miyazaki, Japan, Jan. 2000.

Handique K., et al., On-Chip Thermopneumatic Pressure for Discrete Drop Pumping, Analytical Chemistry, American Chemical Society, Apr. 15, 2001, vol. 73, No. 8, 1831-1838.

Handique, K. et al, "Microflidic flow control using selective hydrophobic patterning", SPIE, vol. 3224, pp. 185-194 (1997).

Livache, T. et al., "Polypyrrole DNA chip on a Silicon Device: Example of Hepatitis C Virus Genotyping", Analytical Biochemistry, vol. 255 (1998), pp. 188-194.

Shoffner, M. A. et al., Chip PCR.I. Surface Passivation of Microfabricated Silicon-Glass Chips for PCR, Nucleic Acids Research, Oxford University Press, 1996, vol. 24, No. 2, 375-379.

Mascini et al., "DNA electrochemical biosensors", Fresenius J. Anal. Chem., 369: 15-22, (2001).

Plambeck et al., "Electrochemical Studies of Antitumor Antibiotics", J. Electrochem Soc.: Electrochemical Science and Technology, pp. 2556-2563, (Dec. 1984).

Wang, "Survey and Summary, from DNA Biosensors to Gene Chips", Nucleic Acids Research, 28(16):3011-3016, (2000).

Brahmasandra et al., On-chip DNA detection in microfabricated separation systems, SPIE Conference on Microfluidic Devices and Systems, 1998, vol. 3515, pp. 242-251, Santa Clara, CA.

Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.

Meyers, R.A., Molecular Biology and Biotechnology: A Comprehensive Desk Reference; VCH Publishers, Inc. New York, NY; (1995) pp. 418-419.

Orchid BioSciences, Inc., www.orchid.com, Jul. 6, 2001.

Caliper Technologies Corp., www.calipertech.com, Jul. 6, 2001.

Burns et al., 1998, "An Integrated Nanoliter DNA Analysis Device," Science 282:484-487.

Handique and Burns, 2001, "Mathematical Modeling of Drop Mixing in a Slit-Type Microchannel", J. Micromech. Microeng. 11:548-554.

Handique et al., 2000, "On-Chip Thermopneumatic Pressure for Discrete Drop Pumping," Anal. Chem. 73:1831-1838.

Handique et al., 2000, "Nanoliter Liquid Metering in Microchannels Using Hydrophobic Patterns," Anal. Chem. 72:4100-4109.

Jörg P. Kutter et al., Solid Phase Extraction on Microfluidic Devices, *J. Microcolumn Separations*, 2000 12(2), pp. 93-97.

Richard D. Oleschuk et al., Trapping of Bead-Based Reagents within Microfluidic Systems: On-Chip Solid-Phase Extraction and Electrochromatography, Anal. Chem. 2000, 72, pp. 585-590.

M. Sofi Ibrahim et al., Real-Tune Microchip PCR for Detecting Single-Base Differences in Viral and Human DNA, Anal. Chem. 1998, 70, pp. 2013-2017.

Martin U. Kopp et al., Chemical Amplification: Continuous-Flow PCR on a Chip, Science, www.sciencemag.org., vol. 280, May 15, 1998, pp. 1046-1048.

M. Allen Northrup et al., A Miniature Analytical Instrument for Nucleic Acids Based on Micromachined Silicon Reaction Chambers, Analytical Chemistry, vol. 70, No. 5, Mar. 1, 1998, pp. 918-922.

Philip L. Ross et al., Analysis of DNA Fragments from Conventional and Microfabricated PCR Devices Using Delayed Extraction MALDI-TOF Mass Spectrometry, Anal. Chem. 1998, 70, pp. 2067-2073.

Larry C. Waters et al., Microchip Device for Cell Lysis, Multiplex PCR Amplification, and Electrophoretic Sizing, Anal. Chem. 1998, 70, pp. 158-162.

E.T. Lagally et al., Single-Molecule DNA Amplification and Analysis in an Integrated Microfluidic Device, Anal. Chem. 2001, 73, pp. 565-570.

Julia Khandurina et al., Microfabricated Porous Membrane Structure for Sample Concentration and Electrophoretic Analysis, Anal. Chem. 1999, 71, pp. 1815-1819.

Bing He et al., Microfabricated Filters for Microfluidic Analytical Systems, Anal. Chem. 1999, 71, pp. 1464-1468.

James P. Brody et al., Diffusion-based extraction in a microfabricated device, Sensors and Actuators, vol. A58, No. 1, Jan. 1997, pp. 13-18.

Bernhard H. Weigl et al., Microfluidic Diffusion-Based Separation and Detection, Science, www.sciencemag.org, Jan. 15, 1999, vol. 283, pp. 346-347.

* cited by examiner

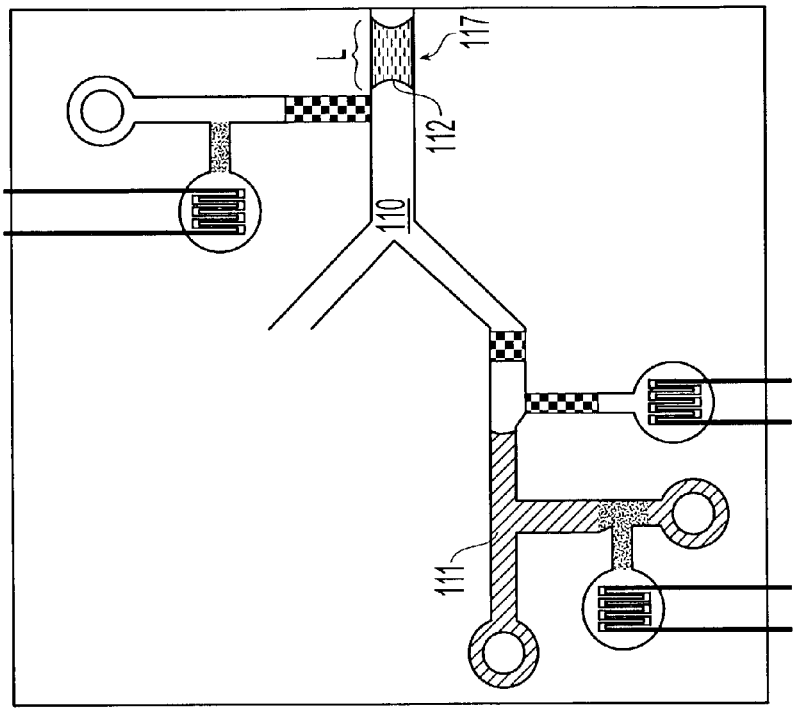
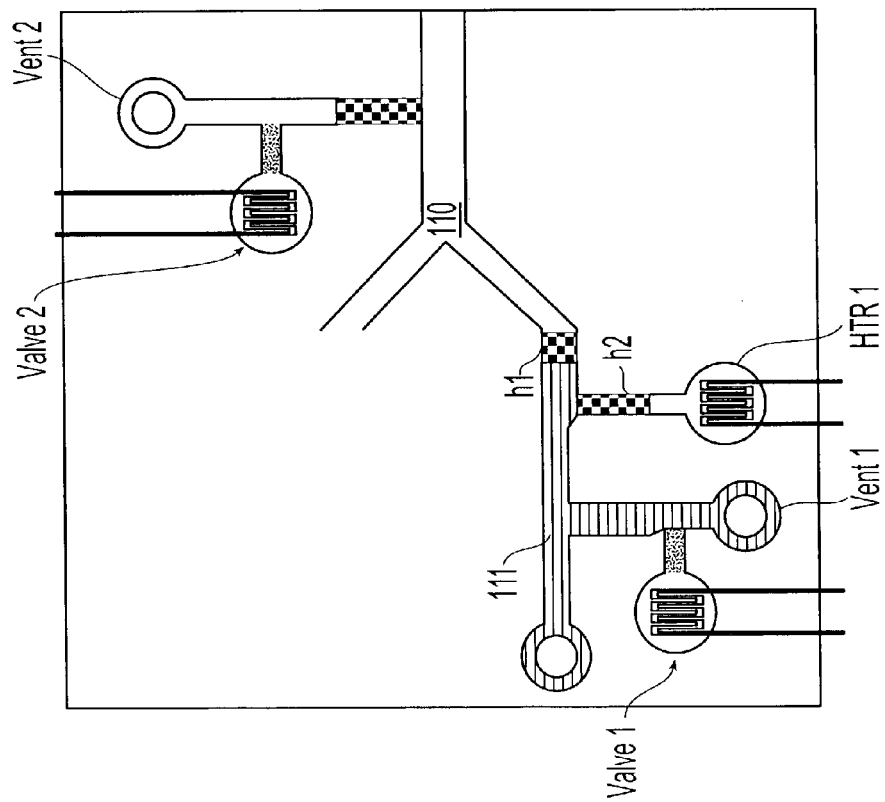
Fig. 8B
Fig. 8A

METHODS AND SYSTEMS FOR CONTROL OF GENERAL PURPOSE MICROFLUIDIC DEVICES

This application is a continuation-in-part of U.S. application Ser. No. 09/819,105 filed Mar. 28, 2001 now U.S. Pat. No. 7,010,391, which is hereby incorporated by reference herein in its entirety.

1. FIELD OF THE INVENTION

The present invention relates to the field of microfluidics. More particularly, the present invention is directed to control methods, control systems, and control software for microfluidic devices that operate by moving discrete micro-droplets through a sequence of determined configurations.

2. BACKGROUND OF THE INVENTION

Micro/nano technology devices are known in the art as devices with components on the scale of 1 μm to 100s of μm that cooperate to perform various desired functions. In particular, microfluidic devices are micro/nano technology devices that perform fluid handling functions, which, for example, cooperate to carry out a chemical or biochemical reaction or analysis.

Most microfluidic devices in the prior art are based on fluid flowing through microscale passages and chambers, either continuously or in relatively large aliquots. Fluid flow is usually initiated and controlled by electro-osmotic and electrophoretic forces. See, e.g., U.S. Pat. No. 5,632,876, issued Apr. 27, 1997 and titled "Apparatus and Methods for Controlling Fluid Flow in Microchannels;" U.S. Pat. No. 5,992,820, issued Nov. 30, 1999 and titled "Flow Control in Microfluidics Devices by Controlled Bubble Formation;" U.S. Pat. No. 5,637,469, issued Jun. 10, 1997 and titled "Methods and Apparatus for the Detection of an Analyte Utilizing Mesoscale Flow Systems;" U.S. Pat. No. 5,800,690, issued Sep. 1, 1998 and titled "Variable Control of Electroosmotic and/or Electrophoretic Forces Within a Fluid-Containing Structure Via Electrical Forces;" and U.S. Pat. No. 6,001,231, issued Dec. 14, 1999 and titled "Methods and Systems for Monitoring and Controlling Fluid Flow Rates in Microfluidic Systems."

These devices are relatively disadvantageous because, inter alia, they require larger volumes of reactants by virtue of their flow-based design, and fluid control by electro-osmotic and electrophoretic forces typically requires relatively large voltages, which may be dangerous and are difficult to generate in small portable control devices. Control devices for microfluidic devices based on such technologies are larger, at least desktop in size.

More advantageous technologies for microfluidic devices have been developed by one or more of the inventors of the present application and others. This advantageous technology manipulates very small aliquots of fluids (known herein as "micro-droplets") in microscale passages by relying largely on pressure and other non-electric forces. These devices are advantageous in that smaller volumes of reagents are required, and in that non-electric forces can be generated by smaller voltages, of the order of magnitude output by standard microelectronic components. See, i.e., U.S. Pat. No. 6,057,149, issued May 2, 2000 and titled "Microscale Devices And Reactions In Microscale Devices;" U.S. Pat. No. 6,048,734, issued Apr. 11, 2000 and titled "Thermal Microvalves in a Fluid Flow Method" and U.S. Pat. No. 6,130,098, issued Oct. 10, 2000.

However, to the knowledge of the inventors, no well-structured control systems have been provided for such micro-droplet-based microfluidic devices that exploits the essential advantages of such devices.

Citation or identification of any reference in this Section or any section of this application shall not be construed that such reference is available as prior art to the present invention.

3. SUMMARY OF THE INVENTION

It is one of the objects of the present invention to overcome this deficiency in the art and provide methods and systems for controlling micro-droplet-based microfluidic devices that exploits their essential advantages. Because of the structure and properties of such microfluidic devices, the methods and systems of this invention can be implemented in a wide range of embodiments, from entirely handheld embodiments to laboratory embodiments for performing high-throughput reactions and analyses. Further, because of the structure and properties of such microfluidic devices, these methods and systems can be controlled by users to perform diverse reactions and analysis in a manner similar to programming a computer.

Thus, the present invention has for one of its several objects the provision of programmable control systems and software for what are known herein as "digital" microfluidic devices. The control systems provided, reflecting the preferred microfluidic devices themselves, have a generally hierarchical design in which detailed and lower-level device control operations are organized into a smaller number of basic control functions (also referred to as "actuators"), while overall and higher-level device control is organized as sequences of the basic functions (also referred to as "sub-assemblies") that cause a particular device to carry out intended reactions of analyses.

Preferably, the control systems of the present invention are further adaptable to many different types of digital microfluidic devices and intended reactions, scalable to devices of various complexities, simple to program, and economical to build. In one embodiment, where a microfluidic device has sufficient flexibility so that it can perform several different reactions or analyses (with the same or different input reagents), a suitable control system will be able to perform different control methods for causing the microfluidic device to perform these different reactions or analyses. These different methods may be implemented by different programs executed by the controller, and advantageously, the controller may present a user with a selection for choosing which different programs to execute. Such a user selection may include indicia, which are visible, auditory, or tactile symbols, of the available programs and processes.

Further, a microfluidic device may be compatible with one or more reagent packages, which are further, generally simpler, microfluidic devices that are designed to supply different reagents to the processing device. In some embodiments, the reagent packages may include certain microfluidic processing components, especially components useful in reagent metering and dispensing. Where a microfluidic device is accompanied by one or more reagent packages, a suitable controller will also be capable of controlling the reagent packages to supply their reagents.

The present invention may also include a general purpose processing kit comprising a general purpose microfluidic processing device, one or more compatible reagent packages, and media with software for use by a controller of the processing device and the reagent package. These general purpose kits may be configured for use in selected application areas, such as medical diagnosis, industrial process control and analysis, environmental analysis, and so forth.

In more detail, the present invention includes, but is not limited to, the following embodiments. In a first, basic embodiment, the present invention includes systems and methods for controlling a microfluidic processor that comprises at least one passage capable of confining at least one micro-droplet, and in response to applied control signals, can manipulate at least the position of the micro-droplet. The basic method first selects a next micro-droplet processing request from a pre-selected micro-droplet processing program, which most generally may simply be a group of micro-droplet processing requests that achieve an intended process or analysis, where each request specifies the creation or transformation of at least one micro-droplet confined in the microfluidic processor, and where each processing request is associated with a next processing request. Next, the basic method generates control signals that, when applied to the microfluidic processor, cause the processor to perform the micro-droplet creation, or the micro-droplet transformation, or other micro-droplet manipulation specified by the processing request. These two steps are repeated until there are no next processing requests to be selected. Accordingly, this method causes the microfluidic processor to perform the pre-selected group of processing requests (program) in response to the generated control signals, and thereby to carry out the intended process or analysis.

In aspects of the basic embodiment, the micro-droplet processing requests specify, for example, (i) the creation of at least one additional micro-droplet, or (ii) the moving of at least one micro-droplet from a first position to a next position, or (iii) the combining of at least two micro-droplets to form at least one additional micro-droplet, or (iv) the mixing of at least one micro-droplet, or (v) the metering of at least one micro-droplet from a fluid reservoir. In a preferred type of microfluidic processor, micro-droplets may be moved by local gas pressure generated by a controllable gas pressure generator. Such a gas pressure generator, as well as other preferred microfluidic processing components, may be activated and respond to local heating by one or more heaters activated by control signals. For example, the heaters may be resistances supplied with electrical power by the control signals. Also, preferably, a microfluidic processor provides at least one sense signal responsive, for example, to the successful/unsuccessful completion of at least one sensed micro-droplet processing request. Then micro-droplet processing requests may then be selected in response to sensing an successful/unsuccessful signal relating to the previous request.

A general purpose microfluidic processor is one that is capable of carrying out two or more different processes or analyses on contained micro-droplets, and in one embodiment may by implemented by including switching components that provide for alternate next micro-droplet paths, and thereby permit different processes to be selectively programmed. Generally, a switch-type component is one that responds to at least one micro-droplet processing request that specifies that a micro-droplet be moved from a first position to a selected one of a plurality of possible next positions (at least two next positions). In an exemplary embodiment, a switch component may include a passage from a first position that branches into a number of next passages leading to the possible next positions where each of the branch passages may be obstructed in response to control signals. Then, in response to a processing request specifying that a micro-droplet move to a selected next position, control signals are generated causing obstruction of paths from the first position to all the plurality of possible next positions except the selected next position, so that the micro-droplet may move only along the non-obstructed, selected passage to the selected next position. In the exemplary embodiment, the paths may be obstructed by a low-melting-temperature material that is melted in response to a control signal.

A preferred application of the methods and systems of the present invention is to carry out an intended chemical process (such as an analysis and including biotechnological processes) in one or more micro-droplets in the microfluidic processor. For such an application, therefore, the pre-selected group of processing requests (processing program) causes the intended chemical process to be carried out in at least one micro-droplet by first causing formation of a micro-droplet having a composition suitable for a pre-selected chemical process. For example, a plurality of micro-droplets comprising reagents necessary for the chemical process may be combined into one micro-droplet which is then mixed. Second, the requests then carry out the pre-selected chemical process in the suitable micro-droplet, for example, by waiting for a time sufficient for occurrence of the reaction, or by exciting the suitable micro-droplet with thermal heating, or electromagnetic radiation, or the like. Preferably, the processing program generates further control signals for sensing the composition of the micro-droplet in which the chemical process was carried out, for example, by means of electromagnetic signals such as light.

In a further embodiment, the systems and methods of the present invention process a pre-selected group of micro-droplet processing requests (a micro-droplet processing program) that includes at least one processing request (a branching request) with two or more associated next requests. Generally, the next branch may be selected in response to sense signals received from the processor or to user input directing performance of a particular analysis, or the like. Such a processor, therefore, as well as including at least one passage capable of confining at least one micro-droplet responsive to applied control signals, also provides sense signals responsive to at least one micro-droplet that may be received and acted on by the systems and methods of the present invention, for example, to select a next processing request at a branch request.

Processing micro-droplet requests, wherein each request specifies as above the creation or transformation of at least one micro-droplet, proceeds generally as above: a next micro-droplet processing request is selected from the micro-droplet processing program; and in response to the selected request, control signals are generated that, when applied to the microfluidic processor, cause that processor to perform the micro-droplet creation or transformation specified by the processing request. However, at a branch request, the relevant processor-provided sense signals (or user input) is interrogated, and the next branch chosen in response. For example, where a microfluidic processor includes switching components that provide for alternate next micro-droplet paths, the next path may be selected and appropriate control signals generated, in response to a previous sense signal or signals.

Received sense signal may be responsive to, for example, the successful/unsuccessful completion of at least one prior micro-droplet processing request, or to a temperature in the microfluidic device, or to a characteristic of at least one micro-droplet confined in the processor. Micro-droplet characteristics may include its position, or its composition, or its temperature, or the like.

In further embodiments, microfluidic processors of the present invention are not limited to processing solely liquid or fluid samples or reagents. For example, reagents or samples may be provided to the processor in a solid form (that is, as a powder or in a granular form), and when ready for use, the processor may cause an appropriate liquid solvent to contact the solid form so that the solid form may mix, dissolve, or otherwise disperse in the solvent for processing. Instead of a solid-form, a reagent or a sample may also be provided as a viscous liquid, as a gel, or as another semi-solid form, which is dispersed in an appropriately less viscous solvent for processing by the microfluidic processor. Samples of reagents may also be provided in a gaseous form, or as a liquid requiring pressurization, or so forth.

The present invention also includes embodiments with a reagent package (also referred to as a "reagent pack") which itself is a microfluidic device, but one adapted primarily to providing reagents, to a microfluidic processor adapted primarily to carrying out intended processes. The term "reagents" is generally understood herein to include solvents, catalysts and the like, as well as compounds (reagents) that are actually transformed in an intended chemical process and samples for analysis. Thus, a reagent package includes at least one reservoir in fluid communication with at least one outlet port, wherein the reagent pack can be mated with a microfluidic processor so that the outlet port is in fluid communication with an inlet port of the processor allowing so that a reagent in the reservoir can be supplied to the microfluidic processor.

Reagent packs may be configured with an aliquot of a reagent (or reagents) used in a particular process. The fluid reservoirs may also include a charge of pressurized gas, or a controllable gas-pressure generator in gas communication with the reservoir, or the like for providing a gas-pressure to expel the reagent through the outlet port. Reagent packs may also include contacts, which may mate with contacts on a microfluidic processor and/or with external contacts on a controller, by means of which control signals can be applied to the pack for activating controllable components, such as a gas-pressure generator. In further embodiments, reagents may be stored in a reservoir as a solid (or gaseous) form that is readily miscible with a solvent stored in a separate reservoir, such that prior to dispensing, the solid form is mixed or dissolved in the solvent. In further embodiments, a reagent pack may include additional micro-fluidic processing components, such as a metering sub-assembly for expelling a metered amount of a reagent through the outlet port. The metering sub-assembly may be activated by control signals applied to the contacts. In fact, further embodiments of the present invention include configurations where a process or analysis may be carried out by two (or more) separate microfluidic devices that may be mated for fluid communication of intermediate micro-droplets.

In the absence of reagent packages, required reagents may be pre-loaded into reservoirs on a microfluidic processor itself, and then metered by on-processor components when needed during a process. Here, with the exception of loading samples, there need be little or no user or external interaction during a process. Alternatively, reagents may be loaded into a microfluidic processor just before or during execution of a process. Then, the systems and methods of the present invention would include user display of necessary loading instructions, or would activate automatic equipment to perform the reagent loading.

In another embodiment, the methods and systems of the present invention permit a user to choose which of several possible processes to carry out with a particular microfluidic processor, particularly a general purpose processor having one or more switching components. In these embodiments, an intended process would be selected from a plurality of predetermined, possible processes (or analyses), wherein each predetermined process is associated with a group of micro-droplet processing requests (a micro-droplet processing program) for carrying out the predetermined process (or analysis). Advantageously, process selection is under user control. For example, the methods and systems of the present invention may display indicia to a user, the indicia representing the predetermined processes available for selection. The user would then input information representing selection of one of the available processes, so that the user-selected process is then performed by the microfluidic processor. The displayed indicia preferably are visible, auditory, or tactile symbols that are recognizable by a user and represent the available programs and processes The micro-droplet processing requests and programs and the methods of their processing are as described in this invention's other embodiments. In particular, the programs include requests specifying the creation or transformation of at least one micro-droplet, and are processed by selecting a next micro-droplet processing request from the program (until no processing requests remain to be selected), and generating control signals that, when applied to the microfluidic processor, cause that processor to perform the micro-droplet creation or the micro-droplet transformation specified by the selected processing request. In this manner, the chosen processing program and its intended process is carried out.

In situations where two or more different microfluidic processors may be capable of executing a particular processing program, the present invention may further display to a user indicia representing the types of suitable microfluidic processors capable of performing the micro-droplet processing request and requesting that a microfluidic processor of one of the associated types be made available. Suitable types of microfluidic processors may be explicitly stored as part of the processing program, or may be implicitly determined by the methods of this invention by comparing the processing resources required by a program with the resources supplied by the types of microfluidic processors. Processing resources required by a program may be stored along with the other program information, while available processor resources may be available from a separate data source. In a similar manner, each predetermined process (and processing program) may be associated with certain needed reagents, and advantageously the present invention may display to the user indicia representing one or more types of reagent packs comprising aliquots of these reagents, and requesting that a reagent pack of one of the associated types be made available.

The present invention also includes digital controllers for performing the methods of the present invention. These controllers provide control signals to control microfluidic processors comprising a passage capable of confining a micro-droplet responsive to applied control signals. They include at least one digital store for storing at least one or more micro-droplet processing requests, or for storing a pre-selected and structured group of micro-droplet processing requests (a micro-droplet processing program), or for storing a plurality of predetermined processes each accompanied by a stored processing program. Each stored micro-droplet processing request includes encoded instructions to the digital controller for generating control signals that cause the creation or transformation of at least one micro-droplet confined in the microfluidic processor, including, for example, the controllable switching of a micro-droplet among a plurality of next positions, the formation a micro-droplet having a composition suitable for a pre-selected chemical process or chemical reaction from reagents stored in the reservoirs (on or off the processor), the performance of a pre-selected chemical process in a suitable micro-droplet, and the like. Thereby, a processor program including one or more such processing requests may cause a digital controller to generate the necessary control signals so that a microfluidic processor may carry out a predetermined chemical process in at least one micro-droplet.

A digital controller also preferably includes at least a first and a second digital processing element. The first digital processing element selects a next micro-droplet processing request from the stored pre-selected group of micro-droplet processing requests (program) until no next processing requests remain to be selected. In embodiments where the microfluidic processor provides sense signals, the first digital processing device may receive these sense signals (or user input) and then select one or more micro-droplet processing requests from the program in response to the received signals. Certain received sense signals may be responsive (directly or indirectly) to a characteristic of at least one micro-droplet, for example, the position of the micro-droplet or the composition of the micro-droplet, or the like. Other sense signals may be primarily responsive to conditions in the microfluidic processor, for example, to a temperature in the microfluidic device, or the like. Where at least one micro-droplet processing request further specifies the moving of at least one micro-droplet from a first position to a selected one of a plurality of possible next positions (that is, a switch sub-assembly), the first digital processing element may select the next position to move to in response to at least one received sense signal.

The second digital processing element then accepts each selected processing request, and generates control signals according to the request's encoded instructions that, when applied to the microfluidic processor, cause that processor to perform the micro-droplet creation or the micro-droplet transformation specified by the accepted processing request. Thereby the controller causes the microfluidic processor to perform the selected group of processing requests, and to carry out an intended process in the microfluidic device.

These digital processing elements may be implemented in various ways known in the art. In less preferred embodiments, they may be directly implemented as VLSI circuits. In more preferred embodiments, they may be implemented as suitably programmed and coupled microprocessors and analogous control devices or circuitry. For example, each processing element may be implemented in a separate microprocessor, as in the embodiment described below of a DAQ board communicating with a user microcomputer. Or they may be implemented as separate programs (or a single program) in a single microprocessor. The digital store is preferably coupled to the microprocessor executing the program that selects the next microfluidic processing request, but may also be accessible to all microprocessors.

Further general purpose embodiments may include additional digital processing elements. Certain additional elements may display to a user indicia representing a plurality of predetermined processes available for selection, and then accept user input representing selection of an available processes, the selected process being executed by previously-described processing elements. When a predetermined process is further associated (directly or indirectly) with one or more types of microfluidic processors capable of performing the micro-droplet processing requests in the associated program, an additional digital processing element may display to the user indicia representing these types of microfluidic processors, and requesting the user make a processor of one of the associated types available. Similarly, an additional digital processing element may display indicia representing one or more types of reagent packs comprising aliquots of reagents used in a predetermined process and request that a reagent pack of one of the associated types be made available. These additional digital processing elements may be implemented either as parts of a program or as separate programs, and may be executed on a single microprocessor or on two or more coupled microprocessors.

In further embodiments, the present invention includes a microfluidic device kit for performing one or more selected processes. Such a kit preferably includes one or more microfluidic processors capable of performing groups of micro-droplet processing requests (programs) which carry out the selected processes, and one or more reagent packs that can supply reagents to microfluidic processors, wherein the reagents are used in the selected processes. Such kits may also include computer readable media having encoded thereon the group of micro-droplet processing requests, and may also even include a digital controller.

In another embodiment, the present invention includes program products including computer readable media having encoded thereon instructions for causing digital controllers to perform the methods of the present invention. The encoded instructions may comprise microfluidic processor programs comprising one or more micro-droplet processing requests, or may comprise programs necessarily for interpreting and carrying out such microfluidic processor programs, or may comprise both types of programs.

It is understood that the present invention is not limited to the combinations of features and elements described in the above embodiments, but that the invention also includes embodiments that are sub-combinations of features of the above-described embodiments, as well as embodiments that are combinations of the features found in different ones of the above-described embodiments.

4. BRIEF DESCRIPTION OF THE FIGURES

The present invention may be understood more fully by reference to the following detailed description of the preferred embodiment of the present invention, illustrative examples of specific embodiments of the invention, and the appended figures wherein.

Figure 3A:
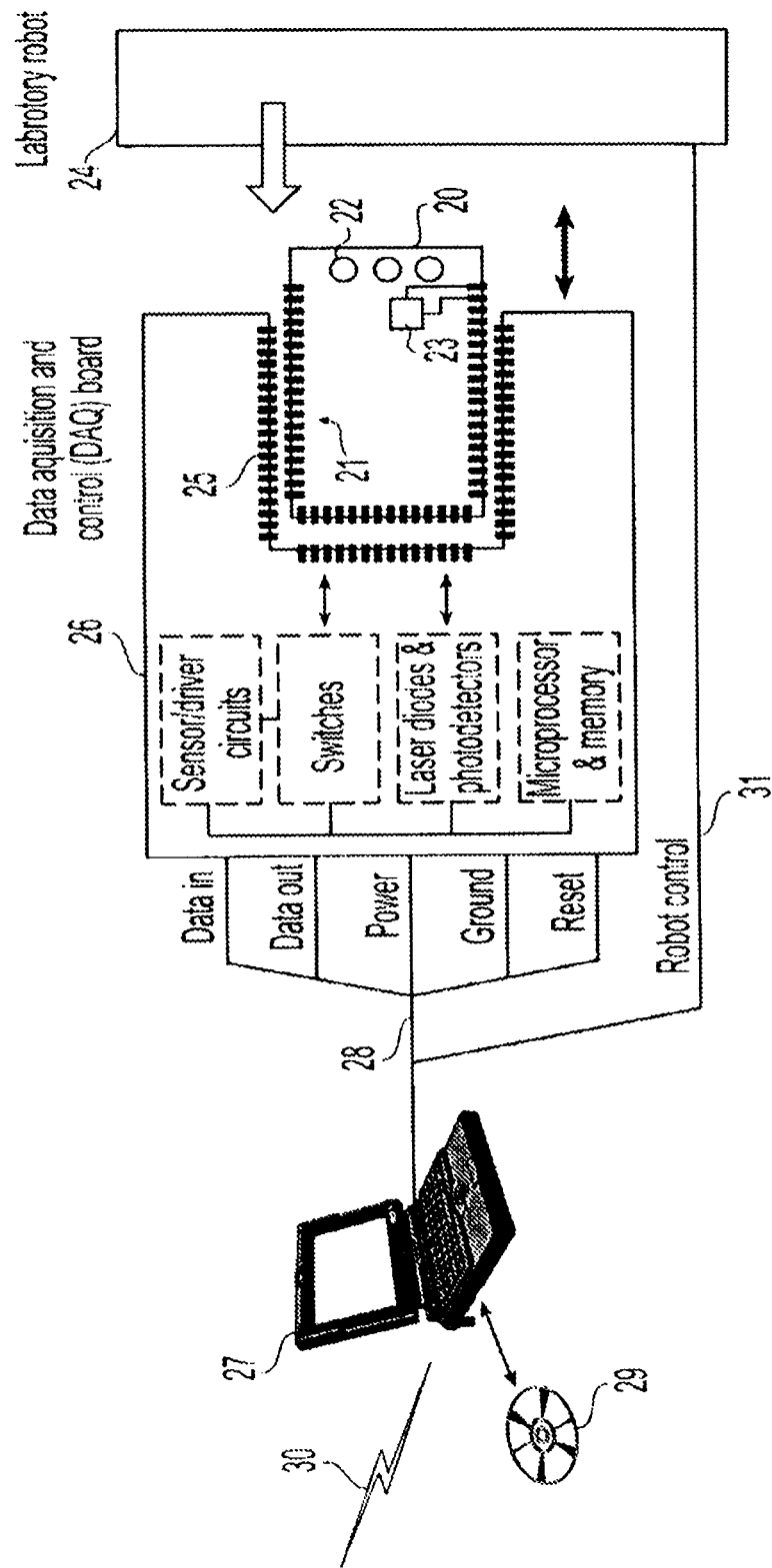
Figure 3B:
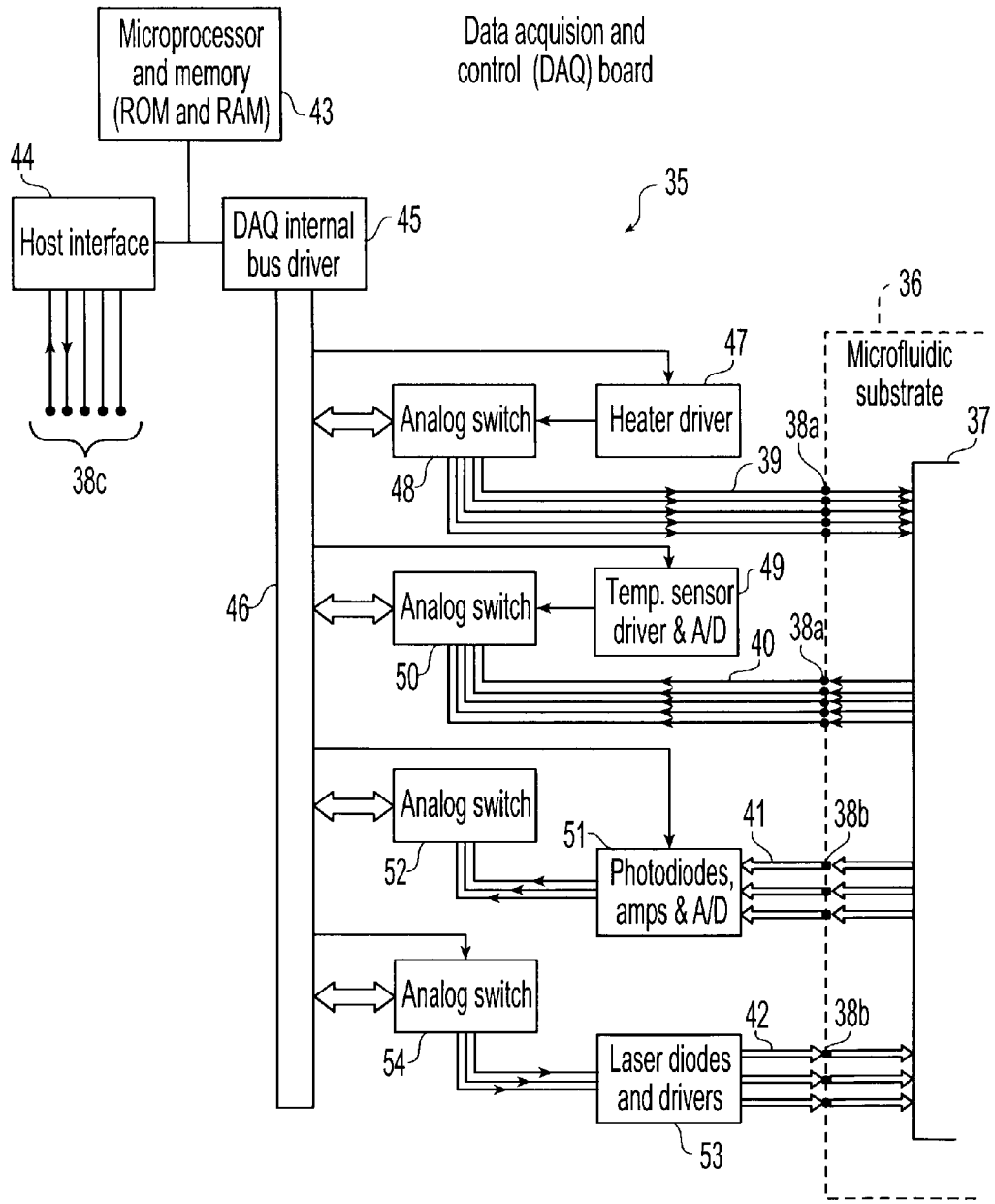
Figure 4A:
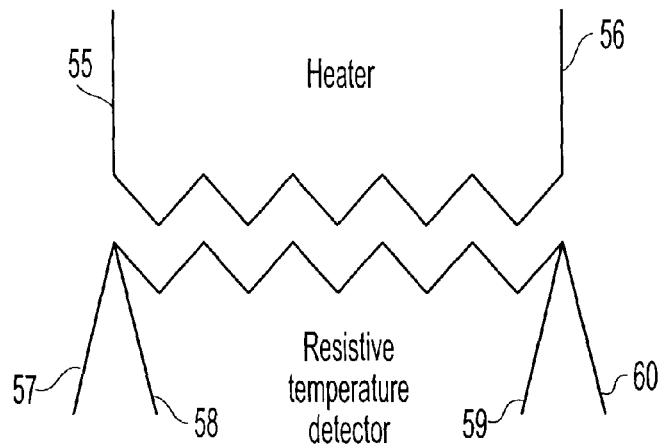
Figure 4B:
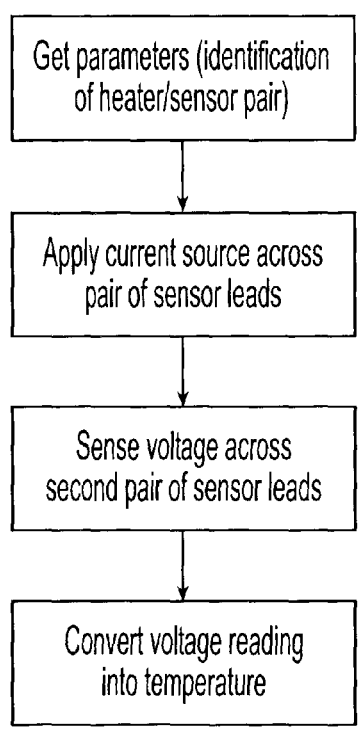
Figure 4C:
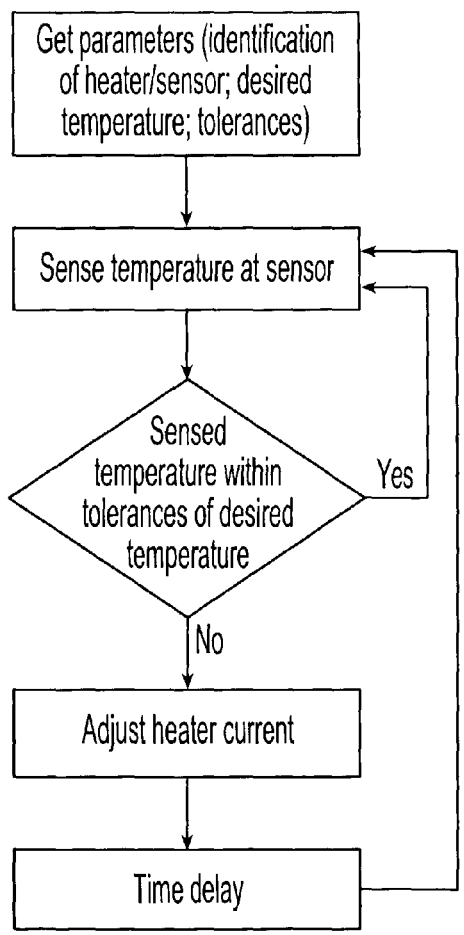
Figure 5A:
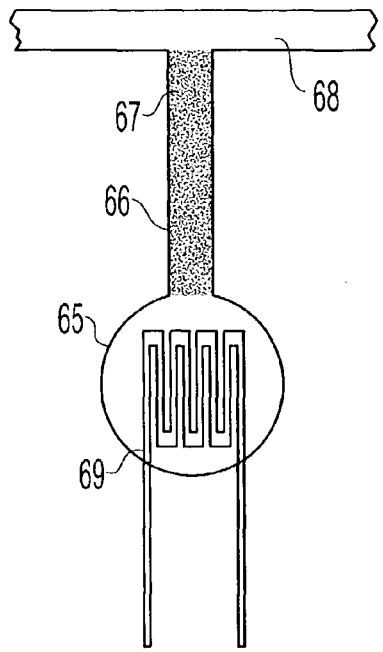
Figure 5B:
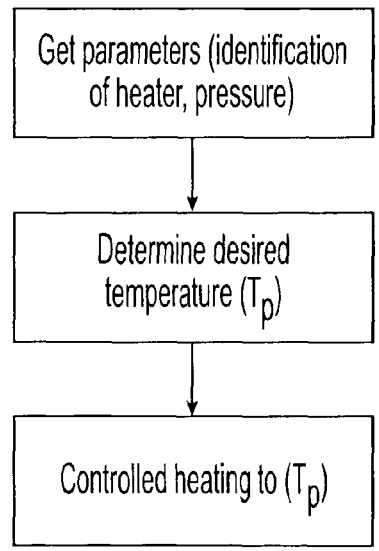
Figure 7B:
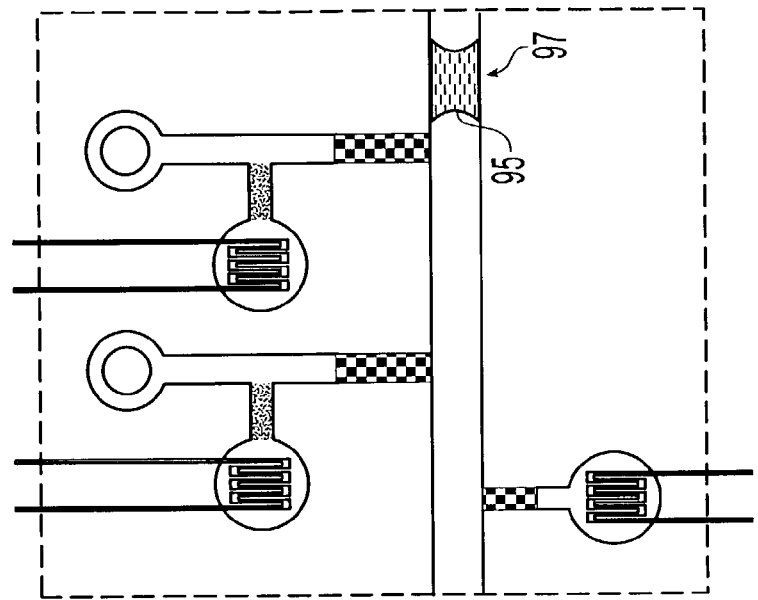
Figure 7A:
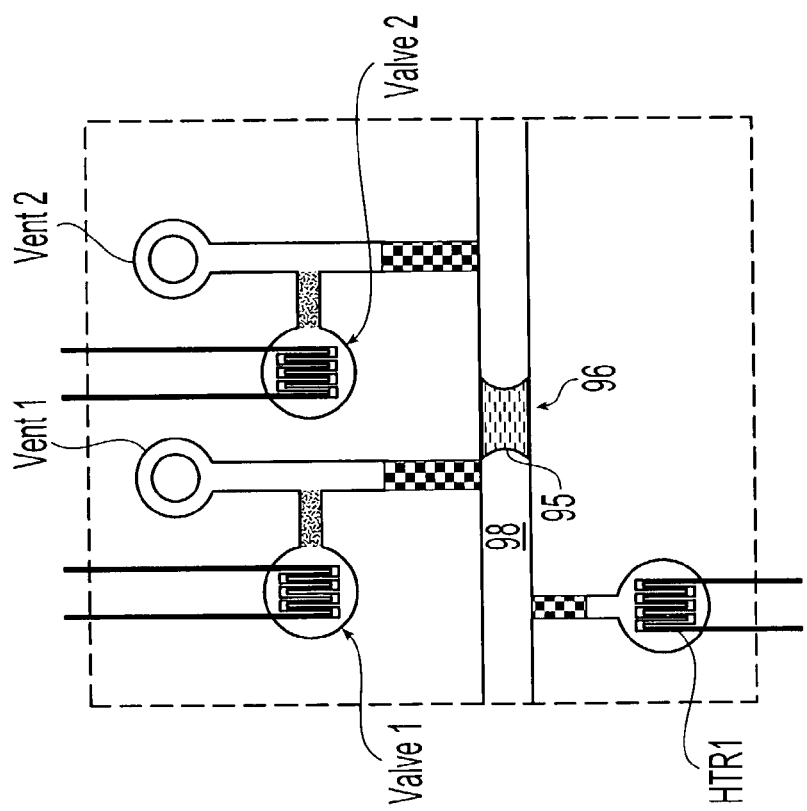
Figure 7C:
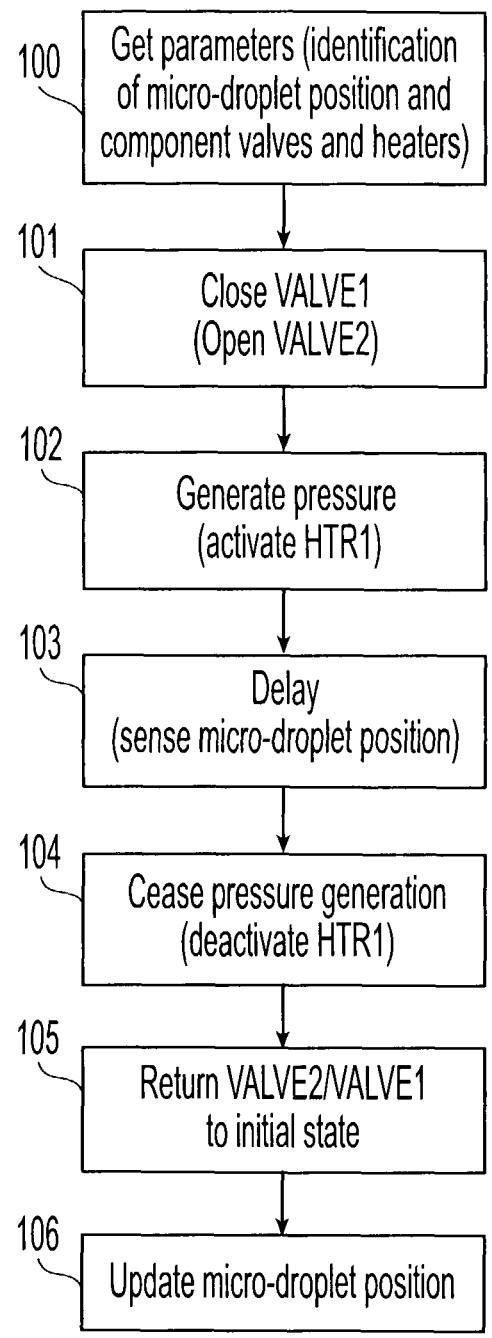
Figure 11B:
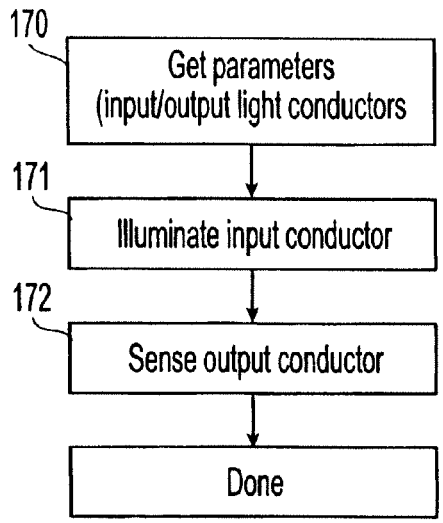
Figure 11A:
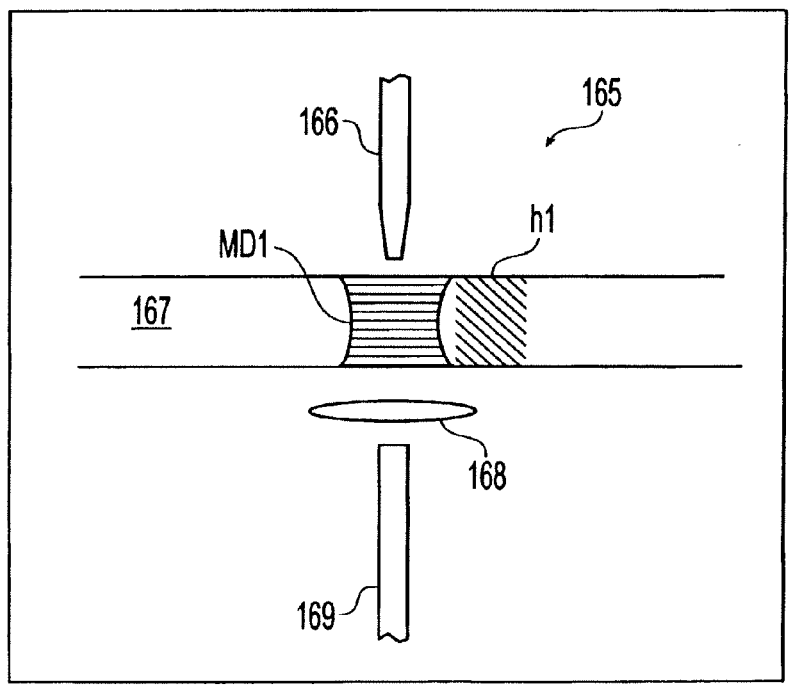
Figure 12:
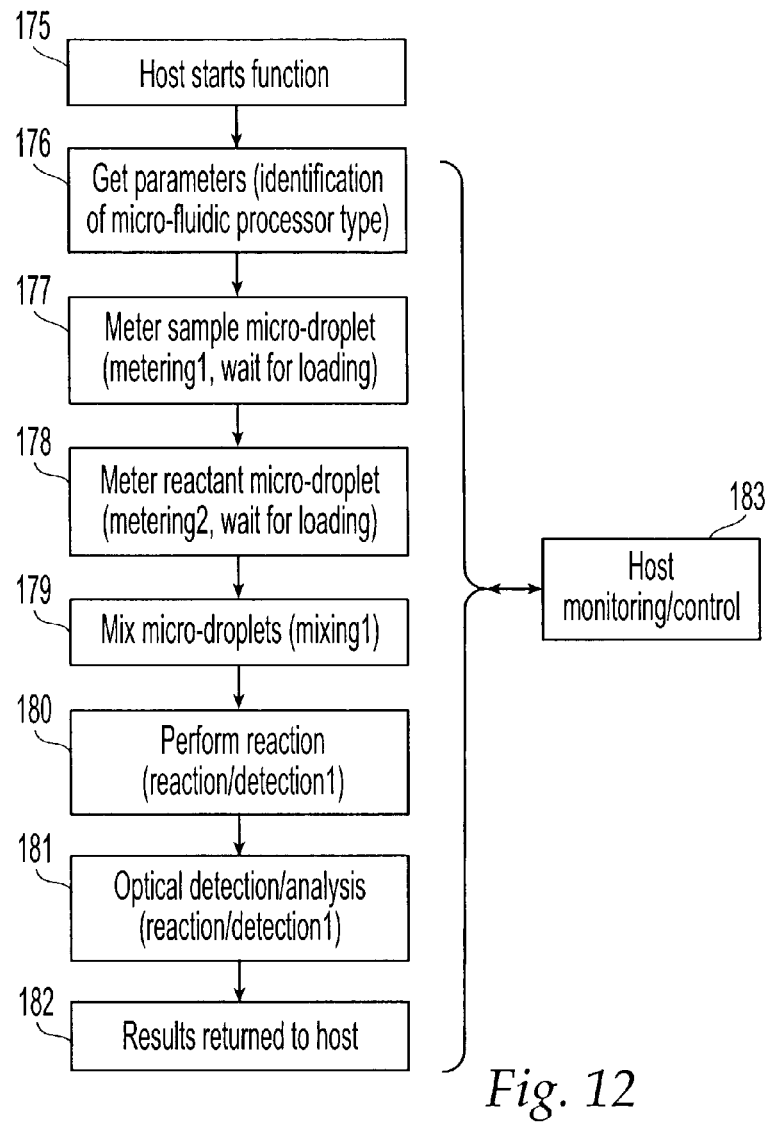
Figure 13:
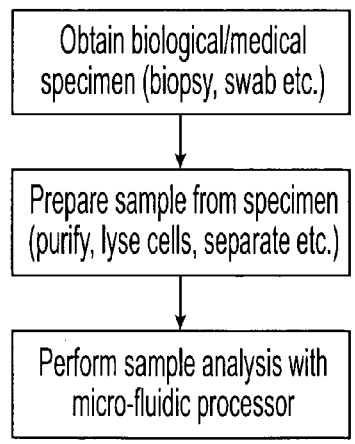
Figure 15:
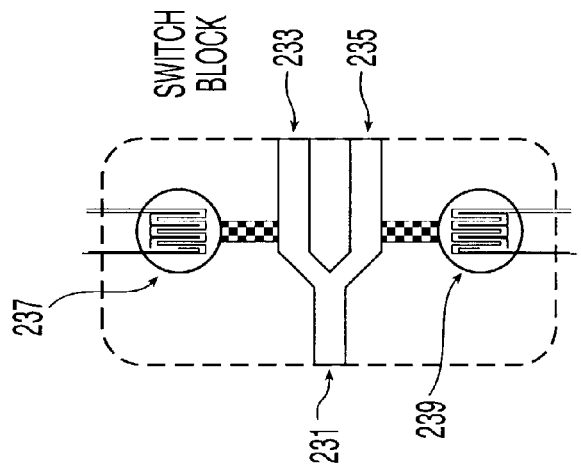
Figure 14:
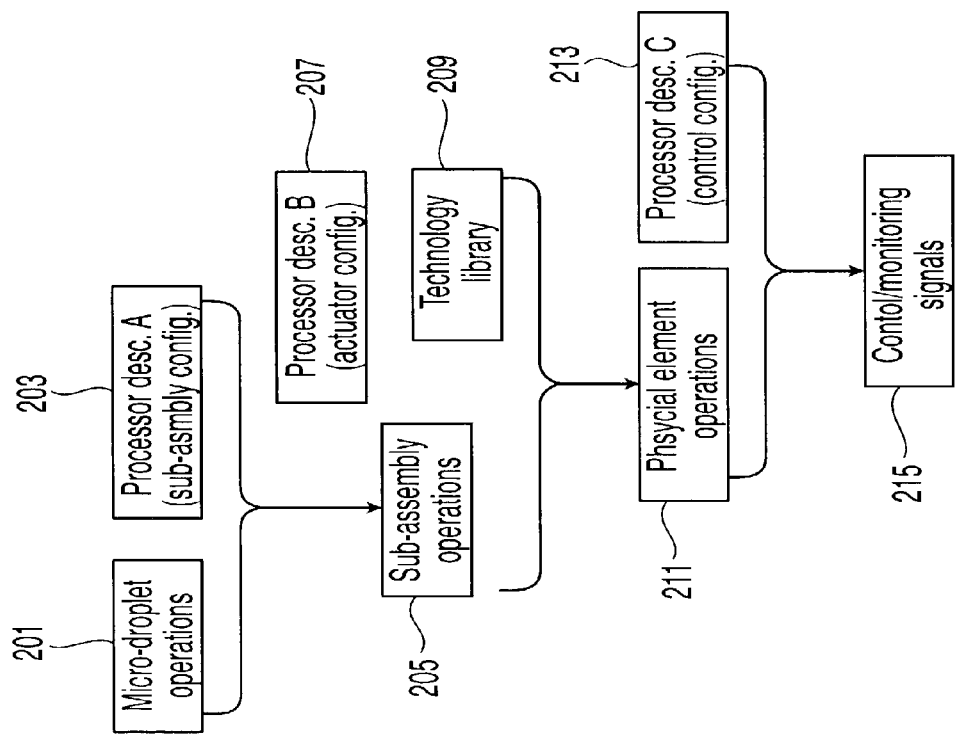
Figure 16:
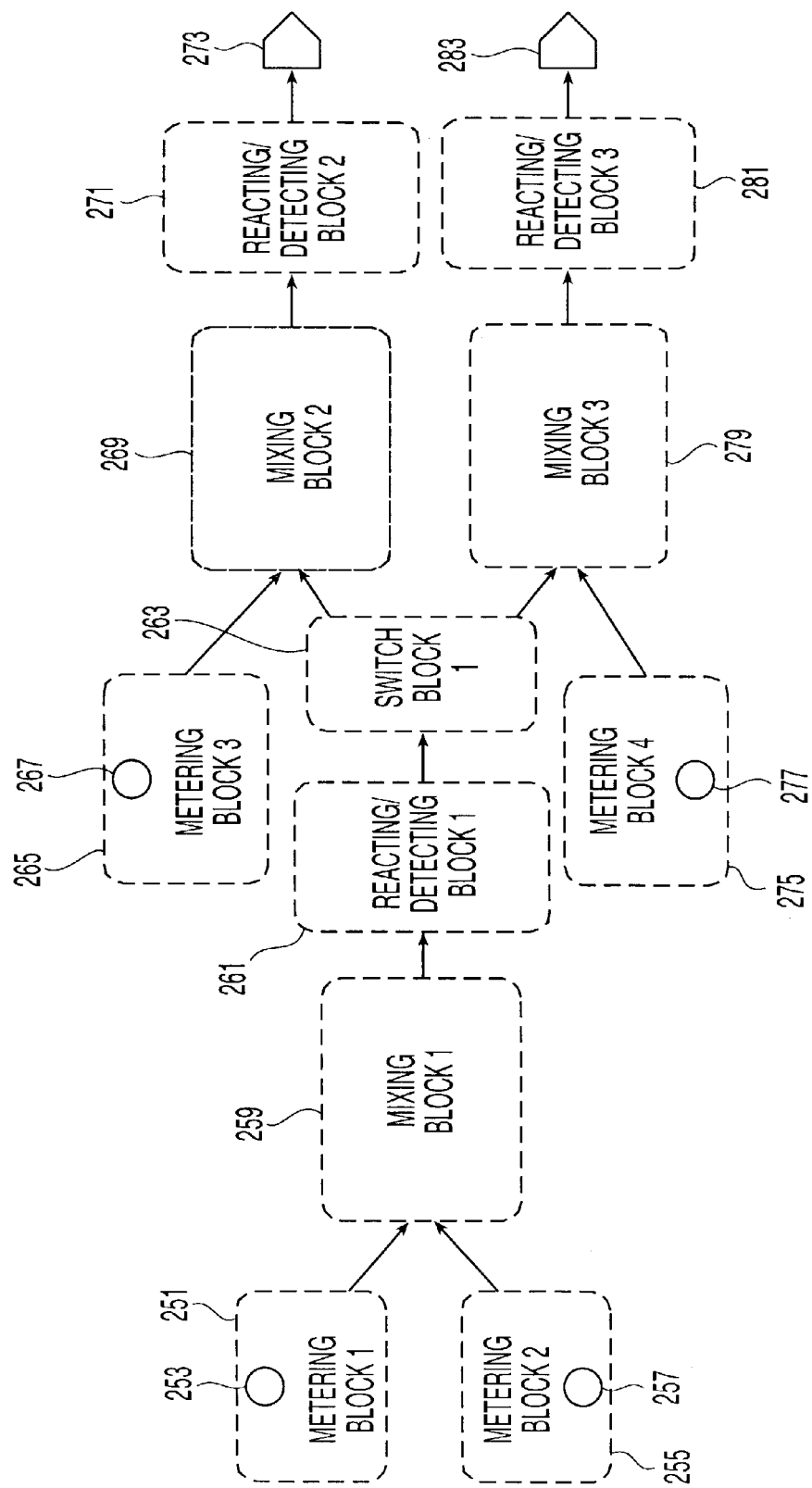
Figure 17C:
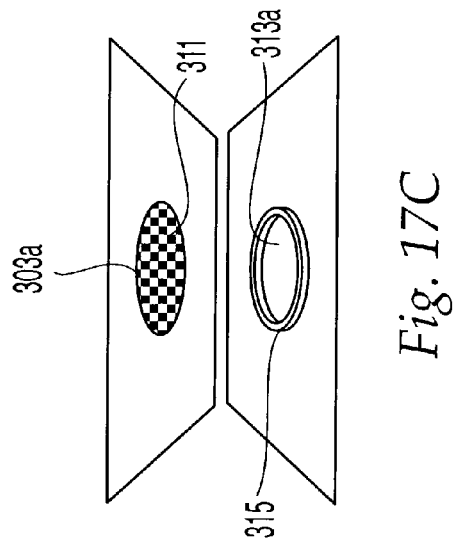
Figure 17A:
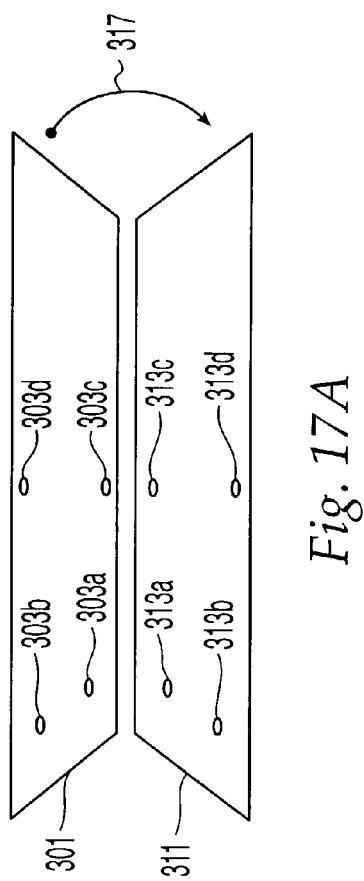
Figure 17B:
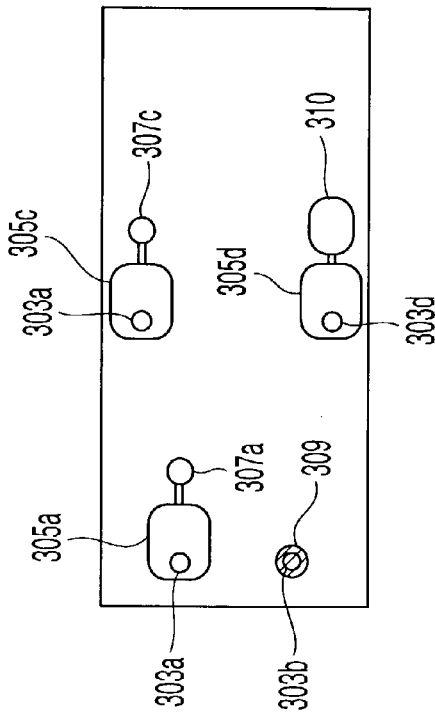

FIGS. 3A-B illustrate preferred control system structure of the present invention;

FIGS. 4A-C illustrate controlled heating component functions for a preferred microfluidic processor;

FIGS. 5A-B illustrate pressure generator component functions for a preferred microfluidic processor;

FIGS. 6A-D illustrate micro-valve actuator functions for a preferred microfluidic processor;

FIGS. 7A-C illustrate micro-droplet motion functions for a preferred microfluidic processor;

FIGS. 8A-D illustrate micro-droplet metering functions for a preferred microfluidic processor;

FIGS. 9A-E illustrate micro-droplet mixing functions for a preferred microfluidic processor;

FIGS. 10A-E illustrate reaction/analysis functions for a preferred microfluidic processor;

FIGS. 11A-B illustrate optic detection actuator functions for a preferred microfluidic processor;

FIG. 12 illustrates an exemplary reaction control function;

FIG. 13 illustrates an exemplary sample preparation method;

FIG. 14 illustrates a preferred microfluidic processor programming paradigm;

FIG. 15 illustrates an switch sub-assembly;

FIG. 16 illustrates an exemplary microfluidic processor of flexible functionality; and FIGS. 17A-C illustrate an exemplary reagent package.

In figures of the same numeric prefix but differing alphabetic suffixes, for example, FIG. 5A and FIG. 5B, identical elements are referenced with the same reference characters.

5. DETAILED DESCRIPTION OF THE PREFERRED EMBODIMENT

Section 5.1 generally describes preferred microfluidic devices controlled by the systems and methods of the present invention; section 5.2 describes preferred embodiments of these control systems and methods in view of the characteristics of preferred microfluidic devices; section 5.3 describes more preferred thermally-controlled microfluidic devices and their more preferred control systems and methods; furthermore, section 5.3 describes additional embodiments.

5.1. Microfluidic Processors and Control Systems

The control systems and methods of the present invention are preferably applied to microfluidic processors. In a preferred embodiment, the control systems and methods are configured to be able to control a plurality of differently configured and implemented microfluidic processors, and also to be able control a single, suitably-configured microfluidic processor to perform a range of different processes.

5.1.1. Microfluidic Processors

The term "microfluidic device" is understood herein to refer to devices that perform chemical or biochemical reactions, analyses, or processes by manipulating fluid reagents in chambers and passages formed in or on a substrate and having generally "nano" to "micro" sizes cross-sectional sizes, for example, from approximately 10 to 50 μm (micro-meter) up to approximately 100 to 1000 μm. The substrate is usually substantially flat with linear dimensions from approximately 1 mm (centimeter) to approximately 20 cm.

The control systems and methods of the present invention apply to "digital" microfluidic devices (also referred to herein as microfluidic "processors"), which are understood to refer to those microfluidic devices that manipulate fluid reagents as separate and discrete micro-droplets having generally "nano" to "micro" volumes, for example, from approximately 1-10 pl (picoliter), up to approximately 1 nl (nanoliter), and further up to approximately 0.5-1 μl (microliter). For example, a micro-droplet of size 50 μm by 50 μm by 500 μm has a volume of about 1 pl; and a micro-droplet of size 1 mm by 1 mm by 1 mm has a volume of 1 nl. Therefore, micro-droplets generally have lengths, for example, approximately from 50 μm to 1 mm to 10 mm (millimeter), that are considerably smaller (approximately an order of magnitude or more smaller) than the dimensions of the device substrate, or less, and consequently during operation the passages and chambers of microfluidic processors are occupied only by a number of discrete micro-droplets, and are otherwise free of fluids. Further, microfluidic processors preferably have passages and chambers with a plurality of predefined positions ("stable positions") at which a micro-droplet may remain motionless even while other micro-droplets are moving, so that at any one time during microfluidic processor operation each micro-droplet in the device is either residing at one of the predefined stable positions or is moving between two of these predefined stable positions.

How stable positions are formed and how micro-droplets are moved are generally processor-technology dependent. In certain technologies, stable positions may be created by configurations and arrangements of passages and chambers and by the forces generated on the micro-droplets. For example, stable positions may occur at positions where a force driving a micro-droplet may be made to vanish, or where forces acting on the micro-droplet balance leave no net driving force, or where an extra force is required for further motion so that in the absence of such extra force a micro-droplet will remain stationary, of the like. In further technologies, a region requiring extra force may be created by a manipulating micro-droplet surface tension, for example, by change in the cross-sectional area or configuration of a passageway, or by change surface coating of a passageway (for example, from hydrophilic to hydrophobic, or vice versa). In other technologies, forces moving micro-droplets may be generated by controlled generation and application of gas pressure, or by electric or magnetic fields, or the like.

Modular Construction

Preferably, the control systems and methods of the present invention apply to microfluidic processors (also referred to herein simply as "processors") which have a substantially modular construction and which are (directly or indirectly) electrically controllable. Substantially modular construction includes those devices in which higher-level "sub-assemblies" are composed from lower-level "actuators/sensors", both of which are composed from the independently-controllable physical elements provided by a particular implementation technology.

In more detail, microfluidic processors may be made by a particular technology to have a limited number of sub-assembly types (preferably less than 10, more preferably less than about 5). Each sub-assembly type is controlled (by controlling its component independently-controllable physical elements) to perform a certain type of micro-droplet manipulation. Exemplary sub-assemblies meter micro-droplets of determined volumes, move micro-droplets between stable positions, combine two or more micro-droplets into a single micro-droplet, mix a possibly heterogeneous micro-droplet, stimulate (or excite) a reaction in a micro-droplet, observe or detect reaction products in a micro-droplet, and so forth. ("Metering" a micro-droplet means herein the creation of a new micro-droplet of approximately known volume or size— for example from 10 pL to 1 μL from a larger micro-droplet or from a fluid reservoir.) Accordingly, the micro-droplets present in a processor during operation may be moved from one set of stable positions (referred to as a "configuration") to subsequent configuration by controlling one or more of the sub-assemblies present in the processor. In this manner, the control systems and methods of this invention carry out analyses, reactions, or processes by controlling a processor's sub-assemblies to perform the required micro-droplet operations.

Sub-assemblies are preferably composed from a limited number (again, preferably less than 10, more preferably less than about 5) of simpler, lower-level components referred to herein as actuators (the class of actuators also including sensors). An exemplary set of basic actuator types, sufficient for many (but not necessarily all) microfluidic processors, includes micro-valve type actuators, pressure generation type actuators (or other types of force generating actuators), heating/cooling type actuators, actuators for monitoring processor state, and so forth. Micro-valves can be controlled to close or open a particular passage, preferably reversibly, to the motion of micro-droplets, gases, or other passage contents. Pressure generation actuators can be controlled to create relative gas pressure (or relative vacuum). Heating/cooling actuators can be controlled to perform localized or generalized heating or cooling. Actuators for state monitoring, sensors, can be controlled to provide input that signals micro-droplet position, local processor temperature, or other parameters. Actuators for optical excitation and detection may also be desirable. For example, radiation may initiate a reaction or monitor reaction products; radiation may also be used to monitor micro-droplet position and composition.

Although actuators may not have sufficient function to directly perform micro-droplet operations, they may be configured into sub-assemblies that can directly manipulate micro-droplets. Sub-assemblies may be composed from actuators in the following exemplary manners. For example, a metering sub-assembly may use a source of gas pressure to pinch off a micro-droplet of determined volume from a fluid-filled passage communicated with a larger fluid reservoir. A sub-assembly for moving a micro-droplet may use a pressure generator actuator to generate mechanical force, gas pressure, to push the micro-droplet. A sub-assembly for combining two micro-droplets may include two inlet passages converging to a single outlet passage, the inlet passages being controlled with micro-valve actuators and being provided with micro-droplet motion actuators. A micro-droplet mixing sub-assembly may be built from a micro-droplet motion actuator that causes sufficiently rapid motion to induce laminar mixing. A reaction/analysis sub-assembly may be built from a chamber (or a length of passage) with access controlled by micro-valve sub-assembly, and provided with actuators to stimulate the reaction, for example, through the application of heat or radiation. A sub-assembly for detecting results of reactions or analyses may, for example, employ sensors of the optical properties of micro-droplets. Further examples of actuators and sub-assemblies will be apparent to one of skill in the art in view of the following description of a specific exemplary digital microfluidic processor.

Both sub-assemblies and actuators (and sensors) are usually composed from still lower-level components because of limitations of what may be directly fabricated in practical device implementation technologies. Practical technologies do not usually provide independently-controllable physical elements with the complex micro-droplet-manipulation functions of sub-assemblies, and often also do not provide independently-controllable physical elements with actuator/sensor functions. Where a technology provides such functional elements, they may be readily employed by the present invention, as will be appreciated from the following description. However, in most cases, the present invention controls sub-assemblies and actuators/sensors as a consequence of directly controlling still lower-level independently-controllable physical elements (also referred to herein as atomically-controllable, or discretely-implemented, or implementation-level components). Atomic or discretely-implemented controllable components are those controllable components that, in the technology used for a particular microfluidic processor, may be directly implemented, or are the simplest controllable components, or may not be decomposed into simpler controllable components, or so forth. Accordingly, in any implementation technology, each basic actuator type is usually constructed from several lower-level and discretely-implemented components which are arranged and controlled to have the particular actuator function. In other words, actuators are usually hierarchical constructs of individual device components available in a particular implementation technology.

For example, in the preferred thermally-controllable class of processors to be described, there is no single atomically-controllable micro-valve component having a micro-valve function available for constructing microfluidic processors. Instead micro-valve actuator function is built from several individual components, each of which is atomically controllable and discretely implemented and which are arranged together and jointly controlled by the methods of this invention to have a micro-valve function.

Although modular and hierarchical processor construction is preferred, this invention is applicable to microfluidic processors with non-hierarchical elements. For example, although each actuator is usually part of a single sub-assembly, it may be advantageous and economical for a single actuator to function as part of two or more sub-assemblies. Similarly, one device-level component may function as part of two or more actuators. How components or actuators may be employed as parts of higher-level functional structures is often technology specific. Such substantially hierarchical construction does not rule out certain actuator types which may be constructed from only a single device component. In some technologies, certain actuator functions may, without limitation, be directly implemented. Nor does it rule out a certain amount of "special purpose" microfluidic functions which may be needed to implement certain limited and specialized functions not describable of the basic and generalized actuator functions.

Electrical Control

For use in the present invention, microfluidic processors are preferably controlled by electrical or (electrically-generated) optical signals applied directly to (connectors extending to) the periphery of a microfluidic processor. Other types of signals, such as pneumatic, hydraulic, mechanical or so forth, which are in turn electrically controlled (indirect electrical control), are preferably used rarely if at all. Also use of external devices (such as robot-type equipment) is preferably minimized, for example being limited to loading of samples or reactants not initially present in the processor, or to otherwise interfacing with the external environment. Therefore, the control systems and methods of the present invention generate electrical (and optical) control signals and apply them to a microfluidic processor in order to control the directly-controllable, device-level components in such patterns as to realize higher-order actuator and sub-assembly functions, and ultimately to perform reactions, analyses, or processes by manipulating micro-droplets.

Preferred electrical control signals are of relatively low voltage preferably less than 50 V (volt), more preferably less than 25 V, and even more preferably less than 15 V or 10 V. Control signals sent to a microfluidic processor from a controller may include, for example, electrical inputs causing internal actuator operation, or optical inputs that excite or probe reaction products. The electrical contacts to which the electrical input signals are applied may be dedicated to single lower-level, independently-controllable physical elements, or according to other embodiments, the electrical contacts may be shared so as to reduce the number of required external contacts.

Further, control systems and methods of this invention are advantageously sensitive to monitoring and feedback signals transmitted from a microfluidic processor sensors and that reflect the effect of prior control signals, such as, for example, whether a specified temperature has been reached, whether a micro-valve opened or closed as controlled, whether a micro-droplet has moved as controlled, and so on. Electrical signals received from a microfluidic processor may include outputs for monitoring device state, for example, temperature-monitoring signals, or micro-droplet-position monitoring signals. Optical signals received may monitor micro-droplet presence, micro-droplet optical characteristics (to determine the results of a reaction or analysis), or so forth. Whether optical signals are generated and detected on a microfluidic processor in response to external electrical control signals, or whether optical signals are externally generated and detected in a control system (also in response to electrical signals) and exchanged optically, for example, over fiber-optic paths with a processor, is an implementation consideration.

Finally, microfluidic processors may be constructed according to various sufficiently-functional technologies that allow micro-droplet-by-micro-droplet control of microfluidic processors. For example, microfluidic processors can be constructed according to the arts of mechanical and silicon-based nano-technologies and injection molding (especially of polymeric materials). Passages may be etched in glass or silicon or plastic (or a polymeric material); valves may include flexible silicon elements actuated by applied voltages; fluids may be moved by moveable nano-elements, or by controlled pressure, either available from an external source or generated internally. A single microfluidic device can be constructed in a single technology, or may include multiple technologies.

5.1.2. Control Methods and Systems

The control systems of the present invention implement the present invention's control methods to generate microfluidic-processor-control signals that cause the processor to perform a determined reaction, analysis, or process.

Processes in a microfluidic processor may be advantageously described and specified in terms of micro-droplets, their residence at and transitions between stable positions (along with their composition and other relevant physical characteristics). For example, a reaction in a processor may be specified by the sequence: metering one or more new micro-droplets from one or more reagent reservoirs, mixing two or more micro-droplets to form a single micro-droplet with a desired composition, and reacting the mixed micro-droplet while it resides at a stable position (by optionally exciting with heat or radiation). More formally, operation of a processor may be described in terms of a sequence of processor configurations, wherein a configuration of each micro-droplet in the processor stably resides at a known stable position. The transition from one configuration to a following configuration occurs upon performing (in parallel) one or more micro-droplet operations that create or move (or combine, or mix, or so forth) certain droplets between certain stable positions and leave other droplets motionless at other stable positions. A reaction described in terms of configurations begins with a processor in an initial configuration having reagents loaded into their initial chambers. Next, intermediate configurations result from micro-droplet manipulations (performed by sub-assembly operation) that lead ultimately to, for example, a micro-droplet with the composition necessary for the intended reaction located at a stable reaction position. In a final configuration, the intended reaction has taken place in this micro-droplet, and its results have been (optionally) sensed.

In certain embodiments, while control may be more simply described as a sequence of stable configurations, it may be more efficient to cause the motion (or other manipulation) of particular micro-droplets as soon as possible, instead of waiting for the proper configuration to be realized. Then, although each micro-droplet will still occupy successively the stable positions indicated by the sequence of stable configurations, there may be no single time at which all the micro-droplets in the device will assume a particular stable configuration. Such control is referred to herein as parallel or pipelined and may be realized as a particular implementation of the intended sequence of stable configurations.

Thus, microfluidic-processor operation may be preferably described, specified, and controlled (also referred to herein as "programmed") either as a sequence of micro-droplet configurations, with transitions between configurations resulting from higher-level micro-droplet operations, or alternatively, as the sequence of these higher-level micro-droplet operations. Such programming is advantageous because processor operations are in terms intuitively familiar from the chemistry laboratory, where reagents are measured, mixed, heated, measured, and so forth. Such programming is additionally advantageous because it accommodates microfluidic processors implemented in different technologies. The details of actual processor control, which are dependent on the actual types of independently-controllable physical elements available in a particular technology and implementation, are largely hidden from a micro-droplet or configuration level program, and appear only in relation to details of actually performing the higher-level micro-droplet manipulations and operations. For each higher-level micro-droplet operation, a sequence or package of lower-level device-dependent operations may be provided to perform the higher level operation.

For example, although sub-assemblies for performing various micro-droplet functions are expected to be present in microfluidic processors of a range of technologies, the implementation of the sub-assemblies in terms of component actuators is likely to vary with the implementation technology. Further, it is even more likely that the independently-controllable physical elements from which actuators are composed will vary greatly with technology. Therefore, a micro-droplet or configuration level program may be executed in terms of sub-assembly functions with little or no consideration of the technology details of sub-assemblies implementation. These details may be packaged into technology-dependent "subroutines" for execution by the sub-assemblies. For example, moving a micro-droplet between two stable positions in a microfluidic device, a typical higher-level operation, occurs when the provided sequence of lower-level operations is carried out on the specified physical elements of the microfluidic processor as a result of the signal generated by the control systems of the present invention.

Consequently, by controlling at the level of micro-droplets and processor configurations, the preferred hierarchical and modular construction of micro-fluidic processors may be advantageously reflected in the control systems and methods of this invention. Preferred control system hardware and software method structures are described in more detail in the following.

Hardware Structure

Control systems of the present invention generate electrical and/or optic signals in order to control microfluidic processors. Preferred processors are electrically (or electro-optically) controllable by direct application of electrical control signals to processor contacts. Where a processor also utilizes mechanical (for example, robotic), pneumatic, hydraulic or other non-electro-optic control means, these means are presumed to be also electrically controllable so that such processors are at least indirectly controllable electrically.

Preferred control system hardware is programmable so that it may control a variety of processes in a variety of processors. Thus, this hardware includes one or more programmable components, for example, a PC-type computer, an embedded microprocessor, or the like, capable of receiving and processing a software program describing processor configurations or micro-droplet operations. The programmable components in turn control peripheral interface circuitry that actually generates the control signals applied to a particular microfluidic processor, and (optionally) receives monitoring or sense signals generated from the processor. The peripheral interface circuitry is optional if the programmable components are capable of directly generating control signals.

A control system may either permanently store necessary software program, or one or more of these programs may be loaded into the control system as needed. Accordingly, the methods of the present invention are preferably implemented as software programs that cause the programmable system components, by means of the peripheral interface circuitry, to generate control signals and to receive monitoring signals from a controlled microfluidic processor, in particular from the individually-controllable components provided by the implementing technology of the controlled microfluidic processor.

Software Structure

The software of the present invention implements methods that accept a micro-droplet or processor-configuration level program describing a process and generates necessary control signals to cause a microfluidic processor to carry out the described process. In a less preferred embodiment, such programs may be constructed directly from commands controlling the independently-controllable physical elements necessary to achieve the program-specified micro-droplet functions. In more preferred embodiments, the software has a functional structure that parallels the modular structure of preferred microfluidic processors, and is constructed from commands controlling the sub-assembly operations that implement the program-specified micro-droplet functions (such programs are also referred to herein as "sub-assembly" programs). In additional more preferred embodiments, the methods of this invention, given a micro-droplet or processor-configuration level program and a description of a particular microfluidic processor, select the proper sub-assemblies of the given processor and the sub-assembly commands necessary to achieve each program-specified micro-droplet operation.

Further, in the more preferred embodiments, then, the methods of the invention generate control signals that carry out each sub-assembly operation in a sequence of specified sub-assembly operations in a manner consistent with the modular structure of a microfluidic processor being controlled. Since each sub-assembly is generally composed of actuators (possibly along with the independently-controllable physical elements), operation of a sub-assembly is preferably generated as a series of commands for causing the component actuators to function as the sub-assembly. Further, since each actuator is generally composed of independently-controllable physical elements (possibly along with other actuators), operation of an actuator is preferably generated as a series of commands for causing the component physical elements to function as the actuator. It is these latter commands that are the electrical (and/or optical) control signals that actually cause action of the controllable physical elements. In summary, control signals for selected individually-controllable device-level components are generated to cause these components to function together as selected actuators, and the selected actuators to function together as chosen sub-assemblies, and the sub-assemblies to perform the input micro-droplet program.

The description herein is directed to method reflecting microfluidic processors having the preferred modularity including sub-assemblies, actuators, and the independently-controllable physical elements. However, it will be readily apparent to those of skill in the art how to adapt these methods of processors having other modularities. It will be also apparent that the substantially same micro-droplet program (or sub-assembly program) may be carried out on microfluidic processors of different technologies simply by changing those software components that generate the device-level control signals from the micro-droplet level operations, that is the components generating actuator commands and control signals for the independently-controllable physical elements.

Preferably, a microfluidic processor also generates monitoring and sensing signals that reflect progress of processor operations, and the control systems and methods receive and use the monitoring signals to guide program execution. In one use, these signals provide feedback that monitors the operation of physical components, actuators, and sub-assemblies so that the next operation is initiated only after successful completion of previous operations. In another use, sensing signals provide indications of intermediary results obtained during a process, reaction, or analysis so that further steps may be appropriately chosen.

In more detail, the micro-droplet, processor configuration, or sub-assembly programs supplied by a user to cause a microfluidic processor to perform an intended process, reaction, or analysis, are at least lists of micro-droplet operations, processor configurations, or sub-assembly commands. Preferably, they also include commands for testing and branching based on the results of prior operations or reactions. The testing and branching advantageously are constructed to utilize monitoring and sensing signals, preferably in a modular fashion. For example, while no single value of a single physical monitoring signal provided by a processor reflects correct operation of an actuator, a combination of monitoring signals or of a single monitoring signal at different times may provide such an indication. Preferably, such a combination is made available as a single actuator monitoring signal of program variable. Similarly, a single sub-assembly (or micro-droplet or processor configuration) monitoring signal or variable may be provided from a combination of actuator and other physical monitoring signals. With such "higher-level" signals or variables, program tests and branches may depend directly on micro-droplet information. It is further preferable for the methods of this invention to include functions for converting, compiling, interpreting, or otherwise transform, input programs into forms for causing the programmable control systems acting through the peripheral control circuitry to generate the requested hierarchically structured or constrained control signals for the microfluidic processor.

Software implementing the methods of this invention, along with attendant data, may be expressed in many suitable programming languages and software engineering paradigms. On one hand, the methods of the present invention may wait to translate user-provided, micro-droplet, configuration, or sub-assembly programs into requests to the independently-controllable physical elements until actual operation of the controlled microfluidic processor. For example, component, actuator, and sub-assembly control functions may be implemented as objects in an object-oriented programming system (using an object-oriented language such as C++). Here, the control functions are object methods and are executed in sequence in response to method message exchanged during operation. Similarly, the methods may be implemented as an interpretive system which also invokes functions only during operation. On the other hand, these methods may translate programs during an initial compilation step. For example, the control functions of the various levels may be implemented as macros (using a procedural language with a macro facility such as C) in a procedural paradigm, which translate each sub-assembly command into a corresponding plurality of actuator commands, so that programs are translated into instructions for the programmable apparatus. Mixed implementations are possible. For example, control functions can be represented as library routines, or higher-level functions may be objects and lower-level functions may be macros.

Data for the methods of the present invention includes, for example, the current configuration of the microfluidic processor and the current state of the actuators and components in the processor. These data can (including micro-droplet changes between successive configurations) be represented in manners advantageously suited to use by micro-droplet control functions.

5.1.3. General Purpose Processors and Systems

The control systems and methods of the present invention additionally have various implementations, some more special purpose and others more general purpose, that are described with reference to FIG. 14.

FIG. 14 illustrates exemplary levels of detail according to which microfluidic processes may be specified for use by the methods of this invention and according to which the previously-described structural and functional elements may be assembled into implementations for carrying out these process specifications. Most specifically, the inputs and outputs of this invention's control systems and methods are control/monitoring signals 215 that are directly exchanged with a microfluidic processor to cause it to perform particular functions. A program specified at this level is little more than a sequence of signals 215 to apply to various processor contacts for various durations, and would have substantially no flexibility. It could be used only to perform a single process with processors of a single design. A system for such a special-purpose program would need to be little more than a hardware controller, perhaps not even programmable, that generates the specified signals in the specified sequence. Virtually no software functionality would be needed.

Most embodiments of the present invention, however, include at least a programmable control system and software functions that can translate operation commands for a processor's independently-controllable physical elements 211 into physical control/monitoring signals 215. This translation may require an amount of processor description information (control configuration information) 213 primarily directed to determining, for example, which processor contacts relate or external control elements relate to which physical elements. A program specified at this level would include a list of physical elements to control for which durations and at which times. However, such a program would not be limited to a single processor type, but could control a limited selection of microfluidic processors all having the same complement and arrangement of physical elements but with different arrangements of contacts and other external control elements. The different external control arrangements would be described by specifying different processor description information (control configuration information) 213.

Preferably, however, embodiments of the present invention have control systems and software functions that can accept a program described by lists of sub-assembly operations 205, each of which act directly on one or more micro-droplets present in a microfluidic processor, and generate the necessary comments to physical elements 211 and the consequent control/monitoring signals 215. Optionally, a sub-assembly program may also include tests concerning the success of previous operations or the nature of intermediate products and perform conditional branching based on such tests. To generate physical element operations, the software and methods would make use of two additional information sources. First, using technology library 209, the software would determine the sequence of actuator commands (and direct physical element commands) that implement each sub-assembly operation. Second, using processor description information (actuator configuration information) 207, the software would find the sequence of physical element commands that implement each actuator operation. Physical element operations 211 result from combining this additional information with the sub-assembly program; and control/monitoring signals 215 result from the physical element operations as described.

Preferred embodiments of this nature have advantageous general purpose functionality of at least the following types. For example, if a user of the present invention wishes to perform a particular process expressed as a particular sub-assembly operation program, the present invention may offer a choice of microfluidic processors suitable for performing the process. By combining the program with descriptions 207 and 213 of different processors along with the technology libraries appropriate to these processors, the software methods can determine for which processors physical element operations 211 and control/monitoring signals 215 may be successfully generated. It is these processors that are capable of performing the intended process, and that may be offered to the user. Further, a user may select a particular processor with accompanying processor descriptions and technology library, and the software methods may combine this information with various programs to provide the user with a choice of processes that the selected processor may perform. In summary, the systems and methods of this embodiment may offer users choices of several processing programs that may be performed by a selected microfluidic processor, or choices of several processors that may perform a selected processing program.

One of skill in the art will appreciate various alternatives. For example, the processor descriptions may be packaged together in a single data grouping or file. In a further example, the performance relationship between processors and sub-assembly operation programs may be determined initially, and the results stored as a separate data area that is consulted to provide user choices.

Further, preferred embodiments may accept more general program specifications in terms only of micro-droplet operations 201. Such programs would specify only that certain micro-droplets are to be metered, mixed, reacted, tested, and so forth, without specifying which sub-assemblies are to perform these operations. In these embodiments, the software methods would access processor description information (sub-assembly control configuration information) 203, which describes a processor's sub-assemblies and their configuration, in order to determine (if possible) a sequence of sub-assembly operations 205 that will perform the specified micro-droplet operations on a particular processor. Control/monitoring signals may then be generated from these sub-assembly operations as described above. These embodiments have the additional general purpose functionality of allowing a user either to choose among micro-fluidic processors suitable for performing a selected micro-droplet program or to choose among micro-droplet programs that a selected processor is capable of performing.

In summary, in preferred embodiments, the control systems and methods of this invention allow a single microfluidic processor to perform multiple programs specified at various levels of generality, and also allow a single program to be performed on multiple processors. User interfaces may present a user with these choices. In these preferred embodiments, this general purpose function may be implemented by separately storing program specifications and processor descriptions, and upon execution, combining the program and the processor description to generate actual control/monitoring signals. In other implementations, this information may be predetermined. For example, the systems may store the same program in different forms for different microfluidic processors, and present to the user a choice of the available, stored programs for the possible processors.

5.2. A "Thermally-Controlled" Embodiment

In a preferred thermally-controlled embodiment, controlled microfluidic processors are implemented in a thermally-controlled technology and are physically standardized, also as described. Although the following description is largely limited to this more preferred embodiment, one of skill in the art will readily appreciate how to generalize the preferred embodiments described for the control of general microfluidic processors of other technologies, and also of general digital microfluidic devices. Therefore, in this more preferred embodiment, the control systems of the present invention generate electrical (and optical) signals for controlling the individually-controllable device-level components of preferred thermally-controlled microfluidic processors.

5.2.1. Preferred Micro-Fluidic Processors

Preferred microfluidic processors primarily use thermally-controlled actuators with optical signals for monitoring or detection. In particular they are constructed according to a technology that uses local resistive heating or Peltier-device cooling for control functions. For example, a thermally-controlled processor can be maintained at baseline temperature by a temperature-controlled heat sink or a cooling element, such as a Peltier device, with actuators controlled by localized heating above the baseline. Localized heating may preferably be provided by low power resistive heaters of less than approximately 1 to 2 W, advantageously controlled by low voltages, for example, less than 50, 25, 15 or 10 V.

Mechanical force, where needed for control purposes, may be provided by gas pressure generated by localized heating applied to a gas reservoir within a processor. For example, controlled gas pressure may be directly used to cause micro-droplet motion. Controlled gas pressure may also be used to control micro-valves by causing an obstructing element to move into and close a passage, while return to normal pressure may draw the obstructing element back and open the passage. In a preferred embodiment, the obstructing element may be a low melting point solid, which is melted for valve operation also by localized heating. Thermally-controlled micro-valves may act to admit externally provided relative pressure or relative vacuum into a processor for powering more complex actuators. Thermally-controlled mechanical force may also be generated by other means, such as by other heat-sensitive fluids, by differentially expandable materials, and so forth. Additionally, localized heating and cooling may be directly applied to micro-droplets for reaction control. Further, electrical signals may be used for actuator control in other manners, such as attractive or repulsive magnetic or electric forces.

In this embodiment, device monitoring signals are derived primarily from temperature sensitive elements mounted in the device, which preferably generate electrical monitoring signals such as, for example, temperature-sensitive resistive or semiconductor elements. Localized heating may be precisely controlled by sensed temperatures. Gas pressures may then be controlled by controlled localized heating. Local thermal capacity may be monitored by a combination of a temperature sensor with a small heater by measuring temperature responses with respect to a determined quantity of heat. Using local thermal capacity sensors, micro-droplet presence or absence may be sensed because a micro-droplet has a higher thermal capacity than an otherwise empty passage. Other electrical monitoring signals may be generated by, for example, detecting local electrical impedance, which may provide alternative means for detecting micro-droplet presence. Micro-sensors with deformable conductive elements may provide for direct detection of local pressures.

Optical signals may be used in preferred microfluidic processors where advantageous. For example, scattered radiation may provide the simplest means of detecting or observing reaction or analysis results. Incident radiation may be helpful to initiate or stimulate a reaction or analysis. Also, micro-droplet position sensors may be optically based.

Figure 1:
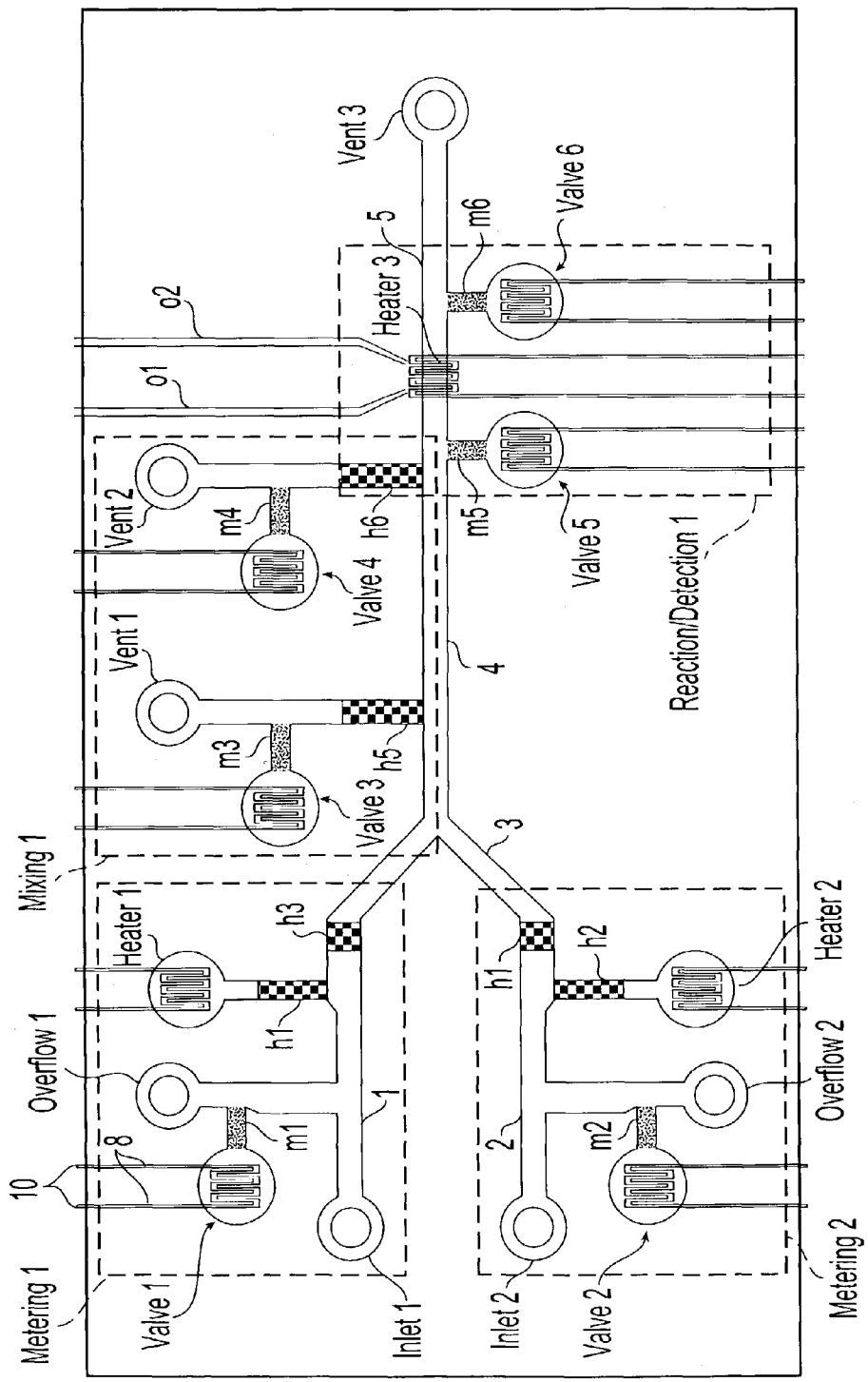
FIG. 1 illustrates an exemplary microfluidic device thermally controlled in a preferred manner.

In more detail, FIG. 1 illustrates, schematically and not to scale, an exemplary integrated microfluidic processor constructed in the preferred modular and hierarchical manner in an embodiment of the preferred thermal-control technology. This integrated microfluidic processor is designed to perform a sample analysis through the following steps: meter predetermined micro-droplets from two sources, for example, a source of the sample and a source of analysis reagents; mix the metered micro-droplets to form a third homogeneous micro-droplet; perform a temperature-controlled analysis reaction in the third micro-droplet; and finally, optically monitor the analysis results.

This exemplary microfluidic processor is constructed from three types of sub-assemblies, each sub-assembly being constructed from three types of actuators, and each actuator being constructed from one type of controllable device-level component. The processor also contains passive components such as passages, reservoirs, ports, outlets, optic conductors, and so forth. In particular, this processor has four separate sub-assemblies: two micro-droplet metering sub-assemblies, metering1 and metering2; one mixing sub-assembly, mixing 1; and one reaction/detection sub-assembly; referenced reaction/detection1. These sub-assemblies are constructed from three controllable heater actuators, six controllable valve actuators, and one optical detector, all interconnected with passive inlets, overflows, vents, and reservoirs. The sub-assemblies have the following components: sub-assembly metering1 includes inlet1, overflow1, valve1, heater1, and passage 1; sub-assembly metering2 includes inlet2, overflow2, valve2, heater2, and passage 2; sub-assembly mixing1 includes heater1 (and optionally heater2), valve3, valve4, vent1, vent2, Y-shaped passage 3 and passage 4; and sub-assembly reaction/detection1 includes valves5, valve6, heater3, and passage 5. Here, heater1 and heater2 are included in both the mixing and in the metering sub-assemblies. Also, heater1, valve3, valve4, vent1, vent2, and passages 1 and 4 alone may form a micro-droplet motion sub-assembly. Lastly, in addition to passive passages, the processor is constructed from only one type of controllable device-level components, localized resistive heaters. Preferably, resistive heaters are operatively coupled to resistive temperature detectors that provide feedback information.

Before a description of sub-assembly operation, exemplary passage configurations for creating and defining stable positions are described. Generally, stable positions are created by hydrophobic regions, or by the relative arrangement of main passages and vented side passages. (Main passages are continuing passages along which micro-droplets are manipulated; side passages are dead-end passages branching from the main passages.) First, hydrophobic regions, for example regions h1-h6 of FIG. 1, are limited regions whose interiors have been treated to assume a hydrophobic character, whereas the remainder of the passage interiors have a hydrophilic, or at least a wettable character (either normally or by treatment). Because of surface tension effects in micro-droplets, predominantly aqueous micro-droplets will travel in the hydrophilic regions of passages with smaller hindrance than when they travel in the hydrophobic regions. In effect, therefore, a barrier exists at junctions between hydrophilic and hydrophobic regions: the hydrophilic regions "attract" aqueous micro-droplets, while the hydrophobic regions "repel" such micro-droplets. Thus, these hydrophobic-hydrophilic junctions define relatively stable positions that a micro-droplet requires extra force to traverse. Because of the "repulsive" effects of the hydrophobic entrance regions h1, h2, h5, and h6 of the passages to heater1, heater2, vent1, and vent2 in FIG. 1, in comparison with the "attractive" effects of the substantially hydrophilic interiors of adjacent passages 1, 2, and 4, aqueous micro-droplets are restrained from penetrating into these hydrophobically-"protected" passages. Similarly, extra force is required to cause aqueous micro-droplets to pass the hydrophobically-protected regions h3 and h4, which therefore define stable regions between main passages 1-2 and Y-shaped main passage 3. In the case of predominantly hydrophobic micro-droplets, the hydrophobic and hydrophilic passage characteristics are reversed.

The present invention includes other methods of creating stable positions that will be apparent to one of skill in the art in view of the present description. For example, by placing a controllable vent adjacent to a passage with a valve, a stable position may be created when the valve is closed and the vent is open.

Because the effect of gravitational forces is negligible at the spatial dimensions used in these devices, surface tension may be exploited by designing local passage size differences within the device, perhaps in conjunction with adjacent hydrophobic regions. For example, since a narrowed passage will draw fluid from a larger passage by the capillary effects of surface tension, a relatively stable position can be created where a relatively narrow passage joins a relatively wider passage. This stable position may be reinforced by the presence of an adjacent hydrophobic region.

Stable positions can also be created by a local configuration of passages, preferably where a hydrophobically-protected side passage is vented to the exterior branches from a main passage. For example in FIG. 1, if a micro-droplet is being moved along passage 4 toward vent 3 by pressure applied to its left surface, and if valve3 is closed while valve4 is open, then the micro-droplet will come to reside at the stable position in passage 5 just beyond the entrance to the side passage leading to vent2. The micro-droplet will not penetrate the side passage to vent2 because of hydrophobic region h6, and it will not pass into passage 5 because all applied pressure will be released through vent2 to the exterior. Therefore this position, just beyond the side passage to vent2, is a stable position if valve3 and valve4 are properly actuated. (If valve4 is closed, the micro-droplet will continue moving through passage 5.) In this manner valved and vented side passages with hydrophobically-protected entrances also define stable positions.

In summary, hydrophobic regions h3 and h4 create adjacent stable positions in passages 1 and 2, respectively. Side passages to vent1 and vent2, hydrophobically-protected by regions h5 and h6, respectively, define stable regions adjacent and to the right of their junctions with passage 4.

Now turning to actuator and then to sub-assembly operations, micro-valve actuators, for example, valve1-valve6, preferably use meltable elements, for example, m1-m6, respectively, to reversibly obstruct, under the control of gas pressure, their respective controlled passages. For simplicity of illustration only, micro-valves are schematically illustrated in FIG. 1 as having only one heater element, whereas, in a preferred subsequently-described embodiment (FIGS. 6A-B), they usually have three separate heaters and one temperature sensor (also up to three temperature sensors). Heater1 and heater2, which heat their respectively gas reservoirs, form thermally-controlled gas pressure generator actuators, which are part of micro-droplet motion and formation sub-assemblies. Heater3, which heats passage 5, provides for thermal control of reactions in micro-droplets present in this passage. Results of reactions completed in passage 5 are detected in this exemplary microfluidic processor by an optical actuator, namely input optic conductor o1, which conducts incident radiation to the reaction region, and output optic conductor o2, which conducts scattered and emitted radiation from the sample for analysis. The incident radiation may be in the IR, visible, or UV bands as required for a particular application. Other detection means can be employed in other applications.

Operations of the sub-assemblies result from the coordinated operations of their component actuators. First, two micro-droplet motion actuators move micro-droplets along passages 1 and 2 by means of gas pressures generated by pressure generators controlled by heater1 and heater2, respectively. Next, sub-assembly metering1, which is composed of actuators valve1, heater1, inlet1, overflow1, and passage 1, meters a micro-droplet of determined volume from an aliquot of fluid introduced through port inlet1 in the following manner. Initially, if not already open, valve3 and valve1 are opened so that the side passage to vent1 is not blocked. Next, fluid introduced into inlet1, for example, by an external manual or robotic device, and flows up to the stable position created by the first hydrophobic region h3 just beyond the widening of passage 1, with any excess fluid flowing out through port overflow1. Region h1 prevents the introduced fluid from entering the side passage to heater1. Finally, controlled gas pressure generated by heater1 pinches the micro-droplet from the introduced fluid that lies between the junction of the side passage to heater1 and region h3, and propels it to just beyond the junction with the side passage to vent1. Region h5 prevents the micro-droplet from entering the side passage to vent1, and vent1 allows the propelling gas pressure to escape. Sub-assembly metering2 is constructed and operates similarly. (Optionally, valves, not illustrated, may be present adjacent to inlet1 and inlet2 in order to prevent passages 1 and 2 to refill after droplet metering.)

Sub-assembly mixing1 mixes two micro-droplets of differing constituents, which have been adjacently positioned at the stable position created by the junction of main passage 4 and the side passage to vent1, in the following manner. First, valve3 (and valve1 and valve2) are closed so that the adjacently situated micro-droplets in passage 4 can be propelled toward passage 5. Next, gas pressure is generated by heater1, or by heater2, or by both, so that the two micro-droplets in passage 4 are moved to the stable position just beyond the junction of the side passage to vent2. Importantly, the generated pressure is controlled so that the motion is sufficiently rapid to mix the micro-droplets. Finally, the remaining sub-assembly illustrated in FIG. 1, sub-assembly reaction/detection1, which includes valve5, valve6, heater2, o1, o2, and passage 5, operates as follows. After a mixed micro-droplet of the correct composition is positioned in passage 5, this passage is sealed by closing valve5 and valve6. Next, heater3 is controlled to stimulate a reaction in the trapped micro-droplet, and the results of the stimulated reaction are optically detected by radiation conducted by o1 and o2.

FIG. 1 also illustrates leads and external connectors for the electrical and optical signals. For example, control and monitoring leads 8 for valve1 are schematically illustrated as two leads extending from the valve to the microfluidic processor's edge terminating in connectors 10. (A full and complete illustration of a micro-valve preferably has four, or six or more signal leads.) Although leads 8 are illustrated here as substantially straight, in most microfluidic processors with more actuators and leads, leads bend to avoid obstacles and other leads, or are combined where control requirements allow, or crossover each other separated by insulating films. The terminating connectors are preferably standardized, for example, as an array of pins that may be accommodated by an external socket, or, illustrated here, as rounded protrusions along processor edges that may be accepted by mating contacts in a receptacle in a control system. Also, exemplary optic conductors o1 and o2 are illustrated as extending substantially straight from the reaction/detection sub-assembly to optical couplings or connectors 7, also preferably standardized for routine connection to external radiation sources and detectors. Also, these conductors may need to bend or cross over obstacles. Optical conductors may comprise light pipes, optical fibers, or other means for spatial transmission of an optical signal.

According to a preferred embodiment of the invention, the number of terminating connectors required for the control of a plurality of actuators may be reduced by arranging/sharing, in the form of an array, the contact wiring to each actuator. The resulting compression of the number of terminating connectors advantageously simplifies communication with the entire microfluidic processor. Whereas each actuator requires two leads to complete an electrical circuit, according to a conventional arrangement of leads and contacts, a device comprising N actuators comprises 2N leads and 2N terminal contacts. By configuring the contact wiring in an array, however, the number of required terminal connectors can be reduced to as few as $2\sqrt{N}$. For example, in a hypothetical device comprising 100 actuators, the number of external contacts can be reduced from 200 to 20. This greatly simplifies external wiring and device control.

As stated above, the compression is accomplished by arranging the contacts in an array. According to this arrangement, electrical contacts for the N actuators are configured in R rows and C columns such that the product RC=N, preferably where R is approximately equal to C, and most preferably where R=C. With this arrangement, actuators located in a given row share a common electrical contact. Similarly, actuators arranged in a given column also share a contact. Each actuator has a unique address, though, given by its unique row/column combination. Therefore, each actuator is individually actuatable by supplying electric current to the appropriate row-column combination.

It is also preferable that microfluidic processors for control by the present invention be physically standardized so that microfluidic processors designed for different reactions or analyses may be controlled by a single external control systems. Standardization would, for example, limit a microfluidic processor to only a few selected sizes. Electrical and optical connectors would be limited to standard forms, positions, and alignments. Inlet ports, overflow ports, vents, and so forth would be limited to standard forms and locations (for easy robotic access). A further preferable feature of microfluidic processors that promotes standardization is a self-description function. A processor may be described by providing its controllable and passive components, their mutual relations and interconnections, and, for each controllable component, the identity of the connectors for its control and monitoring signals. This self-descriptive information may be used by the control methods and systems to generate correct control signals at correct connectors for a particular microfluidic processor, otherwise such self-descriptive information must be explicitly entered by a user or "hard-coded" into the methods. This function may be variously implemented. For example, all the self-descriptive information may be stored in the microfluidic processors; alternatively, a processor may store a key to a database of this self-descriptive information which is stored elsewhere.

Further description of the construction and functioning of preferred microfluidic processors are provided in U.S. Pat. No. 6,048,734 dated Apr. 11, 2000; U.S. Pat. No. 6,057,149 dated May 2, 2000; U.S. Pat. No. 6,130,098 dated Oct. 10, 2000; U.S. Pat. No. 6,271,021 B1 dated Aug. 7, 2001; and U.S. Pat. No. 6,379,929 B1 dated Apr. 30, 2002. These patents are incorporated herein in their entireties by reference for all purposes without any admission that they are prior art to the inventions claimed herein. General knowledge and information concerning micro-fabrication techniques available in the art may be found in Rai-Choudhury, ed., 2000, *MEMS & MOEMS: technology and applications*, SPIE—The International Society for Optical Engineering, Bellingham, Wash.; and in Rai-Choudhury, ed., 1997, *Handbook of microlithography, micromachining, and microfabrication—volumes* 1 & 2, The Institution of Electrical Engineers, London, U.K., both of which are incorporated herein in their entireties by reference for all purposes.

5.2.2. Control Methods

This sub-section describes preferred structures for the control signal generation functions along with preferred structures for their data and parameters, both for a thermally-controlled microfluidic processor of the preferred implementation. The following descriptions apply to any implementation paradigm: for implementation with objects, the object hierarchy is described; for procedural implementation with macros, the macro inclusion hierarchy is described; for procedural implementation with library routines, the procedure invocation hierarchy is described. One of skill in the art will be readily able to apply the following description to the chosen paradigm. Also, although the following describes a currently preferred allocation of functions to hierarchical levels, the methods of this invention are readily adaptable to other function allocations, and even to other function definitions. In particular, the grouping of components into actuators may be implementation- and technology-dependent. Also, there may be fewer functional levels, for example, just sub-assembly and actuator levels, or more functional levels, where advantageous.

Preferred Functional Structures

Figure 2:
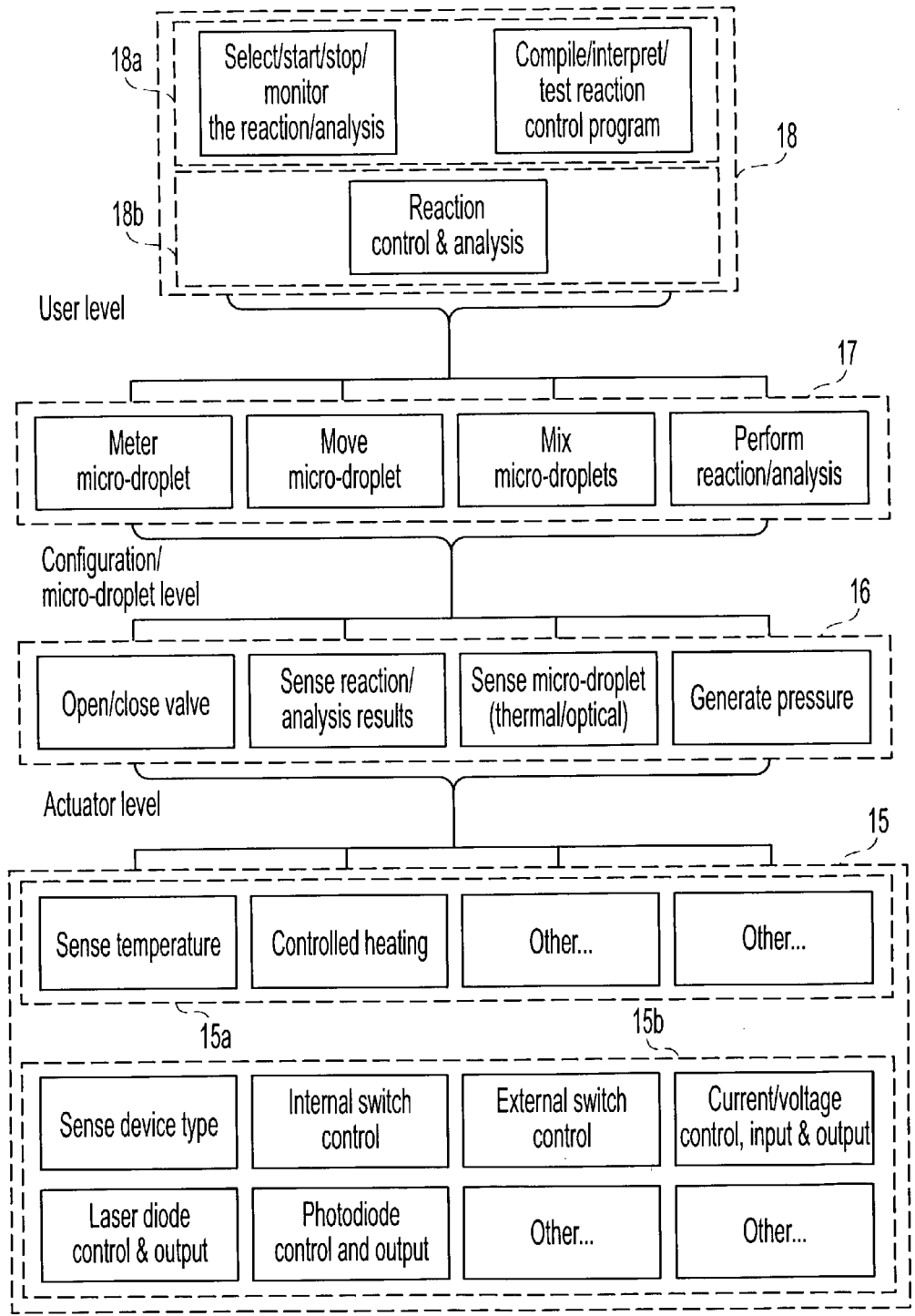
FIG. 2 illustrates a functional hierarchy of the present invention.

FIG. 2 illustrates an exemplary and non-limiting, but preferred, hierarchical organization of signal generation functions for a thermally-controlled microfluidic processor implemented in a preferred technology. This figure illustrates four function levels, a component level, an actuator level, a sub-assembly (which is functionally identified in FIG. 2 as a configuration or micro-droplet level), and a user level. Since higher-level functions act only by invoking lower-level functions, they necessarily abide not only by their own constraints but also by the constraints of all lower-level functions. As described, this insures that processor control signals ultimately generated abide by the entire preferred hierarchical structure and constraints.

First, the lowest-level functions are component-level functions 15b, which are preferably the only functions that directly cause generation of electrical and optical signals for control of the individually-controllable microfluidic processor components. For example, the "current/voltage control" primitive function causes the control system to generate or monitor specified electrical control signals. The "external switch control" function causes the control system to switch these signal generators to signal connectors. (The "internal switch control" function controls switches internal to a microfluidic processor, which, if present, route electrical control signals from processor to connectors to internal components.) Therefore, the joint action of these two functions generates and monitors electrical control signals between the control system and electrically-controlled processor components. Correct connectors for component control of particular components may be determined from the previously-described self-descriptive microfluidic processor data, which includes such connector-component information. In the case of preferred self-descriptive microfluidic processors, this self-descriptive information, or a key to it, can be obtained from the microfluidic processor itself. The function reading this information from a processor is called the "sense device type" function. Finally, the functions "laser diode control" and "photodiode control" provide similar control of optical signals.

Level 15 may also include certain additional simple functions 15a, which implement actions somewhat more complex than the actions of atomically implementable device components, but which are nevertheless simple and best classified as components rather than as actuators. Functions 15a may invoke functions 15b or other functions 15a. An example of such a generalized component-level function is the "sense temperature" function, which outputs the temperature at a given sensor element. Given a specified (resistive) temperature monitor element, its external contacts may be indicated by descriptive microfluidic processor data. The electrical output of these indicated contacts may then be monitored by the "current/voltage control" and "external switch control" functions, and then converted to a temperature in view of known physical properties of the given sensor. The "controlled heating" may apply, using the more primitive control and switch functions, a given power to a given heater element, or may adjust the applied power in view of the output of a "sense temperature" function to achieve a given temperature.

These component-level functions and their suggested implementations are not intended to be limiting. First, other and additional component-level functions may be defined; the listed functions are exemplary and not exhaustive. Second, since component-level functions are typically determined by the implementation technologies, they typically will differ for microfluidic processors of different technology. Even within a single technology, details of heating, sensing, and so forth differ in different specific microfluidic processor implementations. Further, even for a single processor type, different preferred embodiments may package the primitive and generalized component-level functions differently.

Actuator-level 16 includes functions that control groups of one or more usually interconnected components in a manner and sequence so that they function together to achieve a particular actuator-type function. Actuator-type functions are those typically associated with the "plumbing" or "machinery" necessary to implement a chemical reaction, such as opening or closing a micro-valve in the microfluidic processor, generating pressure, sensing quantities, and so forth. For example, a "sense reaction results" function may be optically implemented. It may act by means of the "laser diode control" and the "photodiode control" functions, first, to cause the proper incident radiation to be provided to the proper external optical connectors in order that reaction results are illuminated, and second, to cause scattered or emitted radiation to be observed. A "sense micro-droplet" function may sense the presence or absence of a micro-droplet by, in effect, measuring a local thermal capacity. Thus, this actuator function may, first, provide a given quantity of heat by means of the "controlled heating" function, and second, determine the temperature response by means of the "sense temperature" function. A greater temperature increase indicates a lower heat capacity indicative of the absence of a micro-droplet, and vice versa. This function may also be optically implemented to determine micro-droplet presence or absence in a region by sensing optical properties of the region in a manner similar to the "sense reaction results" function. A "generate pressure" function may use the "controlled heating" function at a given power or to a given temperature in order to heat gas in a reservoir to increased pressure. Generated pressure may be monitored with a pressure sensor if available in the microfluidic processor. Finally, the important "open/close" valve functions are described subsequently.

Information describing an actuator's individual components and interconnection indexed by an actuator identifier may be available from self-descriptive processor data. In this case, simply an actuator identifier may be specified to the actuator functions, which then automatically determine component parts from the self-descriptive processor data without requiring user attention or input of this information. In turn, component information, for example, connector identification, may be automatically determined by component-level functions from this same data.

Actuator-type functions are expected to be more standardized than component-level functions because they reflect facilities needed by virtually all microfluidic reaction processors. For example, virtually all microfluidic processors will have micro-valves with open and close valve functions. Nevertheless, the actuator-level functions and their suggested implementations described herein are exemplary, and not exhaustive or intended to be limiting. For example, certain component-level functions, especially generalized functions 15a, may be considered actuator functions in different implementations. Second, even though many of these types of actuator functions may be substantially similar in different processors, their implementation may differ from those suggested above depending on the processor components available in the implementation technology. Third, different actuator functions may be present to take advantage of different component types present on different processors, for example, a wider range of sensing actuators may be present to take advantage of a broader sensing technology.

Configuration/micro-droplet 17 functions (performed, generally, by sub-assemblies) are those that act on micro-droplets, preferably invoking primarily actuator functions 16 so that micro-droplets move from stable position to stable position. Therefore, the configuration/micro-droplet 17 functions provide that the microfluidic processor progresses through configurations that are defined by the micro-droplets present in a processor and their stable positions. In other words, a micro-droplet function starts with one or more micro-droplets at stable positions and invokes actuator functions so that upon completion the one or more micro-droplets are again at different stable positions. These functions do not complete with micro-droplets at unstable positions, positions from which a micro-droplet may spontaneously move and in an indeterminate manner. Micro-droplets at unstable positions would therefore make predictable and orderly operation of a microfluidic processor impossible, and this situation is to be avoided.

Input information for micro-droplet functions includes positions of the micro-droplets to be acted on. Preferably, this information may be obtained from an initial processor configuration, which is updated with new micro-droplet positions, to a final configuration upon function termination. Also where sense actuators are present, these functions may check micro-droplet position and report an error if the measured position and intended position are inconsistent. Even more preferably, using micro-droplet position and processor self-descriptive data, these functions automatically determine which actuators to invoke for achieving the intended result. Otherwise, micro-droplet position, and possibly also the correct actuators, must be determined by a user (assuming prior micro-droplet operations were successful) and then input to these functions.

Micro-droplet-level functions are preferably provided to correspond to standard types of chemistry laboratory operations, such as measuring, mixing, heating, and so forth. Thus, functions 17 usually include: functions to meter a micro-droplet from a fluid source in order to form a new micro-droplet of known volume, to move a micro-droplet from one stable position to another stable position, to mix an inhomogeneous micro-droplet to form a homogeneous micro-droplet, to perform a reaction by thermal or other type of excitation, and so forth.

Because microfluidic processors of this invention act in a digital manner by manipulating micro-droplets to perform chemical or biological analysis, basic micro-droplet function types are largely "microfluidic processor independent." Certain micro-droplet functions, for example, separation of micro-droplet constituents, may be added where required by a certain type of reaction. Alternatively, certain combinations of basic micro-droplet functions may be made available as a single function for efficiency. Variation in function details and function implementation may occur between different technologies and processor types. Preferred implementations of these functions for preferred processors are subsequently described.

User-level 18 functions do the work useful to an end user, performing and monitoring an intended reaction or analysis in a microfluidic processor. Functions 18a, "protocol/compiler/interpreter" functions, direct a microfluidic processor to actually carry out an intended reaction. These key functions interpret, convert, compile, or otherwise process a user-provided reaction program, preferably specified substantially as a sequence of micro-droplet-level functions that prepare a micro-droplet containing the necessary reactants, cause the intended reaction to occur in this prepared micro-droplet, and then detect or sense reaction results. As described, reactions are preferably "programmed" largely by invoking micro-droplet-level functions, and rely on the function hierarchy of this invention to ultimately generate the necessary control signals on the correct connectors to cause a microfluidic processor to perform the invoked functions. Because micro-droplet functions, as well as actuator and component function, encapsulate most details of processor actuator operation, users may advantageously specify reactions in terms corresponding to routine chemical laboratory operations. Self-descriptive microfluidic processor data permits this specification without attention to internal processor details.

User-level 18 may also contain operator-type functions 18b, which provide for microfluidic processor control by permitting the selection of the reaction or analysis "program" to be performed by a microfluidic processor, by initiating the selected reaction "program" after readying the processor, and by terminating the reaction and returning the sensed reaction results, and so forth. Operator function may also provide for monitoring a microfluidic processor as it processes a reaction. For example, monitoring functions may show on an appropriate display device a graphical (or otherwise formatted) portrayal of the current state of a microfluidic processor such as the current position of micro-droplets, the current state of microfluidic processor actuators and components, and so forth, along with indications of the "program" steps already performed and yet to be performed. Optionally, operator-type functions may include program development and debugging tools, for example, tools for entering micro-droplet function commands, for "single-stepping" a processor through a program, and for further facilities familiar from programming environments for computer systems.

Since a function of a particular hierarchical level performs its actions by making requests of functions, the exchange of requests is fundamental and is variously referred to herein. For example, a higher-level function may generate, or send, or transmit, or so forth a request, which a lower-level function then processes, or accepts, or receives, or so forth. Alternatively, a higher-level function may provide a request to a lower-level function.

Preferred Data Structures

The hierarchically arranged signal-generating functions preferably utilize and maintain certain data, for example, self-descriptive data for the microfluidic processor, data descriptive of the current processor state, and the configuration or state of micro-droplets present in the processor. Self-descriptive data for a microfluidic processor generally specifies the processor's components, how they are interconnected, and by what external contacts they are controlled. For example, processor components may be described as a list of atomic components, their type, properties, and where controllable, control connectors. Actuators may be also described as a list of their type, properties, and atomic components out of which they are constructed. The external contacts controlling the components of an actuator can be determined from the component of the actuator and the connectors controlling these components. Component interconnection may be described by a list of the passages, hydrophobic regions, inlet ports, outlet ports, vents, and so forth, along with indications of the connectivity of these elements, which may be represented as a network flow diagram.

The self-descriptive processor data may be automatically supplied, preferably by the microfluidic processor, or less preferably by the control system or by both acting in combination. In one embodiment, a ROM-type memory (or EPROM, or other permanent or quasi-permanent memory) is embedded in or on a microfluidic processor containing at least this processor-descriptive data. Alternatively, this memory can be limited to a few (10) bytes that store only key-type information for lookup in a control system database retrieving complete self-descriptive data. In another embodiment, machine-readable indicia, such as a bar code, or human-readable indicia, such as a serial number, may be provided on a microfluidic processor. The "sense device type" component function obtains this self-descriptive data either by accessing the embedded microfluidic processor memory by means of standardized connectors (for example connections "1, 2, 3, and 4" on all microfluidic processors), or by reading machine-readable indicia, or by manual input of human-readable indicia.

Self-descriptive microfluidic processor data preferably permits simplified parameterization of the component and actuator-level functions by the symbolically identified components and actuators. For example, a "controlled heating" function may be applied to "heater-6B", wherein "heater-6B" is identified by the functions in the self-descriptive data. In contrast, applying a "controlled heating" function to external contacts 39, 42, 43, and 68 is less flexible. An "open/close valve" function may be more preferably applied to "valve-12", instead of to "valve-12"'s components or to their connectors. Information describing a microfluidic processor also preferably includes the state of the symbolically-identified components and actuators. For example, the current temperature, or the past heating of "heater-6B" is 80 C; valve-12" is currently "open"; and so forth.

Function data further includes micro-droplet configuration or "state" data, which includes a list of the micro-droplets currently present in a microfluidic processor and their composition and current position. Micro-droplet composition may, for example, be recorded by the source or sources from which the micro-droplet was created. Micro-droplet position records its current unstable position occurring only transiently during transitions between configurations. Micro-droplets may be symbolically specified in the configuration, for example, the sixth micro-droplet created being "micro-droplet-6," and micro-droplet functions may then be applied to symbolically specified micro-droplets. For example, when the "move micro-droplet" function is applied to "micro-droplet-6" the function determines this micro-droplet's current position from the current processor configuration. From this determined position, the "move micro-droplet" function next determines from the self-descriptive processor data the correct actuators to invoke to move "micro-droplet-6," and from current state information, the current state of these actuators. When the determined actuators are invoked their components, their component's connectors, and their component's state are similarly determined. Alternatively, in simpler but less preferred embodiments, the actuators, components, and connectors may be pre-specified.

Finally, user-level operator monitoring and display functions may display this function data. For example, animation of microfluidic processor operation may be displayed as a map of the microfluidic processor components and their connections along with the current position of the micro-droplet and the current component's activation. Limited aspects of the current state may also be operator-selected for display.

In one embodiment of the present invention, a microfluidic processor may be represented in an object-oriented programming paradigm. In an exemplary object representation, where some or all of the components, actuators, micro-droplets, and so forth may be represented as objects, the maintained data would be represented as object instance data, defining for each object its type, state, geometric relation to other objects, and so forth. The control functions would be methods manipulating the component, actuator, and micro-droplet objects. These microfluidic processor control functions may be represented in other programming paradigms where the maintained data may be represented as lists, tables, trees, or other known data structures.

5.2.3. Control Systems

A control system of the present invention preferably has a distributed and hierarchical structure, generally paralleling the hierarchical control function structure illustrated in FIG. 2. Preferably, lowest-level control functions, such as component-level functions 15 and actuator-level functions 16, are implemented in system interface hardware configured for direct connection to a controlled microfluidic processor (for example, data acquisition and control board 26 in FIG. 3A), while highest-level functions, user-level functions 18, especially operator functions 18b, are implemented in system user hardware configured for user interaction (for example, personal computer 27 in FIG. 3A). Intermediate function levels, reaction control 18a level, micro-droplet level 17 (or configuration level), and actuator level 16 may be implemented in the interface or in the user hardware, or in an intermediary hardware level, as convenient. (Micro-droplet level 17 functions are those functions performed by the physical sub-assemblies described above, which in turn are composed of actuators and perhaps individual components.)

Control systems, and especially system interface hardware, may be implemented with electronic microprocessor, such as those available from Intel, Motorola or other electronic suppliers. To avoid confusion, such control system electronic processors will be always called "microprocessors," while microfluidic processors will be called both "microfluidic processors" and simply "processors."

FIG. 3A illustrates an exemplary preferred two-level control. Microfluidic processor 20 is illustrated as having a standardized physical configuration including a standardized size, shape, and electrical and optical connectors 21, which are arranged along three edges of the rectangular processor. The processor is shown being inserted into (or removed from) an interface hardware receptacle having electrical and optical connectors 25 standardized to mate with contacts 21 of the processor. Most connectors are for electrical signals, while certain are for optical signals (IR, visible, UV) in the case of optically monitored or excited microfluidic processors. Further, exemplary microfluidic processor 20 is illustrated with three inlet ports 22 for accepting fluid reagents or samples. Preferably, these inlet ports are in standard position on the processor so that laboratory robot 24, where available, may be easily programmed for automatic loading of ports of several types of microfluidic processors. Otherwise, the ports should be accessible for manual loading. Where possible, reagents may also be pre-packaged on a microfluidic processor. Additionally, processor 20 has micro-circuit 23 accessible through certain standard connectors for storing at least self-descriptive processor information. Alternately, processor 20 may bear indicia, such as a bar code, indicating device type or further information.

Illustrated first-level, interface hardware comprises data acquisition ("DAQ") board 26 directly connected to microfluidic processor 20. A preferred DAQ board is programmable, for example including an embedded microprocessor (such as those produced by Intel, Motorola, etc.) with RAM memory (for example, 1-8 MB), which controls electrical and optical sensor/driver circuits and switches between outputs of these circuits and connectors 25. The sensor/driver circuits are switched among connectors 25 under microprocessor control to provide control signals to the microfluidic processor, or to receive monitoring signals. Optical signaling components, for example laser diode radiation sources and photodiode radiation detectors, are similarly controlled by the microprocessor. The DAQ board also preferably includes a standardized external interface that permits links to a broad range of higher-level portions of the control system. Illustrated here is generic 5-wire, bi-directional, serial interface 28, similar to such standard interfaces as UART, USB, Firewire, Ethernet, and so forth, all of which may be used in this invention. In other embodiments, the DAQ board can be configured to plug into the busses of higher-level control systems. User hardware preferably communicates with a DAQ by means of message exchange according to a standard protocol.

A DAQ board with sufficient microprocessor and memory resources may perform virtually all control functions. For example, such a board may perform component-level functions 15, actuator-level functions 16, micro-droplet-level functions 17, and reaction-control function 18a. In this preferred embodiment, only the user interface functions are more efficiently performed on user hardware. Such a capable DAQ board would function with most user hardware of limited resources. With a less capable DAQ-board, control functions may be advantageously shifted to user hardware, starting with higher-level reaction control functions and proceeding lower in the function hierarchy. In the former case, limited monitoring messages would need to be exchanged between the DAQ board and the user hardware; in the latter case, user hardware would send parameterized messages to the DAQ board invoking lower-level functions. These messages may be divided into packets for actual transfer across the DAQ interface, and the transfer may be error checked.

In alternative embodiments, certain lowest-level control functions may be offloaded from the DAQ board onto control hardware embedded in processor 20 itself, for example, onto micro-circuit 23. For example, this circuit could serve as an internal switch so that a smaller number of external contacts 21 may be switched among a larger number of control or monitoring leads on the processor, thus conserving external contacts. Other certain component control functions may be offloaded to the microfluidic processor.

User hardware (also called herein a "host") is the top-level of the control systems of this invention. In most embodiments user hardware performs at least user interface functions 18b in FIG. 2. In response to user input, these top-level functions have final control of starting, monitoring, and stopping a reaction on a processor, and of reporting reaction results. The user hardware, or host, further may perform administrative functions, among which may be managing the software instructions and data for itself and for attached DAQ boards. Software instructions for causing the host to perform its functions may be loaded from computer-readable media, such as optical disk 29, or may be downloaded from network interconnection 30. Data may also be loaded to the host computer from computer readable media, in particular a database of microfluidic processor descriptive data may be loaded into the host. Further, the host may "download" software instructions and data to the DAQ board, where such is not already resident by being stored in, for example, a ROM/Flash memory card or a small hard disk. This downloaded software and data loaded causes the DAQ board to perform its assigned tasks. User hardware is preferably programmable, for example, with microprocessor, memory, and storage, and connects to a controlled DAQ board by means of the standardized interface on the DAQ board.

The hierarchical control systems of this invention—the user hardware, the DAQ board and, optionally, the microfluidic processor itself—may conveniently be constructed to a number of different design points suitable for different applications. As illustrated in FIG. 3A, user hardware 27 may be a laptop PC, typically with a microprocessor of 500 Mhz or greater speed, with 64 MB or more of memory, and connected to stand-alone DAQ board 26 by bi-directional UART 28 which plugs into the PC. This implementation is suitable for portable medium-throughput applications or for light in-laboratory use.

A still more portable design point is a handheld analysis system, in which host 27 may be a palmtop or other type of handheld type computer, DAQ board 26 plugs into an "expansion" socket or other receptacle or plug on the handheld host, and microfluidic processor 20 in turn plugs into a DAQ board receptacle. The handheld may also include remote communication interfaces, such as wireless access. This design point would have medical applications in a doctor's office, or at bedside, or in an emergency situation, or so forth. It may also have industrial applications for the "field" of manufacturing processes of industrial chemicals. Other applications will be readily apparent to those of skill in the art.

Another design point is a less portable, but higher throughput laboratory analysis system in which host 27 may be any PC-type or workstation-type laboratory computer and one or more DAQ boards 26 with microfluidic processors 20 arranged in a number of appropriate configurations. In a simple arrangement, the DAQ board may reside in a tabletop holder (not illustrated) which connects to host 27 via data cable 28. Alternatively, multiple microfluidic processors 20 with their associated DAQ boards may reside in a single holder, or multiple holders, and may be connected to host 27 by a network connections such as Ethernet connections. For more complete laboratory automation, one or more processors 20 with their associated DAQ boards may be arranged so that samples or reactants may be introduced into the processors by one or more standard laboratory robots. In FIG. 3A this is illustrated by laboratory robot 24 which has access to inlet ports 22 of microfluidic processor 20. This laboratory robot is controlled via cable 31 from host 27 so that microfluidic processor loading and processor operation can be conveniently and automatically controlled from a single computer. Alternatively, the robot may be controlled by a separate computer.

A broad range of further design points that are suitable for various other applications will be apparent to those of skill in the art.

5.2.4. DAQ Board Architecture

The DAQ board of this embodiment is relatively more capable, and therefore may be interfaced to user equipment, or hosts, of a wide range of capabilities. DAQ board architecture includes both a preferred hardware architecture and a preferred system software architecture, described herein.

Hardware Architecture

FIG. 3B illustrates a preferred hardware architecture for DAQ boards of this embodiment. First, DAQ boards have one or more receptacles, slots, sockets, or so forth where one or more replaceable microfluidic processors may be accommodated in a firmly supporting manner with good contact to its external connectors. Microfluidic processors, are preferably mounted on a relatively tough substrate, for example a PCB board. Processor substrates are standardized to have one, or at most a few, selected shapes, sizes, and connector arrangements for easy replacement in one, or at most a few, corresponding DAQ board receptacle types. Thus, FIG. 3B illustrates microfluidic processor 37 mounted on substrate 36.

Standardized electrical connectors 38a connect between both electrical control lines 39 and lines on substrate 36 leading to microfluidic processor 37, and also between electrical monitoring lines 40 and corresponding substrate lines. Optical connectors 38b connect between both optical conductors 42 from DAQ board light sources and optical conductors 41 to DAQ board light sensors and corresponding optical conductors on processor substrate 36 also leading to the microfluidic processor. The electrical connectors, which may have many embodiments, are illustrated here as edge connectors that are engaged when the processor substrate is inserted in a DAQ board receptacle. Alternatively, connectors may be suitable for engaging a flexible ribbon cable, or may by multi-pin sockets, or so forth. The optical connectors may be of types known for connecting fiber-optic cables.

Host computer interface 44 is preferably selected according to the type of host used in a particular control system. For example, for handheld hosts the DAQ board may plug into an available slot or interface integrated into the handheld device. For laboratory systems using PC or workstation type hosts, the DAQ board provides a modular, simple, and preferably standardized connector and interface, for example, suitable for a USB, or a Firewire, or an Ethernet cable connection. Illustrated in FIG. 3B is a simple, bi-directional, UART serial interface with cable connector 38c. The illustrated interface has serial data-in and data-out lines and a reset line, which should be capable of bringing the DAQ board to a known state. This interface also provides power and ground lines.

The DAQ board is preferably externally powered by a host computer (or by a standalone holder). Power may be supplied at standard voltages, for example, at +12 V, +5 V, or other voltage, which the board itself converts to and regulates at required internal voltages. Preferably, a DAQ board is able to negotiate with host (or with its holder) concerning the power requirements of the board and an attached microfluidic processor, and to generate an error indication if the power supply does not meet requirements. Similar power negotiations are known from USB interfaces employed in personal computers.

FIG. 3B generally illustrates a preferred microprocessor-based DAQ board architecture. Microprocessor and memory 43 (such as RAM or ROM) communicate with both host interface controller 44 and with internal bus controller 45 over a microprocessor bus optimized for high speed communication with a few devices. Internal bus 46 is typically different from the microprocessor bus because it is designed and optimized for controlling and monitoring interfaces to numerous, lower-speed peripheral circuit controllers. Internal bus controller 45 links the microprocessor bus bi-directionally with the internal bus. Alternatively, the microprocessor bus may directly connect to peripheral circuit controllers, and the internal bus may be eliminated. Although not illustrated, the DAQ board may also include one or more hard disks of small form factor, readers for flash devices, RAM, or other interfaces.

In an economical embodiment, the signal generation and sensing function includes peripheral circuitry in which a smaller number of bus-controlled signal generation and monitoring circuits are switched (or multiplexed) by bus-controlled signal switching circuits among a larger number Of leads or lines for connection to a microfluidic processor. Thus, the microprocessor controls microfluidic processor control-signals by controlling the signal generation and signal switching circuits by means of the internal bus 46. Alternatively, a driver/sensor circuit may be provided for each external connector, and the signal switches may be eliminated.

Accordingly, FIG. 3B illustrates heater driver 47 circuit, controlled by bus 46, with relatively few output leads being switched or routed by analog switch 48, also controlled by bus 46, among relatively more numerous control lines 39. The heater driver circuits may control heater elements on the microfluidic processor by providing either a source of constant voltage or current, or a source of pulses of controlled width or frequency, or of sources of signals of other modulation schemes. Heater elements should be controllable from zero power up to a maximum power, where the maximum is preferably from 1.0 to 2.0 W, and more preferably from 0.5 to 2.5 W. Microfluidic processors also typically have at least one cooling device, for example a Peltier device, which is used to establish a baseline operating temperature appropriate to the reaction or analysis being performed, for example, a room temperature of approximately 25° C. or lower. DAQ boards, therefore, also include peripheral circuitry, controllable by the microprocessor for controlling such a cooling device.

Similarly, monitoring signals generated in a microfluidic processor and conducted on relatively more numerous monitoring lines 40 are switched by switch 50, under control of bus 46, to one of relatively fewer number of digital sensor circuits 49, which may be an analog-to-digital converter or similar. Also, the sensor circuits may also provide signals to activate sensors where needed. The digitized monitoring signals are then transmitted to microprocessor and memory 43 over internal bus 46. Monitoring signals are typically generated by temperature detectors, preferably at least one detector accompanying and for control of each resistive heater. Temperature detectors are preferably resistive temperature detectors (preferably of platinum) with resistance in the range of 1000Ω to 4000Ω at 25° C. Since temperature measurements preferably have an accuracy and resolution of approximately 0.5° C., temperature sensor circuitry should be able to measure a resistance (for platinum temperature detectors) in the above range with an accuracy and resolution of better than approximately 0.25%, and more preferably better than approximately 0.13%.

Similar switch-based control may be used for optical signals. FIG. 3B illustrates bus-controlled analog switch 54 which switches a bus-provided control signal to relatively numerous laser diodes and drivers 53. Laser diode output is then conducted by light conductors 42 to substrate 36, and then to microfluidic processor 37. To provide excitation light to a microfluidic processor, a DAQ board has at least one, and preferably two or more, laser diodes (or other controllable light sources) with a power range of 1-10 mW and with wavelengths useful for reaction excitation and detection. Preferably, a plurality of laser diodes are provided with a plurality of wavelengths specific to plurality of different microfluidic processors performing a plurality of different reactions or analyses. Further, the laser diodes, or their optic conductors, may optionally be provided with optic elements, such as filters or polarizers. Driver circuits for the laser diodes are preferably controllable (by the microprocessor) so that laser diode output power can be adjusted over their range.

Optical monitoring signals are received over light conductors 41 and are sensed by photodiodes 51 (or other light sensors). The digitized photodiode output is switched onto the bus by switches 52. To monitor light returned from a microfluidic processor, a DAQ board preferably has one or more photodiodes, preferably four, or five, or more photodiodes with characteristics, such as wavelength responsiveness, dark current, quantum efficiency, and so forth, specific to the reactions or analysis. Preferably, a plurality of photodiodes are provided with a variety of characteristics specific to a variety of microfluidic processors performing a variety of reactions or analyses. Further, the photodiodes, or the optic conductors, may optionally be provided with optic elements, such as spectral filters, to adapt their responsiveness to the reaction. Photodiode digitization circuits preferably have adjustable gains and ranges to accommodate photodiodes of different characteristics.

Alternatively, where controllable optical switches are economically available, this architecture illustrated may be replaced by a switched architecture similar to that for electrical signal generation and monitoring, namely fewer optical sources and sensors optically switched among more numerous optical conductors.

FIG. 3B is intended to illustrate, not limit, the preferred DAQ board architecture. First, this architecture is easily scalable. Since microfluidic processors typically have numerous electrically driven heaters and electrical sensors many of which may operate in parallel, a DAQ board preferably has capability to simultaneously drive at least two heaters and to simultaneously sense at least two monitoring leads by, for example, having two or more analog switch/driver or analog switch/sensor pairs. Although simultaneous generation and monitoring of more than one optical signal is usually not required, this capability may be provided if necessary as in the case of electrical signals. Second, DAQ boards may be based on other types of programmable devices and may have other arrangement of components for generating control signals and sensing monitoring signals that will be apparent to one of skill in the art in view of the above description. For example, the internal bus may be eliminated in favor of direct communication between the microprocessor and the signal generation/monitoring elements. Also, one or more switches may be eliminated in favor of an increased number of signal generation or sensing circuits. Finally, a single DAQ board may have receptacles and peripheral circuitry for controlling more than one microfluidic processor.

Software Architecture

Software instruction executed by microprocessor 43 (or other programmable control element) controls the DAQ board. In particular, responses to host messages and control signal generation are enabled according to the hierarchical microfluidic processor control functions. Although allocation of control system function among a host, a DAQ board, and a microfluidic processor is flexible, preferably, as described, the DAQ board performs most of the control functions in order that the microfluidic processor need provide only self-identification and in order that the user equipment need only provide an operator interface. Thereby, microfluidic processor cost is reduced, and the user equipment is freed from real-time microfluidic processor control.

A preferred software architecture is layered as is known in the art. At the lowest layer is an "operating system", which preferably provides, for example, standard software process control, communication, memory allocation, and access for control of DAQ-board peripheral circuitry. Software process and memory control preferably provides real-time, asynchronous control with interfaces for standard languages, such as C or C++. Drivers for peripheral circuitry preferably provide asynchronous control over the electrical and optical signals output to a microfluidic processor and asynchronous sensing of monitoring signals from a controlled microfluidic processor. Such a system may be built, for example, from a minimal Linux kernel augmented with peripheral circuitry drivers.

In a software process-based method implementation, the operating system executes software processes managing, for example, microfluidic processor control functions, host communication, and internal DAQ board administrative functions. Host communication software processes preferably implement a layered communication protocols. At a network layer, communication is preferably packet based with error checking (for example, by a checksum with retransmission of lost or corrupt packets). At a physical layer, the protocol may be implemented over host communication link, such as the illustrated serial link from host interface 44, Ethernet, or so forth with provision for negotiation of transmission rates, packet sizes, and so forth. Exemplary protocols may be selected from the IP family, such as SLIP or TCP, or from other known protocols.

Internal administrative software processes provide responses to, for example, host requests for DAQ-board status, and for the operation and status of an attached microfluidic processor. Administrative software processes may also provide for DAQ-board software update. For example, in response to a host status request, the DAQ board should report its status (e.g., free, reaction in progress, steps completed, results now available, and so forth). The DAQ board may also perform diagnostic tests of the board itself and calibrate on-board sensor circuitry. In response to a power requirements request, the DAQ board should negotiate the power it expects to draw from the host in advance (e.g. for this particular reaction in this particular microfluidic processor). In response to a software update request, the DAQ board should request or accept software (or firmware) from the host. Further internal status requests and responses may also be provided for.

Microfluidic processor control software processes perform functions that have been generally described with respect to FIG. 2 above, and will be described in more detail below for the preferred thermally-controlled microfluidic processors. In a preferred embodiment, component-level, actuator-level, micro-droplet-level, and the user-provided reaction control function are performed by DAQ board software processes. Preferably, at least, functions for drop metering and mixing, temperature cycling, and separation of micro-droplet components in a separation media are performed on a DAQ board. In a software process-based embodiment, functions for the software control processes are hierarchically structured as are the functions themselves. For example, an actuator software process sends request messages to its component-level software processes. Other control implementations will be apparent to those of skill in the art.

5.2.5. Methods and Functions

This sub-section describes control function for preferred thermally-controlled microfluidic processors, component-level functions, actuator-level functions, micro-droplet-level functions, and lastly user-level functions. This description is exemplary and not limiting. In view of the following description, one of skill in the art will understand how to construct other implementations of the described functions, and also how other possible components and actuators, which may be constructed in the preferred thermally-controlled technologies, may be controlled according to this invention.

5.2.5.1. Temperature Control Functions

Temperature sensing and controlled heating are important component-level functions for preferred thermally-controlled microfluidic processors. Temperature sensor elements are preferably resistive elements (resistive temperature detectors or "RTDs") configured to have measurable resistance changes in response to temperature changes. Such a sensor may be made of platinum with resistance in the range of approximately $100\Omega$ (Ohm) to $4000\Omega$ at $25°$ C., so that an accuracy and resolution of approximately $0.5°$ C. can be achieved with sensor circuitry capable of resistance measurements of approximately 0.17% or better accuracy and resolution.

FIG. 4A illustrates an exemplary RTD, which can operate in at least two modes. FIG. 4B illustrates a function performing the first mode of temperature measurement. The function first obtains input parameters, here principally the identity of the particular RTD in question. RTD identity may be provided, for example, as an input to a procedural function invocation, or can be a local variable in an object representing this RTD, or by other means. However provided, this identity determines the control leads (and thus the DAQ-board connectors) to be used for measurement, for example, leads 57-60 in FIG. 4A, so that the DAQ-board microprocessor can control the appropriate peripheral circuitry. Next, a small current is applied across the RTD on one pair of leads, for example, leads 57 and 60, while the resulting voltage is sensed across a second pair of leads, for example, leads 58 and 59. Finally, the resistance of the RTD is determined from the supplied current and measured voltage (or vice versa), and the temperature is then derived/calculated from the measured resistance. The applied current is chosen small enough not to generate significant local heating, but large enough to generate a voltage drop measurable at the above precision. The use of two pairs of leads improves accuracy, because, since the voltage measurement can be made with little to no current, little or no voltage drop develops in measurement leads 58 and 59; most voltage drop measured being measured across the RTD itself. Alternatively, where less accuracy is sufficient, a single pair of leads can be used for current supply and voltage measurement.

In a second mode, the RTD can sense the presence or absence of a micro-droplet by measuring a local specific heat, which is greater when a micro-droplet is present in a nearby passage than when no micro-droplet is present. This mode functions in a manner substantially similar to the first mode except that the applied current is greater and is applied for a time sufficient to generate enough heat to increase the surrounding temperature by a measurable amount, for example, by approximately, 2° to 4° C. in the absence of a micro-droplet. In the presence of a micro-droplet, the temperature increase will be less. Therefore, the presence or absence of a micro-droplet can be sensed by measuring the rate of the temperature increase.

Heaters are also preferably resistive and configured to controllably generate between 0.5 and 1.5 W of heat with a low voltage source. Since a preferred low source voltage is 5-10 V or less, the resistance of the resistive heaters is in the range of approximately 15Ω to 1000Ω at 25° C. (even smaller heaters may be needed for source voltages of less than 5 V). As FIG. 4A illustrates, a heater with a nearby RTD may provide for controlled heating.

FIG. 4C illustrates a component-level controlled heating function. Input parameters include the identity of the heater/RTD pair, so that the microprocessor via the internal bus can energize or monitor the correct leads (and thus the correct DAQ-board connectors), and a desired temperature and temperature tolerance. Using a temperature sensing function, for example, the function illustrated in FIG. 4B, the temperature at the heater is determined. The heater current is then adjusted in view of the measured temperature, the desired temperature, and the tolerance. The time delay is chosen to provide for smooth control characteristics. These control steps, especially the current adjustment step, may also implement an alternative control method, such as a PID or a fuzzy logic method, that may depend on the currently measured temperature and on one or more temperatures measured in the recent past.

A further temperature-related, component-level function provides for controlling baseline device temperature. In addition to heaters, a preferred microfluidic processor may have a Peltier (or other) cooling device (or devices) in order to generally maintain the processor at a baseline temperature, for example, at a room temperature of 25° C. Alternatively, a Peltier cooler can be mounted on the DAQ board in a manner such that it makes thermal contact with a microfluidic processor when inserted into the board. Such a cooler prevents the progressive build-up of the effects of heaters energized during the course of a reaction or analysis. A cooling device may be controlled similarly to a resistive heater by adjusting a control current to maintain a specific temperature sensor at the desired baseline temperature, where the specific sensor is mounted at a thermal distance from heaters to sense background processor temperature.

5.2.5.2. Further Component-Level Functions

A further component-level function controllably generates pressure, for example, to move micro-droplets or other materials in a microfluidic processor. This function is an important component of several higher-level actuators requiring thermally-controlled mechanical force. A preferred embodiment of a pressure generator includes a gas reservoir with a controlled heating element and a passage conducting gas pressurized by heating to its point of application. FIG. 5A illustrates a preferred embodiment with relatively larger gas reservoir 65 and relatively smaller conducting passage 66 linking to the point of pressure application in passage 68. The gas in the reservoir is preferably inert, such as nitrogen or argon, but can be air. The reservoir has controlled heater 69 (the accompanying temperature sensor is not illustrated) embedded in its base (or top). Region 67 of passage 68 has a hydrophobic surface so that any (aqueous) fluid present in passage 68 is excluded from gas reservoir 65.

FIG. 5B illustrates a component-level control function for this pressure generator. In the first step, the function obtains identification of the pressure generator and its associated heater and a parameter representing the desired pressure to be generated. In a next step, the desired pressure is converted into a desired quantity of heat needed, and in the final step, the heater is controlled (by a control signal across connectors determined from component identity) to a temperature for a time sufficient to supply the needed heat.

In addition to micro-droplet sensors depending on temperature effects described previously, further component-level functions may control other types of micro-droplet sensors present on a microfluidic processor. For example, micro-droplet sensors may be based on capacitive detection, in which an impedance between two leads is altered by the presence or absence of a micro-droplet. The DAQ board then includes switchable impedance sensing circuits. Pressure sensors may also be present and can be used as micro-droplet position sensors as explained subsequently. Pressure sensors may also provide direct feedback for use in the controllable pressure function of FIGS. 5A-B.

5.2.5.3. Micro-Valve Functions

Figure 6B:
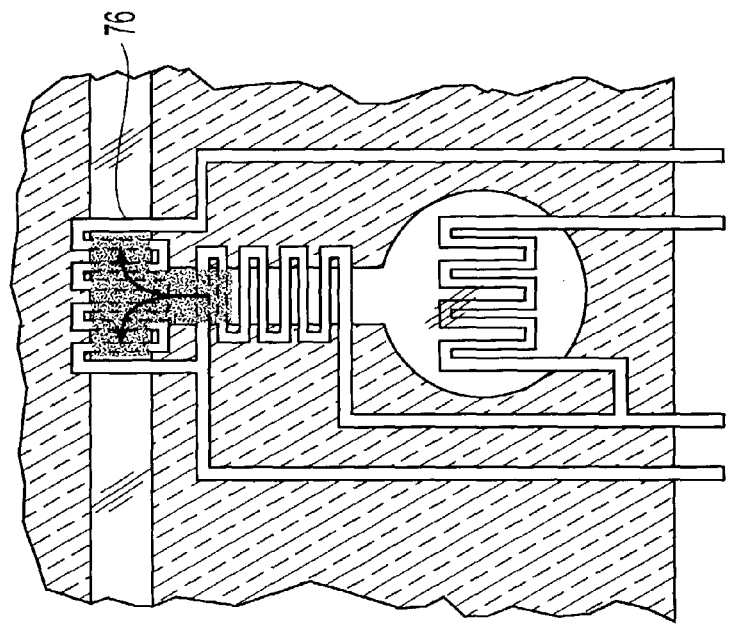
Figure 6A:
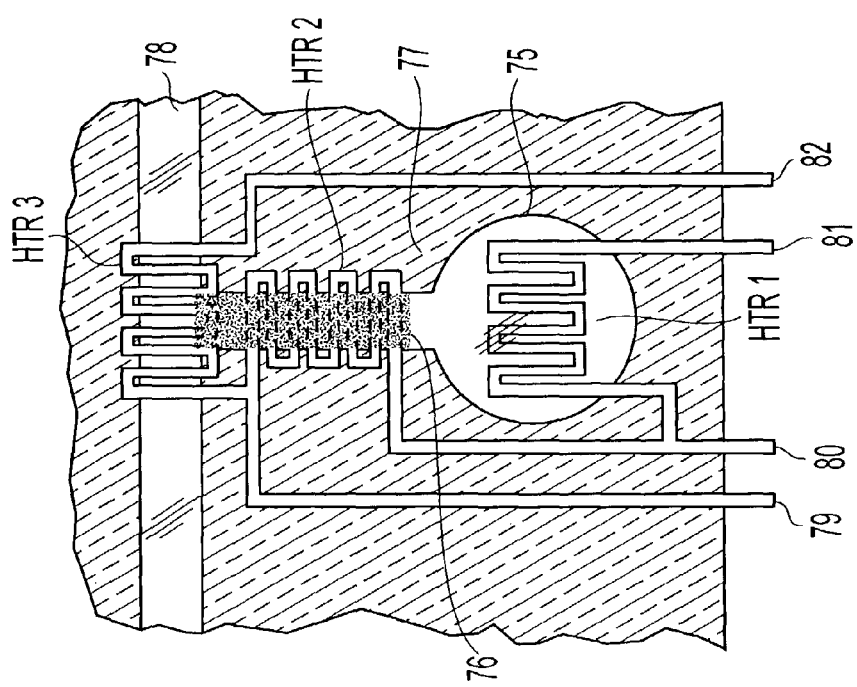

A micro-valves function is an important actuator-level function that will be present in most microfluidic processors. FIG. 6A illustrates a preferred embodiment of a micro-valve for closing and opening controlled passage 78. The micro-valve has a pressure generator, for example, including gas reservoir 75 with heater HTR1 and side passage 77 connecting with controlled passage 78. Side passage 77 is blocked by plug 76 of low melting-point, inert material. The melting point is preferably greater than the baseline operating temperature of the microfluidic processor but less than the boiling point of any micro-droplet controlled by this micro-valve in passage 78. For example, the melting point may be from 40° to 90° C., preferably from 50° to 70° C.; the material may be a wax (for example, an olefin) or a eutectic alloy (for example, a solder). The micro-valve also includes heater HTR2 for controlled heating of side passage 77, and heater HTR3 for controlled heating of controlled passage 78, as illustrated. Sensors optionally accompanying these three heaters are omitted from FIG. 6A for simplicity and without limitation.

The configuration of leads 79-82 is one arrangement that provides independent control of all three heaters with only four directly-routed and non-overlapping control leads. This illustrated arrangement is exemplary. For example, six leads, two for each heater, may be provided instead.

Figure 6C:
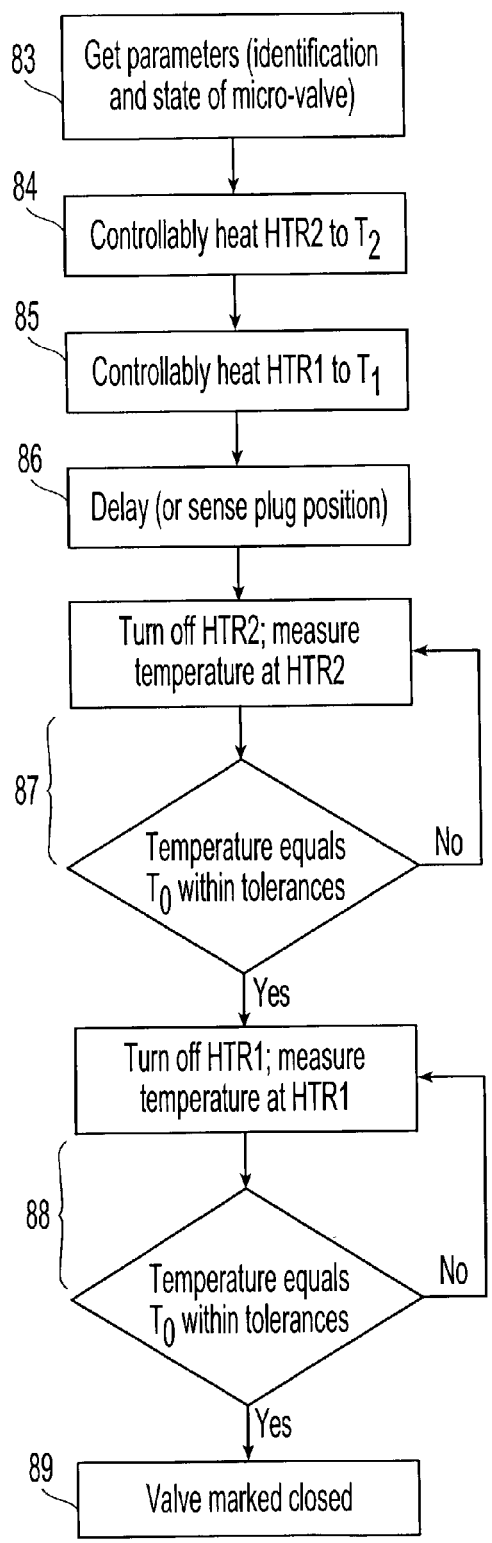

The micro-valve closing operation is described with reference to FIG. 6A, which depicts the micro-valve in an opened state, FIG. 6B, which depicts the micro-valve in a closed state, and FIG. 6C, which depicts the steps of the micro-valve close function. The close function first obtains input parameters 83, which identify the particular micro-valve to be closed, its component heaters, and the connectors for the heater control leads and for monitoring signals from any optional sensors. The input parameters also includes the current micro-valve state, which must be "open" for the micro-valve close function. (If the micro-valve is already closed, the close function may simply exit). Next, step 84 controllably heats HTR2 (by activating leads 79 and 80) and side passage 77 to a temperature T2 slightly, but sufficiently, above (for example, 1° to 5° C. above) the melting temperature of plug 76 so that the plug melts. After or simultaneous with plug melting, step 85 controllably heats HTR1 (by activating leads 80 and 81) to a temperature T1 and for a time so that sufficient gas pressure is generated to move the melted plug from passage 77 into controlled passage 78. Preferably, T1>T2. This pressure is maintained for a time delay 86 determined to be sufficient for the plug to move into passage 78. Alternatively, where a position sensor for the plug is available (for example, a thermal sensor in association with HTR3), the delay lasts until sufficient movement of the plug is sensed.

Step 87 then deactivates HTR2 and waits until its temperature returns within tolerances to T0, the baseline processor temperature, so that the plug solidifies again. The return to baseline temperature may either be sensed by a sensor or may be assumed after sufficient time delay. After the plug is solidified, step 88 similarly returns the temperature of HTR1 and gas reservoir 75 to baseline. Because the volume of the gas is now greater because of the motion of the plug out of passage 77, a relatively lower gas pressure is present in reservoir 75 at the baseline temperature when the micro-valve is closed than when it is open.

The micro-valve is now closed because controlled passage 78 is blocked with the solidified plug. Step 89 marks the state of the micro-valve as closed in the data describing current microfluidic processor configuration.

Figure 6D:
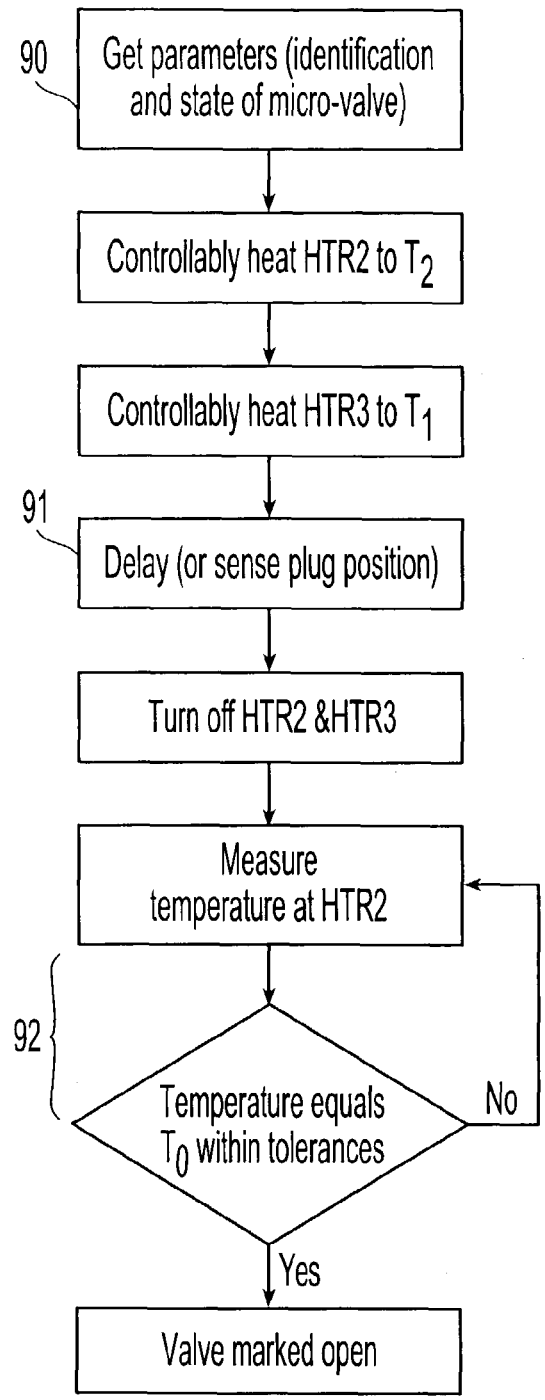

The micro-valve opening operation is described with reference to FIG. 6B, which depicts the micro-valve in a closed state, FIG. 6A, which depicts the micro-valve in an opened state, and FIG. 6D, which depicts the steps of the micro-valve open function. As customary, this function first obtains 90 input parameters. These parameters identify the control and monitoring connectors and indicate a closed state (otherwise, the function simply exits). First, the function controllably heats HTR2 and side passage 77 to temperature T2 and HTR3 and controlled passage 78 to temperature T1. T1 and T2 are both above the melting point of the plug, as described above. Plug 76 in controlled passage 78 thereby melts, and, under the influence of the relatively lower pressure in gas reservoir 75 remaining from the micro-valve closing, is drawn back into side passage 77. These heaters are activated for a time delay 91 determined to be sufficient for the plug to move back into side passage 77. Alternatively, where a position sensor for the plug is available (for example, a thermal sensor in association with HTR2), the delay is until movement of the plug is sensed. Finally, heaters HTR2 and HTR3 are deactivated, and step 92 waits until the temperature in the vicinity of the side passage heater has returned to within tolerances to baseline (either by temperature monitoring or by time delay). Finally, the micro-valve state is marked as closed with the plug now solidified in side passage 77 and controlled passage 78 unblocked.

In the following descriptions, for ease of illustration and without limitation, micro-valves are schematically represented with a single heater and a single pair of leads, instead of their full illustration, as in FIGS. 6A-B, with three heaters and at least four leads.

5.2.5.4. Optical Detection Function

Optical sensing of the results of microfluidic processor reactions or analyses is preferred because it may be easily performed externally to a microfluidic-processor without any physical removal of reaction results from these passages. Alternatively, where a microfluidic processor includes a separation facility for reaction results, detection of components separated thereby is also preferably by optical means. Optical sensing may depend on scattered incident radiation or generated fluorescent radiation, or so forth. The invention also provides for the excitation of a reaction or analysis by radiation.

Basic optical detection components and control functions are illustrated with reference to FIGS. 11A-B. FIG. 11A illustrates limited section 165 of a microfluidic processor with exemplary components for optic sensing of micro-droplet md1, which is illustrated as stably positioned adjacent to hydrophobic region h1 of main passage 167. Optic components include radiation conductor 166 for conducting incident radiation (for example, from a DAQ-board laser diode) to md1, and radiation conductor 169 for conducting radiation from micro-droplet 1 for analysis (for example, to a DAQ-board photodiode). Radiation conducted from md1 may be scattered radiation, fluorescent radiation, or so forth. Lens 168 schematically illustrates elements for radiation gathering or focusing, filtering wavelengths, or so forth, present on the processor. Also, a reflector may be placed adjacent to the main passage to double the radiation path through the micro-droplet being sensed. Such a reflector may optionally have wavelength-dependent properties, being, for example, an interference filter or a dichroic mirror.

Limited portion 165 could be a substantially vertical depiction, illustrating substantially vertically arranged optic conductors out of the plane of the microfluidic processor and passing illumination through the thickness of the processor. This portion could also be a substantially horizontal depiction, illustrating substantially horizontally arranged optic conductors in the plane of the microfluidic processor and passing illumination through only one passage of the processor. Further, the optic conductors may run substantially in the plane of the processor (horizontally), only to angle to a final orientation near their target.

FIG. 11B illustrates an actuator-level, optical-sensing function. This function begins by obtaining parameters 170 that identify the particular optical-sensing actuator, so that the DAQ-board microprocessor may control those radiation generation and detection components that connect to the correct connectors for the identified detection optical sensor. Next, the input radiation conductor is illuminated 171, and the resulting radiation is sensed 172.

Other such entirely external detection methods, based on externally-applied magnetic (NMR) or electric fields, or on a combination of these fields with optical detection, can also be preferably used in the microfluidic processors of this invention. In this case, field generation components must be placed on a microfluidic processor or on the DAQ board (or on a DAQ-board housing), must be identified to the control function, and must be activated by the control function.

5.2.5.5. Micro-Droplet Move Function

A micro-droplet move function is an important configuration-level function that will be present in most microfluidic processors. This function moves a micro-droplet from a first position to a second position, thereby advancing the microfluidic processor from a first configuration to a second configuration in which the micro-droplet moved is in its second position. This, and other micro-droplet-level functions, act most reliably when the initial and final micro-droplet positions are stable. They are preferably only invoked or only act when the data describing the current processor configuration indicates that micro-droplets are correctly positioned at a stable position. As described, a stable position can be established by, for example, a hydrophobic region in a passage, or by a local configuration of passages.

Micro-droplet motion of course requires mechanical force and generally, in preferred microfluidic processors, this mechanical force is gas pressure-generated by a pressure generator actuator. Micro-droplet motion may be stopped when the motion pressure is dissipated by, for example, a vent to the processor exterior. Motion may also be stopped by a hydrophobic region which requires more motive force than is being supplied (coupled with deactivating the pressure generator actuator).

Micro-droplet motion is illustrated with reference to FIG. 7A, depicting micro-droplet 95 in initial position 96, FIG. 7B, depicting micro-droplet 95 in final position 97, and to FIG. 7C, depicting the steps of the micro-droplet-motion function. Micro-valves in these figures (and subsequently) are schematically represented with only a single heater. Step 100 of the move function customarily obtains parameters identifying the components of the sub-assembly for moving micro-droplet 95, here, valve1, valve2, and HTR1, their spatial relationship, and their control leads or external connectors. In the exemplary configuration illustrated, initial micro-droplet position 96 is just beyond the side passage to vent1, a stable position after a prior movement with valve1 open, leaving vent1 accessible from main passage 98 to dissipate any driving pressure. Alternatively (not illustrated), the initial stable position may be defined by a hydrophobic region in passage 98, and valve1, vent1, and their connecting side passage may be absent from the microfluidic processor. Micro-droplet 95 is determined from the input configuration data to be correctly in an initial stable position 96, because the known, current, microfluidic-processor configuration records the position of all micro-droplets present in the processor. If there is no micro-droplet at position 96, there is nothing for this function to do, and it exits. Preferably, the present motion function is called by a higher-level function only when micro-droplet 95 is in position 96 as a result of prior functions.

Next, step 101 prepares the micro-valves for micro-droplet motion by invoking the actuator-level micro-valve functions to close valve1 (if present and previously open, as determined by its state in the microfluidic processor configuration data) and to open valve2 (if previously closed, as also determined by its state). Step 102 then generates a pre-determined pressure by invoking actuator-level pressure-generation functions 102. The generated pressure moves the micro-droplet to the right (it being assumed that generated pressure is not dissipated to the left in passage 98 and that passage 98 is "open" to the right of position 97), until final position 97 where the applied pressure dissipates to the exterior through vent2. The micro-droplet itself is prevented from entering vent2 by the hydrophobic protection of its connecting side passage. When the micro-droplet reaches its final position, after delay 103, step 104 halts the pressure generation functions by deactivating HTR1. The duration of active pressure generation may be determined as a pre-selected time interval, optionally dependent on the processor configuration. Alternatively, where a micro-droplet position sensor is available (for example, a thermal-type sensor or a capacitive-type sensor), step 103 may wait until the micro-droplet is sensed to be in the final position. Optional step 105 invokes the micro-valve functions to return valve1 and valve2 to their states before micro-droplet motion.

Finally, upon successful completion, the micro-droplet position in the microfluidic-processor configuration data is then updated in step 106.

5.2.5.6. Micro-Droplet Metering Function

The configuration-level micro-droplet metering function creates a new micro-droplet of a more precisely known and smaller volume of fluid from a usually less precisely known and larger fluid volume (a reactant, a sample, or so forth) introduced into a microfluidic processor.

Figure 8D:
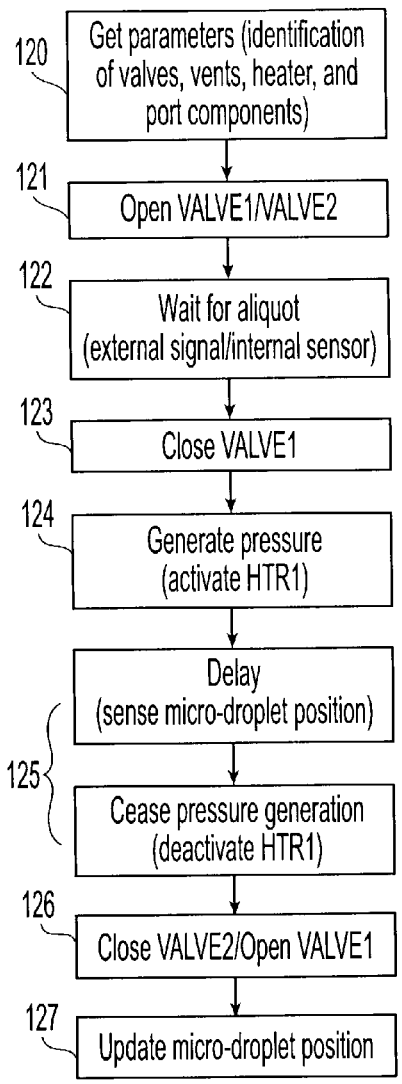
Figure 8C:
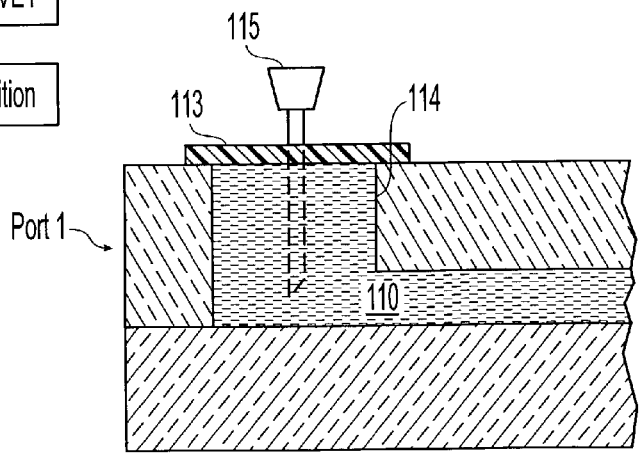

Fluids may be introduced into a processor through ports by manual transfer means (for example, a pipette) or by automatic transfer means (for example, a robot) from an exterior source. Ports may be provided on the microfluidic processor to accept various fluid transfer means, for example syringes or pipettes. FIG. 8C illustrates an exemplary port adapted for syringes. Port1 includes fluid reservoir 114, covered with puncturable membrane 113 (for example, of a self-sealing, rubber-like material), and connected to passage 110 in a microfluidic processor. This figure illustrates syringe 115 having punctured membrane 113 and already having introduced fluid into the port. The membrane insures injected fluid penetrates into the processor without back flow. In the case of pipettes, the shape of reservoir 114 may be adapted to a sealed fit with the pipette tip for fluid transfer.

In a preferred embodiment, a new micro-droplet is metered by being pinched off from the larger volume, generally by means of a gas pressure force. Micro-droplet metering is illustrated with reference to FIG. 8A, which shows an initial configuration before metering, FIG. 8B, which shows a final configuration with new, metered micro-droplet 112, and to FIG. 8C, which shows steps of the preferred metering control function. FIG. 8A illustrates fluid aliquot 111, having been introduced through port1 (such as the port illustrated in FIG. 8C) filling passage 110 up to the stable position formed by hydrophobic region h1. Hydrophobic region h2 prevents fluid entry into the side passage to HTR1. Excess fluid may escape through vent1, since valve1 is initially open, and excess gas may escape though vent2, since valve2 is initially open. Passage 110 is designed, i.e., by having the illustrated relative sizes, so that fluid aliquot 111 experiences greater capillary force there than in the side passage to vent1, in order that the fluid aliquot extends to the hydrophobic patch before excess liquid extends to vent1. This configuration of passage sizes further stabilizes the stable position formed by hydrophobic region h1.

The metering operation begins, as usual, at step 120, which identifies the metering components, their states, their arrangement, order, and their signal lines or external connectors. Optional step 121 opens valve1 and valve2 by means of the actuator-level micro-valve functions, if they were not initially open. Next, the metering function waits 122 for the loading of the fluid aliquot from which a micro-droplet is to be metered. Its loading may be indicated by an external manual signal provided to the user equipment (and transmitted to the DAQ board), or may be automatically indicated by completion of robotic loading, or may be provided by an internal sensor which can detect the presence of fluid adjacent to hydrophobic region h1 of passage 110. Step 123 then closes valve1 by invoking the micro-valve close function, so that no more fluid may escape out of vent1.

Step 124 generates pressure by invoking the actuator-level pressure generator function (which activates HTR1). The pressure generator is controlled to a pre-determined pressure (if pressure sensors are available) or, alternatively, to a pre-determined metering temperature. The resulting gas pressure pinches a length L of aliquot 111 that lies between the exit of the side passage to the pressure generator and the end of the aliquot at the stable position, forming a new micro-droplet. The volume of the metered micro-droplet is determined by length L and the cross-section of passage 110. With reference now to FIG. 8B, the generated pressure further acts to move new micro-droplet 112, in the manner of the micro-droplet motion function described above, to position 117, which is just beyond a side passage to vent2. The generated pressures dissipates out vent2 since valve2 is open. Steps 125 and 126 cease pressure generation after a pre-determined delay, or alternatively after micro-droplet 112 is sensed to be in position 117 (by a micro-droplet position sensor). Finally, an optional step closes valve2, to prevent further gas escape, thereby keeping the new micro-droplet from rejoining fluid aliquot 111. Valve1 may be returned to its initial state.

Lastly, step 127 updates the microfluidic processor configuration to reflect the presence, location, and composition (the same as aliquot 111) of the new micro-droplet.

5.2.5.7. Micro-Droplet Mixing Function

Effective mixing of inhomogeneous micro-droplets is useful because simple diffusion, especially of biological macromolecules, is often too slow to be practicable, even for adjacent micro-droplets in physical contact. Generally, micro-droplet mixing is achieved by motion that is sufficiently rapid, in view of the passage size and droplet viscosity, to induce micro-droplet mixing. Preferably, the micro-droplet velocity equals or exceeds the critical inter-layering velocity. In a preferred embodiment, a micro-droplet-level mixing function may invoke a micro-droplet-level motion function in such a manner that the motion is sufficiently rapid. This may be achieved by activating the pressure generator actuator, which provides the mechanical force to move the micro-droplet, so that the generated pressure rises sufficiently rapidly to a sufficiently high level to cause rapid motion. Appropriate activation of the pressure generator heater so that mixing of micro-droplets of particular viscosities occurs in passages of various sizes can readily be determined experimentally and stored for use by the mixing function.

Figure 9B:
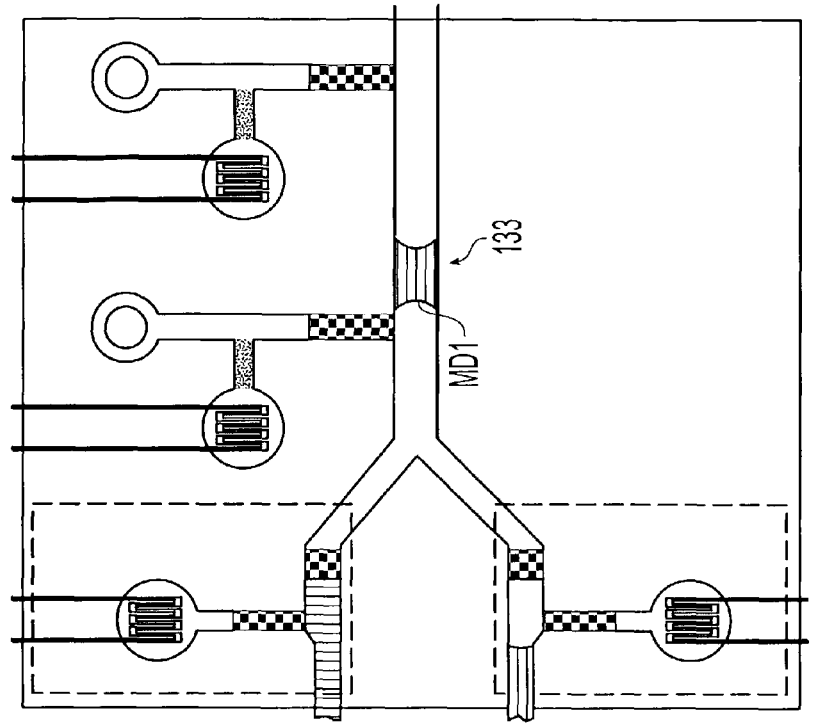
Figure 9A:
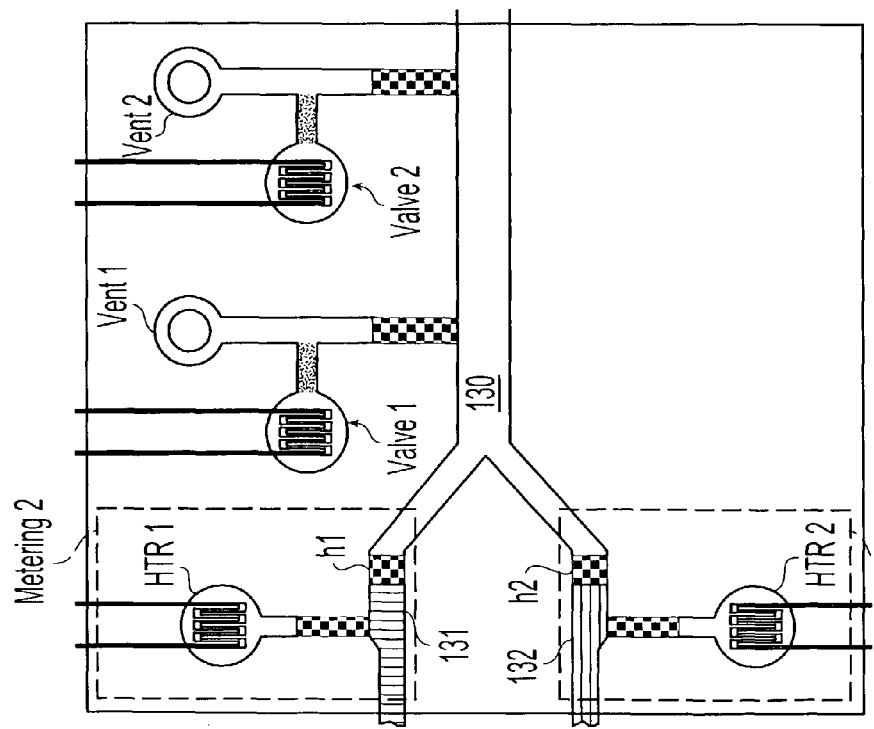
Figure 9D:
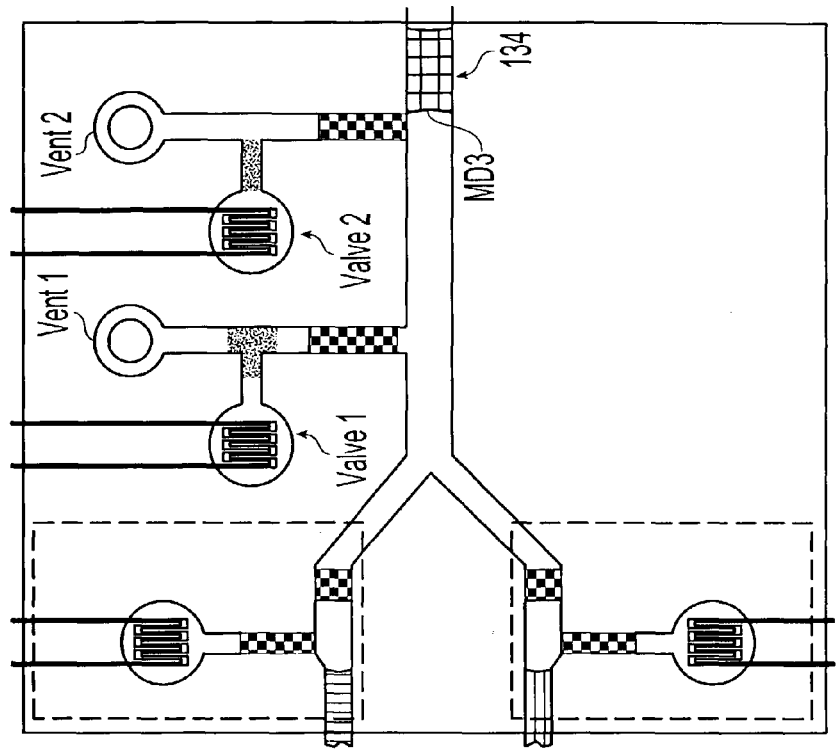
Figure 9C:
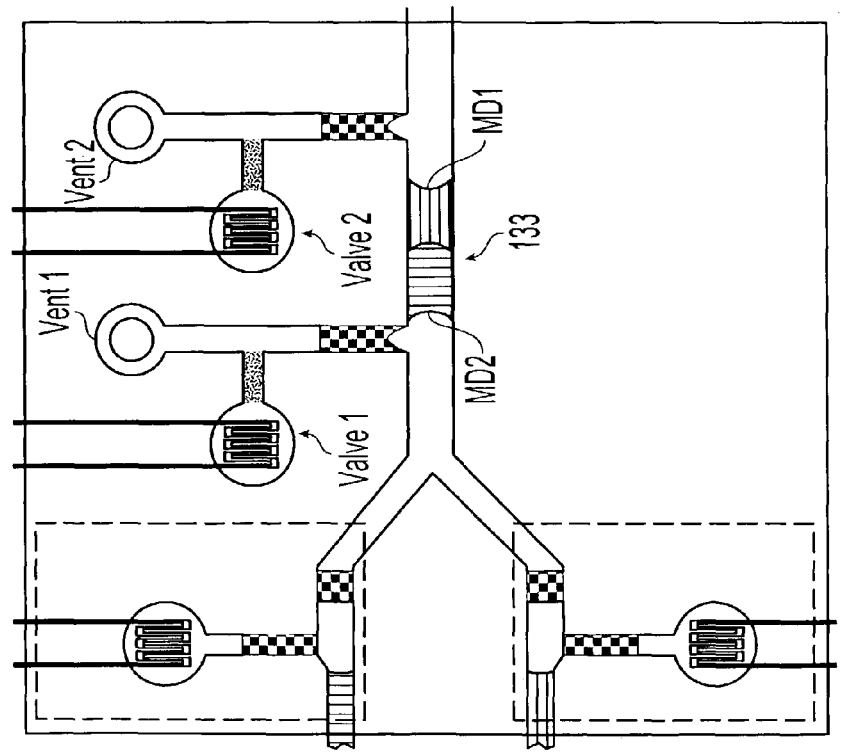

Inhomogeneous micro-droplets requiring mixing may arise for various reasons. For example, FIGS. 9A-C illustrate formation of an inhomogeneous micro-droplet as a result of metering two different fluid aliquots into two adjacent micro-droplets. FIG. 9A illustrates portions of two metering assemblies, metering1 and metering2, after loading aliquot 131 of a first fluid and aliquot 132 of a second fluid, but prior to micro-droplet metering. (FIGS. 8A-B illustrate such metering assemblies in full.) Pressure generator heaters, HTR1 and HTR2, are parts of these two metering assemblies. FIG. 9B next illustrates micro-droplet, md1, in position 133 after it has been metered from aliquot 132. Next, FIG. 9C illustrates md2 in position 133 after it in turn has been metered from aliquot 131. Md2 is positioned adjacent to md1, and these two micro-droplets now form, in effect, a single inhomogeneous micro-droplet.

Figure 9E:
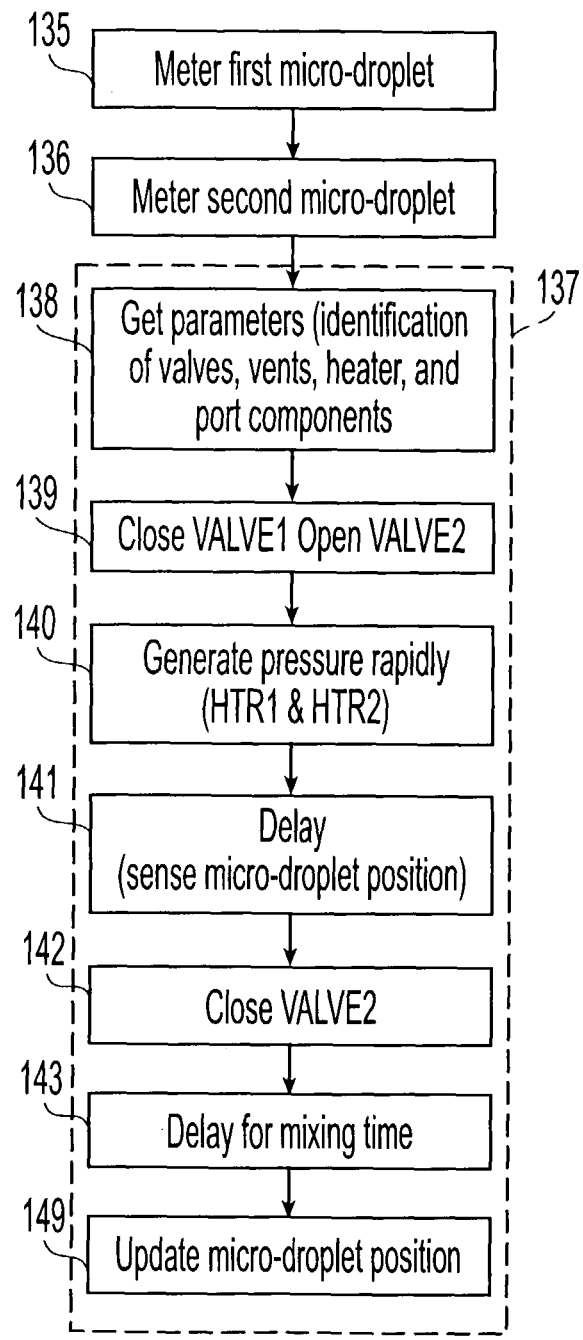

The mixing function is now described with reference to FIG. 9C, which depicts the configuration prior to mixing, FIG. 9D, which depicts the configuration after results of mixing, and FIG. 9E. This latter figure depicts the described preliminary metering steps 135 and 136 which prepare an inhomogeneous micro-droplet for mixing, as well as steps 137 of the actual mixing function. Step 138, as customary, obtains necessary input parameters, including identification of the mixing assembly components (here, portions of the two metering assemblies) and their control leads, and positions of the micro-droplet to be mixed. In this case, pressure for micro-droplet mixing may be generated by either or both of the pressure generators present in the metering components. Step 139 invokes actuator-level micro-valve functions to close valve1 (which is usually open as a result of the previous metering steps), and to open valve2, if necessary. Next, step 140 invokes the actuator-level pressure generation function to rapidly generate pressure, using either or both of HTR1 and HTR2 heated to a sufficient temperature (the mixing temperature) to cause mixing of the micro-droplet. Step 141 delays until (or senses when) micro-droplet md3 has reached position 134, then step 142 closes valve2 behind the md3.

Lastly, step 144 updates the microfluidic processor configuration data to reflect the location and composition (now mixed) of the new micro-droplet.

5.2.5.8. Perform Reaction Function

Generally, a micro-droplet that has been created with the correct composition is ready for the intended reaction or analysis. Preferably, for reaction, this micro-droplet is then isolated in order to avoid evaporation or unintended interactions with the remainder of the microfluidic processor, and adjusted to a determined temperature, in order that the reaction proceeds as intended. Certain reactions, notably the polymerase chain reaction (PCR), may require that the micro-droplet be repeatedly cycled through a determined temperature protocol. Other reactions may require a (solid) catalyst, which will need to be in the reaction region of the microfluidic processor. Further, reactions may require radiation stimulation. Although the following description is, without limitation, in terms of reactions at a determined temperature, one of average skill in terms of the following description will readily understand how to provide for temperature protocols, catalysis, radiation stimulation and so forth.

Figure 10A:
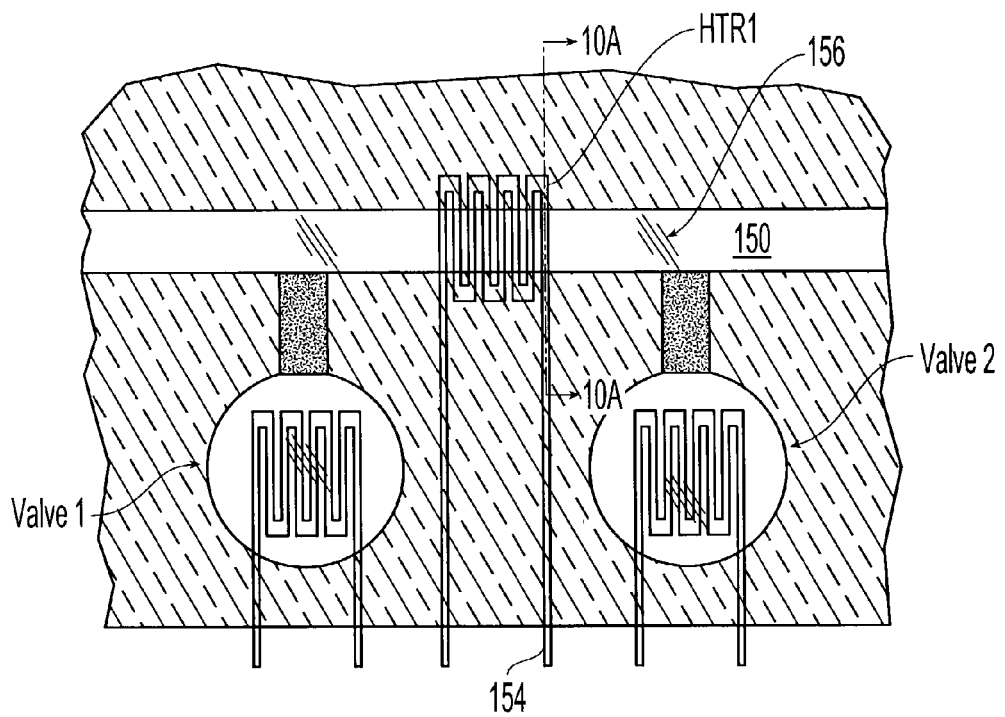

Therefore, in the preferred embodiment described, reactions are performed in a controllably-heated region of a passage that may be isolated from the rest of the microfluidic processor, or in a controllably-heated reservoir into which a micro-droplet can be moved and isolated. FIG. 10A illustrates exemplary reaction region 156 (without any catalyst) in passage 150, having a controllable heater, HTR1, and isolating valves, valve1 and valve2. Region 156 is a stable position for a micro-droplet because of, for example, side passage 151 leading to a controllable vent. (Similar stable positions are discussed with respect to, inter alia, FIG. 1.) Alternately, a suitably placed hydrophobic region may define this stable position.

Figure 10B:
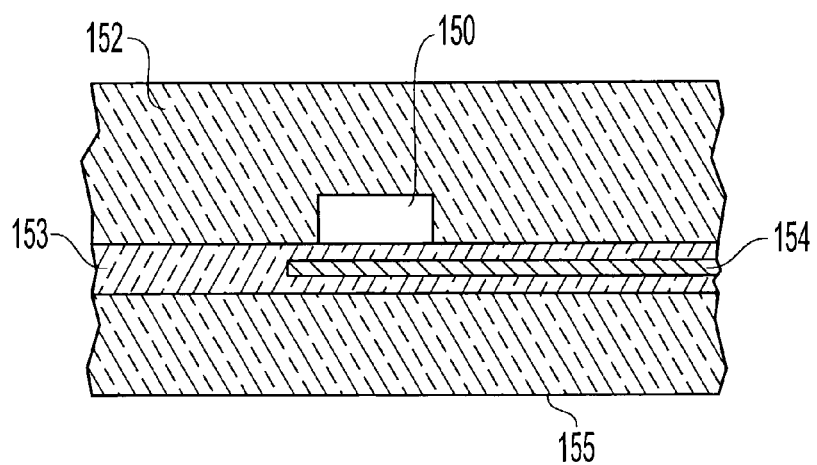
Figure 10C:
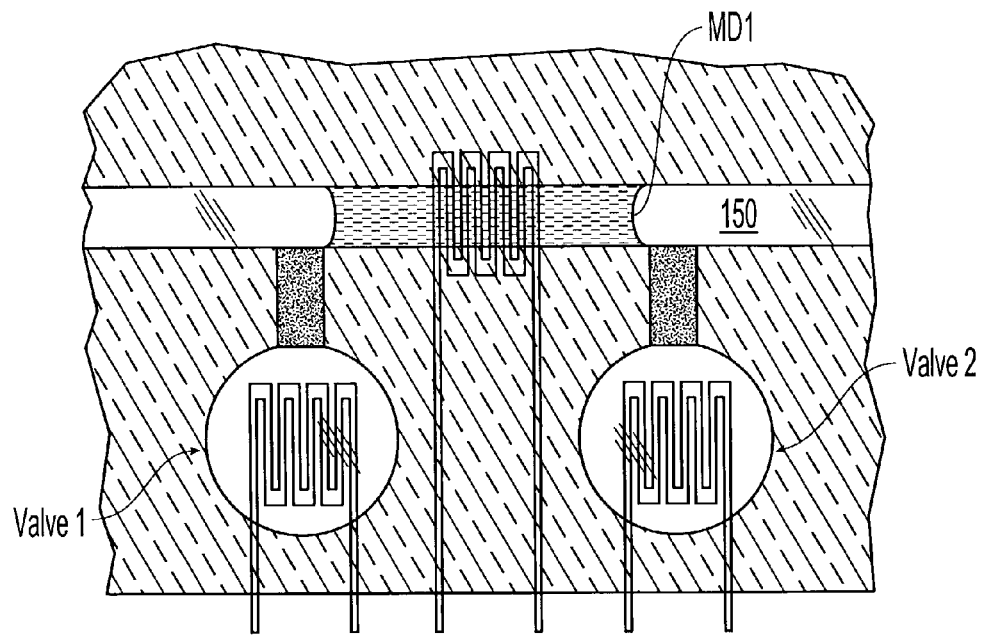
Figure 10D:
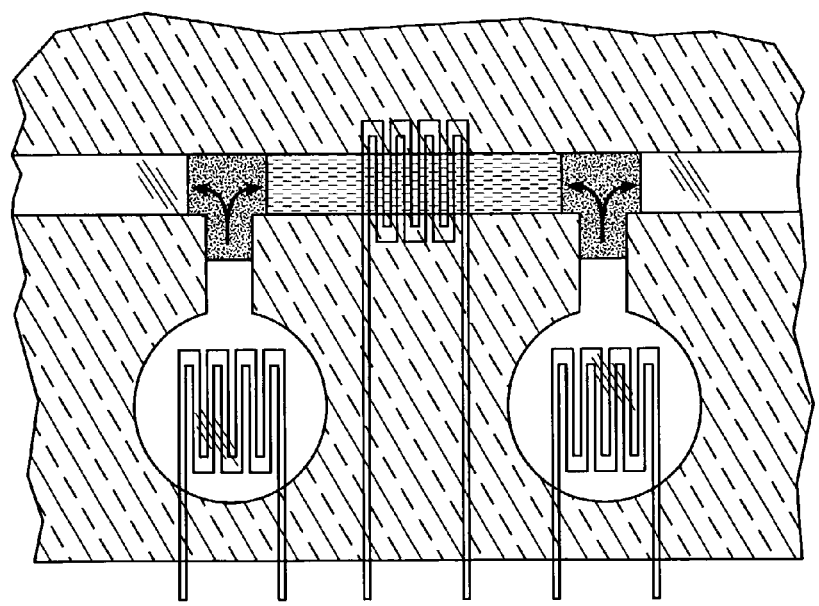
Figure 10E:
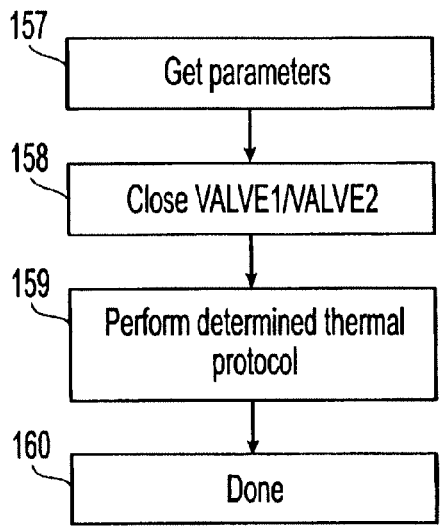

A reaction control function is illustrated with respect to FIG. 10C, which depicts reaction region 156 before reaction, to FIG. 10D, which depicts reaction region in the course of the reaction, and to FIG. 10E, which depicts the steps of a reaction control function. Step 157 obtains parameters including microfluidic processor configuration, the temperature profile for the reaction, the identities of the components forming the reaction region and their control leads and connectors. From the obtained configuration, this function checks that a micro-droplet having the correct composition is positioned in the reaction region as a result of prior microfluidic processing steps. If not, this function exits, perhaps with an error indication. Next, step 158 invokes the actuator-level micro-valve functions to isolate reaction region 156 by closing valve1 and valve2. Step 159 performs the prescribed thermal protocol. Since no micro-droplet positions are changed by this function, the configuration need be updated only to the extent of indicating that a reaction has been performed.

This reaction completed may be the final result of the microfluidic processing, in which case the contents of the resulting micro-droplet are sensed, or it may be an intermediary reaction, in which case the resulting micro-droplet is further processed.

Next, exemplary construction of preferred, thermally-controlled microfluidic processors is briefly described. For example, FIG. 10B illustrates a section of FIG. 10A along line 10A-10B depicting general construction of such processors from top plate 152, and parallel bottom plate 155, which is positioned and bonded with a seal against the top plate. The plates may be silicon, plastic polymer, glass or so forth. Passages, such as passage 150, are machined, etched, pressed, or otherwise defined in one plate, here the top plate, while the bottom plate is substantially flat, and have walls appropriately treated for the type of micro-droplets to be processed. In particular, hydrophobic (or hydrophilic) passage regions are defined by passage treatments before plate bonding. Electrical components and leads, such as lead 154, are deposited preferably on the non-etched, substantially flat plate, and are covered (also, underlain if necessary) by insulating layer 153, which is inert to contents of the passages. Leads may be vapor deposited metal, for example, aluminum. Insulating layer may be a ceramic or polymer, for example, silicon dioxide. Light conductors may be made from optic fibers attached to a processor after plate bonding. Construction methods are adapted from those well known in the lithographic arts used in semiconductor fabrication. See, for example, U.S. Pat. Nos. 6,048,734, 6,057,149, and 6,130,098.

5.2.5.9. Integrated Device Operation Functions

The previously described micro-droplet-level functions can be combined to create user-level reaction-control functions for many different types of microfluidic processors performing many different reactions or analyses. Construction, or programming, of such control functions according to the present invention is enormously simplified because attention need generally only be paid to intuitive micro-droplet-level functions, which specify laboratory functions familiar to chemists and biologists, such as metering, moving, mixing, or reacting. Details of individual microfluidic-processor components and of their sequential control are hidden by the hierarchical construction of the component-level, actuator-level, and micro-droplet-level control functions, all of which function cooperatively to perform necessary low-level microfluidic processor control. This hierarchical control is possible because of the discrete nature of the controlled microfluidic processors.

These advantages are illustrated by a user-level reaction-control function for the preferred thermally-controlled microfluidic processor illustrated in FIG. 1. This processor is capable of performing, inter alia, a simple PCR analysis of sample by metering a first micro-droplet containing the sample and some PCR reagents, by metering a second micro-droplet containing remaining PCR reagents, by mixing the two micro-droplets, by performing a PCR temperature protocol on the mixed micro-droplet, and by detecting the reaction results.

In more detail, FIG. 12 illustrates a user-level PCR-reaction-control function, controlled by user commands entered on a host system. Step 175 starts the reaction-control function after a user enters a command at host equipment. Next, step 176 obtains input parameters, which include data descriptive of the microfluidic processor on which the reaction is to be performed. As described, this descriptive data may be provided by the microfluidic processor itself, or the processor may provide a key to a database of such data. This function identifies the components, actuators, and sub-assemblies required by subsequent micro-droplet-level functions, and preferably checks that this processor has these correct resources in a correct arrangement. In the microfluidic processor of FIG. 1, these resources are checked and identified as metering1, metering2, mixing1, and reaction/detection1. Next, steps 177 and 178, using the metering micro-droplet-level functions parameterized by the metering1 and metering2 sub-assemblies, meter first and second micro-droplets, including a sample for PCR analysis and reagents. Both metering steps wait (see, for example, FIG. 8D) for a signal indicating the aliquots from which the micro-droplets are metered have been loaded into the processor. Next, step 179 invokes the mixing micro-droplet-level function parameterized by the mixing1 sub-assembly to mix the metered micro-droplets. Since the mixed micro-droplet is now located in the reaction region of the reaction/detection1 sub-assembly, step 180 performs the reaction by invoking the perform-reaction micro-droplet-level function. Lastly, step 181 optically analyzes the reaction results by invoking the sense reaction results actuator-level function. Upon reaction completion, step 182 returns the reaction results and a completion signal to the host system. Throughout the operation of this function, asynchronous host monitoring or control 183 may be in progress, for example, by monitoring the microfluidic processor configuration data as it is updated by the various invoked functions.

Therefore, this exemplary PCR reaction can be specified entirely in terms of high-level micro-droplet functions. Detailed operations of several individual components that must be coordinated to perform this function are generally encapsulated by the micro-droplet functions in which the reaction control is expressed.

In an alternative embodiment, the reaction control function, after obtaining the microfluidic processor description, determines itself which processor components to use to perform the intended reaction. If micro-droplets need to be moved between components that are not directly connected, the control function may insert the necessary micro-droplet move function invocations. This determination is analogous to the layout and wiring of a hardware description expressed in high-level hardware description language (such as VHDL) on a semiconductor chip, and can be performed by similar methods. Further alternatives apparent to one of skill in the art are also included in this invention.

5.2.5.10. Sample Preparation

The control systems and methods of the present invention are advantageously applied to control microfluidic processors to perform pre-determined analyses of biological and medical samples. Exemplary analyses include determining the presence of certain nucleic acids or proteins that may indicate a disease state of an organism and help in diagnosing the disease state.

Accordingly, FIG. 13 illustrates the preparation of such samples for analyses. First, a biological or medical specimen is obtained, such as samples obtained from the exterior of an organism, for example, by scraping or swabbing, or from the interior of an organism, for example, by biopsy or surgical specimen. Next a sample is prepared from the specimen. This may include the steps of purifying the specimen from extraneous material (removing cells where extracellular material is to be analyzed), lysing cell (where intracellular materials are to be analyzed), separating the type of material to be analyzed from other types (for example, nucleic acids from proteins). Finally, the prepared sample is loaded into a microfluidic processor for analysis by the systems and methods of this invention.

5.3. General Purpose Embodiments

In the previous subsection, the control systems and methods of this invention were described in considerable detail with reference to the microfluidic processor of FIG. 1. This processor, however, has somewhat limited flexibility in that, it is essentially limited to carrying out a single one or two-component reaction in each processing cycle, because it can meter a maximum of two micro-droplets and can react and sense only a single micro-droplet.

In this subsection, the general purpose aspects of the control systems and methods of this invention are described with reference to a microfluidic processor of considerably greater flexibility. To advantageously realize increased flexibility, a processor will include at least one "conditional" sub-assembly which is capable of being controlled to produce at least two distinct outcomes. A switch sub-assembly, an exemplary conditional sub-assembly, is described next and then used as a basis of a more general purpose microfluidic processor.

5.3.1. Switch Sub-Assembly

A switch sub-assembly is a conditional sub-assembly which can be controlled to move a micro-droplet from an inlet passageway to one of two or more outlet passageways.

FIG. 15 illustrates an exemplary basic switch sub-assembly having inlet passage 231, upper outlet passage 233, and lower outlet passage 235 constructed in a thermally-controlled technology. Valve actuator 237 (schematically illustrated as above) controls upper outlet passage 233, and actuator 239 controls lower outlet passage 235. In order for a micro-drop to move from the inlet passage to the upper outlet passage, valve actuator 237 is controlled to be open and valve actuator 239 is controlled to be closed. Conversely, to move a micro-drop from the inlet to the lower outlet passage, valve actuator 237 is controlled to be closed and valve actuator 239 is controlled to be open.

In alternative embodiments, a thermally-controlled switch sub-assembly may include additional actuators that enhance micro-droplet motion through the sub-assembly. For example, the inlet port may be equipped with an additional downstream valve actuator and an upstream pressure generator. Accordingly, after entry of a micro-drop into the switch sub-assembly and after appropriate control of valve actuators 237 and 239, the downstream valve actuator may be closed and the pressure generator activated so that the micro-droplet may be forced out of the open outlet passage.

Although more general purpose processors are subsequently described based on this switch sub-assembly, the control systems and methods of this invention are applicable to other conditional processing sub-assemblies and actuators.

5.3.2. Micro-Fluidic Processor with Valve Sub-Assembly

FIG. 16 illustrates an exemplary microfluidic processor having more general purpose capabilities that is used to describe general purpose embodiments of the control systems and methods of the present invention.

In more detail, the microprocessor of FIG. 16 is capable of metering up to four micro-droplets from four different sources, of forming up to three mixed micro-droplets, and of performing a first reaction followed by one or more second reactions. Further, it is built from the sub-assemblies used in and already described with reference to the processor of FIG. 1 along with a switch block as an exemplary conditional sub-assembly. Thus metering blocks 251 and 255 can meter micro-droplets from reagent or sample sources 253 and 257 (respectively). Next, mixing block 259 can optionally mix these metered micro-droplets; and reacting/detecting block 261 can optionally react the mixed micro-droplet and detect reaction results. Alternatively, these sub-assemblies may move micro-droplets without change from their inlet to their outlet passages.

Next, switch block 263 can be controlled to forward the processed micro-droplet resulting from these actions to either its upper or its lower outlet passages. In case the processed micro-droplet is forwarded to the upper passage, it can be further mixed with a micro-droplet metered from reagent source 267 by metering block 265, and then the mixed microdroplet then further reacted and sensed in reacting/detecting block 271. If further processing is necessary, the reacted micro-drop may be forwarded to further sub-assemblies 273. In case the processed micro-droplet is forwarded to the lower switch-block passage, similar processing may be performed by sub-assemblies 275, 279, and 281.

This microfluidic processor can perform several different processes. For example, a micro-drop may be metered from a sample introduced into inlet port 253 (or 257) by metering block 251 (or 255) and then passed through sub-assemblies 259 and 261 to switch block 263. The switch block may then direct the sample micro-drop into the upper passage for reaction with a micro-drop metered by block 265 from the reagent introduced into inlet port 267 (first analysis), or into the lower passage for reaction with a micro-drop metered from a different reagent introduced into inlet port 277 (second analysis). Further, both analyses may be performed by having the processor perform the first analysis and then perform the second analysis. Accordingly, a user, by having the control system set the switch block appropriately, causes this processor to perform the first analysis, or the second analysis, or both analyses upon a sample. Alternatively, these options may be programmed as separate programs that may be selected by the user.

For a further example, a particular analysis may require reaction of a sample with a combination of reagents that are unstable when stored mixed together (sequential mixing example). Such an analysis may be performed by the processor of FIG. 16 by loading a sample into inlet port 253, the first reagent into inlet port 257, and the second reagent into inlet port 267. The first micro-drop with the sample mixed with the first reagent may be formed by mixing in block 259 microdrops metered by blocks 251 and 255. The first micro-drop may be forwarded by the switch block to the upper passage where it is mixed in block 269 with a micro-drop of the second reagent metered by block 265. Finally, the desired analysis may be performed in reacting/detecting block 271 upon a micro-drop with a fresh mixture of the first and second reagents.

For an additional example, a user may wish to perform a first reaction with a sample and a first reagent, followed by a second reaction between the results of the first reaction and either a second or a third reagent. These reactions may be performed by loading a sample into inlet port 253, the first reagent into inlet port 257, the second reagent into inlet port 267, and the third reagent into inlet port 277. Then microdrops of the sample and the first reagent may be metered by blocks 251 and 255, mixed in block 259, and reacted in block 261. If the switch is controlled to the upper passage, then the micro-drop resulting from the first reaction may be mixed in block 269 with a micro-drop of the third reagent metered by block 265, and reacted and detected in block 271. If the switch is controlled to the lower passage, the micro-drop resulting from the first reaction will be reacted with the third reagent. Again, the user may control these reactions by instructing a single program how to control switch block 263 (or by selecting separate programs in which the switch block is controlled in a fixed manner). A user may perform reactions with both the second and the third reagent by simply repeating this program with a different switch setting (or by running each program sequentially).

The latter example may also illustrate automatic conditional processing by the processor of FIG. 16 (conditional processing example). Whether the second reaction is with the second or the third reagent may be automatically controlled by sensing in block 261 the composition (or other parameter) of the micro-droplet resulting from the first reaction, and then controlling switch block 263 according to the results of the sensing.

Exemplary Program Specifications

As described preferred input to the microfluidic-processor control systems and methods of this invention include programs specifying micro-drop operations (201 in FIG. 14) or sub-assembly operations (205 in FIG. 14). Exemplary programs for the latter example of the conditional processing of multiple reactions and other examples are described next.

Program 1 specifies automatic conditional processing of a first reaction between the sample and reagent R, followed by a second reaction between the intermediate results of the first reaction and either reagent S or T depending on the sensed output of the intermediate results. If the sensed intermediate condition or composition is "A," then the second reaction is with reagent S; if the sensed intermediate condition or composition is "B," then the second reaction is with reagent T; otherwise, the intermediate is unknown. As is apparent, Program 1 is written in a form that processes explicit micro-drops, i.e., micro-drops 1-7, by commands appropriate to micro-drops, i.e., creating or metering a micro-drop (":="), mixing two micro-drops ("MIX(_,_)"), reacting a micro-drop ("REACT(_)"), and sensing the condition or composition of a micro-drop ("SENSE(_)"). Otherwise the syntax of this, and subsequent programs, employs standard conventions.

Generally, as will be apparent to one of skill in the art, Program 1 assumes a certain initialization of micro-drops 1, 3 and 4. It then creates a sample micro-drop, mixes it with the first reagent, reacts the mixed micro-drop, and senses the intermediate result. If condition or composition "A" is sensed, then a reaction with the second reagent is performed; if condition or composition "B" is sensed, then a reaction with the third reagent is performed; otherwise an unknown is reported to the user.

The conditional processing of this program is automatic so that the user need simply select this program. Alternately, the sense results may be reported to the user, who then inputs data to the program for selecting the second reaction.

Program 1

```
// program for conditional processing example specified by
    micro-droplet operations
INITIAL_CONDITION
    // initial micro-droplets
    micro-droplet_1:=reagent R
    micro-droplet_3:=reagent S
    micro-droplet_4:=reagent T
START_PROCESSING
    // create micro-droplet from sample and mix with
        reagent R
    micro-droplet_2:=sample
    micro-droplet_5:=MIX(micro-droplet_1, micro-droplet_2)
    // react and sense mixed micro-droplet; expect A or B as
        an intermediate result
    micro-droplet_5:=REACT(micro-droplet_5)
    SENSE(micro-droplet_5)
    // if intermediate is A, then perform processing reaction
        with reagent S and sense
    IF (sense=intermediate A) THEN
        micro-droplet_6:=MIX(micro-droplet_3, micro-droplet_5)
        micro-droplet_6:=REACT(micro-droplet_6)
        SENSE(micro-droplet_6)
    // if intermediate is B, then perform reaction with reagent
        T and sense
    ELSE IF (sense=intermediate B) THEN
        micro-droplet_7:=MIX(micro-droplet_4, micro-droplet_5)
        micro-droplet_7:=REACT(micro-droplet_7)
        SENSE(micro-droplet_7)
    // if neither A nor B, then an unknown result has occurred
    ELSE unknown
END_PROCESSING
```

A system of this invention would execute the program with reference to microfluidic processor description information (i.e., the type and arrangement of processor sub-assemblies) and current processor state information (i.e., the composition and location of micro-droplets and available samples). For example, execution of the following exemplary statement micro-droplet_6:=MIX(micro-droplet_3, micro-droplet_5)

is briefly discussed. Suppose the sample and reagents R, S, and T have been loaded into metering blocks 1, 2, 3, and 4, respectively. Execution of statements prior to the exemplary statement cause micro-droplets to be metered from metering blocks 1 (the sample) and 2 (reagent R) to mixing block 1 where they are mixed into micro-droplet 5, which is next reacted and sensed in reaction/detection block 1. Now turning to the exemplary statement, MIX-processing first determines the current locations of its "operand" micro-droplets, micro-droplets 3 and 5. With reference to the current microfluidic processor state, these are determined to be located in metering block 3 and in reaction/detection block 1, respectively. Next, with reference to the determined micro-droplet positions and to processor description information, MIX-processing selects a convenient mixing block to use for mixing its "operands." Here, mixing block 2 is chosen because it is easily accessible from the current positions of micro-droplets 3 and 5, and it is further determined that switch block 1 (which intervenes between the current position of micro-droplet 5 and mixing block 2) must be set to exit to its upper output path to the chosen metering block. Finally, the processor operations are carried out by activating switch block 1, moving the "operand" micro-droplets to mixing block 2, and mixing them into micro-droplet 6. These activations are performed by generating control signals to directly controlled microfluidic processor elements according to further processor description information. Before completing, MIX-processing updates current processor state with sub-assembly state and micro-droplet position, and so forth. Other statements in program 1 may be similarly executed with reference to processor state and description information.

As previously discussed with reference to FIG. 14, a preferred embodiment of the systems and methods of this invention can accept program 1 along with processor description information describing the sub-assembly configuration of a particular microfluidic processor and convert it into an equivalent program in terms of sub-assembly operations. Program 2 is an exemplary of such conversion of Program 1. Program 2 refers only to particular sub-assemblies, and makes no reference to individual micro-drops because the sub-assemblies directly perform the necessary micro-drop operations. Further, Program 2 includes commands directed only to sub-assemblies, principally the ACTIVATE command which causes control signals to be generated to cause the reference sub-assembly to operate. Optionally, the ACTIVATE command may have modifiers where a particular sub-assembly is capable of two or more separate operations (for example, the reacting/detecting blocks).

Program 2

```
// program for conditional processing example specified by
    sub-assembly operations
INITIAL_CONDITION
    // initial loading of metering blocks
    metering_block_1 PRELOADED with reagent R
    metering_block_3 PRELOADED with reagent S
    metering_block_4 PRELOADED with reagent T
START_PROCESSING
    // create micro-droplets from sample and reagent R and
        mix
    LOAD sample into metering_block_2
    ACTIVATE meteting_block_1
    ACTIVATE meteting_block_2
    ACTIVATE mixing_block_1
```

// react and sense mixed micro-droplet; expect A or B as intermediate results
ACTIVATE reacting/detecting_block_1 (for REACTING)
ACTIVATE reacting/detecting_block_1 (for SENSING)
// if intermediate is A, then perform processing of upper path by mixing intermediate
// with drop metered from metering_block_2, then reacting and sensing
IF (sense=intermediate A) THEN
   ACTIVATE switch_block_1 for upper output
   ACTIVATE meteting_block_3
   ACTIVATE mixing_block_2
   ACTIVATE reacting/detecting_block_2 (for REACTING)
   ACTIVATE reacting/detecting_block_3 (for SENSING)
// if intermediate is B, then perform processing of lower path by mixing intermediate
// with drop metered from metering_block_3, then reacting and sensing
ELSE IF (sense=intermediate B) THEN
   ACTIVATE switch_block_1 for lower output
   ACTIVATE meteting_block_4
   ACTIVATE mixing_block_3
   ACTIVATE reacting/detecting_block_3 (for REACTING)
   ACTIVATE reacting/detecting_block_3 (for SENSING)
// if neither A nor B, then an unknown result has occurred
ELSE unknown
END_PROCESSING Programs 3A and 3B are sub-assembly specifications appropriate to performing the sequential mixing example discussed above. As will be apparent. Program 3A sequentially mixes a sample micro-drop first with a micro-drop metered from the first reagent by block 251, and then with a micro-drop metered from the second reagent by block 265. This micro-drop composed of the sample and both reagents is then reacted and sensed. Program 3B is the same as Program 3A except that the second micro-drop is metered from a third reagent by block 275.

Program 3A

// program for sequential mixing example specified by sub-assembly operations
INITIAL_CONDITION
   // initial loading of metering blocks
   metering_block_1 PRELOADED with reagent R
   metering_block_3 PRELOADED with reagent S
START_PROCESSING
   // create micro-droplets from sample and reagent R and mix
   LOAD sample into metering_block_2
   ACTIVATE meteting_block_1
   ACTIVATE meteting_block_2
   ACTIVATE mixing_block_1
   // pass mixed micro-droplet through to mixing block 3 without reaction
   ACTIVATE switch_block_1 for upper output
   // create micro-droplet from reagent S and mix with first micro-droplet
   ACTIVATE meteting_block_3
   ACTIVATE mixing_block_2
   // react and sense results
   ACTIVATE reacting/detecting_block_2 (for REACTING)
   ACTIVATE reacting/detecting block_2 (for SENSING)
END_PROCESSING Program 3B // program for sequential mixing example specified by sub-assembly operations
INITIAL_CONDITION
   // initial loading of metering blocks
   metering_block_1 PRELOADED with reagent R
   metering_block_4 PRELOADED with reagent T
START_PROCESSING
   // create micro-droplets from sample and reagent R and mix
   LOAD sample into metering_block_2
   ACTIVATE meteting_block_1
   ACTIVATE meteting_block_2
   ACTIVATE mixing_block_1
   // pass mixed micro-droplet through to mixing block 3 without reaction
   ACTIVATE switch_block_1 for lower output
   // create micro-droplet from reagent T and mix with first micro-droplet
   ACTIVATE meteting_block_4
   ACTIVATE mixing_block_3
   // react and sense results
   ACTIVATE reacting/detecting_block_3 (for REACTING)
   ACTIVATE reacting/detecting_block_3 (for SENSING)
END_PROCESSING A user may cause either analysis to be performed by instructing the system and method of the present invention to retrieve and execute the appropriate program. Because the two analyses use different processor resources, a user may perform both analyses on the same microfluidic processor by instructing the present invention to perform first one program and then the other program. Alternatively, a user interface display may present the options to the user who then need merely select the desired analyses or both analyses by use of, e.g., a pointing or selection user-interface device.

5.4. Reagent Package

A reagent package (or a reagent pack) is a simplified microfluidic device designed to assist the loading of one or more reagents, and also optionally of sample material, into a microfluidic device prior to initiating a processing or analysis program. Generally, a reagent pack contains one or more fluid reservoirs which have been loaded with selected reagents and which communicate with outlet ports geometrically configured to sealingly couple, or join, or mate with the inlet ports on a target microfluidic processor. Preferably, a reagent pack may be mated with a compatible microfluidic processor with no more than manual pressure. In certain embodiments, the reservoirs, outlet ports, and target microfluidic processor permit the reagents to flow under gravity after a reagent pack is mated to the target microfluidic processor. In alternative embodiments, fluid in the reservoirs may be forced into the inlet ports of a target microfluidic processor by, for example, gas pressure resulting from a static charge of a (relatively inert) gas or generated by the previously-described pressure generators. (A reagent pack may provide for sample loading by either containing the sample within one of its fluid reservoirs, or more preferably, by providing pass-through-type external access to a sample port on the target microfluidic processor.)

Reagent packages are advantageous in several applications. First, they provide a convenient, reliable, and portable means for providing reagents to a microfluidic processor. Although robot-type devices may be advantageous for high-throughput laboratory applications, in field applications, away from laboratory environments, reagent packs may be preferable. Such field applications may include medical testing in a doctor's office or clinic, or industrial testing in a factory environment, or environmental testing of outdoor pollutants, or the like. Second, reagent packs complement well the previously-described general purpose microfluidic processors and their control systems. For example, the multiple different analyses or processes that a single general purpose microfluidic processor may perform are advantageously supported by providing both a controller having processing programs selectable for each different analysis or process and one or more reagent packs compatible with the processor and having the proper reagents properly arranged for each analysis of process. Then, to perform a particular analysis, a user need only mate the correct reagent pack to the microfluidic processor, link the combination to the controller, and select the correct processing program or sub-program. If the particular processor is reusable, then performing another analysis requires only mating another reagent pack and selecting another processing program.

In certain embodiments, a general purpose microfluidic processor may be packaged together in a kit with one or more reagent packs having reagents for analyses or processes of which the processor is capable. Such a kit may also include a computer readable medium with encoded software instructions for causing a general-purpose, programmable controller to command the processor to perform analyses or processes. This medium may be a floppy disc, or a mini CD-ROM, or a flash memory card, or the like. Kits may be specialized for particular analysis scenarios in the intended application. For example, for office diagnoses, a general purpose processor may be packaged with reagent packs with reagents suitable for detecting common infectious agents found at various sites of infection, e.g., nasopharyngeal infections (sore throat), pulmonary infections, urinary tract infections, and the like. Alternatively a kit directed to diagnosing pulmonary infections, may include reagent packs for both common agents, rare agents, agents common in compromised hosts, and the like. Similar specialized kits may be assembled for other application areas such as environmental field testing, industrial testing, and so forth.

In more detail, an exemplary reagent pack that is compatible with the exemplary general-purpose, microfluidic processor, previously described with reference to FIG. 16, is now described with reference to FIGS. 17A-C. Generally, as illustrated in FIG. 17A, a reagent pack and a microfluidic processor are compatible if the outlet ports on the reagent pack may be mated for reagent exchange with the inlet ports of the processor. Generally illustrated microfluidic processor 311 having inlet ports 313a-d corresponds to the exemplary general purpose processor illustrated and discussed with respect to FIG. 16. The processor illustrated in the latter figure has inlet ports 253, 257, 267, and 277 in a geometric arrangement similar to ports 313a-d of FIG. 17A. Generally illustrated, exemplary reagent pack 301 has outlet ports 303a-d in the same arrangement as inlet ports 313a-d. Therefore, where pack 301 is mated to processor 311 as indicated by arrow 317, the inlet and outlet ports will mate for reagent (or fluid) exchange. When mated, a reagent pack should not obstruct external signal contacts on a mated processor, which can be achieved if the reagent-pack's width is smaller than that of a mated processor (as illustrated in FIG. 17A) so that lateral contacts on the processor remain accessible.

Preferably, reagent packs are constructed as microfluidic devices using the same or similar techniques that are used to construct microfluidic processors. In fact, reagent packs may be considered as highly simplified processors that can incorporate components and actuators (even sub-assemblies), as previously described, to achieve their reagent dispensing function. FIG. 17B schematically illustrates an exemplary construction for reagent pack 301 as a microfluidic device with differing arrangements for the fluid reservoirs in fluid communication with output ports 303a-d. One arrangement is illustrated by outlet port 303d, which is in communication with fluid reservoir 305d in the reagent pack. Here, fluid is expelled from the reservoir through this port by the static pressure of a relatively inert gas (e.g., $N_2$ or Ar) that is present in gas reservoir 310. This pressurizing gas may be loaded into reservoir 310 at the time the reagent is loaded into reservoir 305d. To prevent mixing of the pressurizing gas and the reagent fluid, the gas reservoir may be linked to fluid reservoir 305d for the application of gas pressure by a narrow channel with a hydrophobic region (in case the reagent is hydrophilic).

Additional fluid-reservoir arrangements are illustrated at outlet ports 303a and 303c in FIG. 17B. These outlet ports are in communication with reagent fluid reservoirs 305a and 305c, respectively. Fluid is expelled from these ports upon activation of pressure generators 307a and 307c, which operate as previously described. The processor controller activates these pressure generators by means of signals applied to internal heating elements via leads (not shown in FIG. 17B). Control signals may be applied directly to the leads by means of external contacts on the reagent pack. Alternatively, these leads may by in signal communication with leads on the compatible microfluidic processor, and the reagent pack may be controlled via signals applied to the processor. Reagent loading through these ports would then be controlled by a controller program.

A further arrangement is illustrated at outlet port 308b. This port is used to load samples for analysis or processing and may be externally accessed through loading port 309. As illustrated, the loading port is vertically arranged and protected with a membrane. Such a port may be loaded by puncturing the membrane with a needle or syringe. Alternatively, a loading port may be adapted for pipette loading, may be laterally displaced, and so forth.

Finally, where an available processor port is not needed for particular analysis or process, the corresponding reagent pack may have no corresponding outlet port, or an outlet port that seals the inlet port.

FIG. 17C illustrates an exemplary arrangement for mating in a sealing fashion inlet and outlet ports, here inlet port 313a with outlet port 303a. Here, outlet port 303a is protected and sealed with membrane 311 which is easily breakable. For example, this membrane may be thin metal foil scored so that it is easily punctured. Inlet port 313a is surrounded by raised ring 315 dimensioned to that it will fit into outlet port 303a and puncture or break the protecting membrane when the two ports are mated. This ring may further serve as a gasket minimizing leakage upon reagent transfer. Alternatively, the processor inlet port may be protected by a membrane with the ring formed on the reagent pack; or both ports may be protected and the processor and the pack may have rings (and/or recesses to accommodate a ring) that mate to break both membranes. And in another embodiment, the mating surfaces of the reagent pack and/or the microfluidic processor may be protected by a removable membrane that would be removed or peeled prior to mating the pack with the processor.

It is to be understood that FIGS. 17A-C illustrate an exemplary construction of a reagent pack capable of mating with and supplying reagents to a microfluidic processor. The present invention includes other designs performing such reagent-supply functions but where details of reagent reservoirs, methods of fluid discharge, arrangement for port mating and sealing, and so forth, vary. For example, in such embodiments, certain microfluidic processor functions may be incorporated in the reagent pack and controlled, directly or indirectly via the processor, by the system controller. Reagent metering subassemblies may be advantageously incorporated in a reagent pack so that the pack supplies the needed volumes. By moving metering subassemblies to the reagent pack more space becomes available on the processor for constructing additional processing actuators and assemblies. Other divisions of processing between a reagent pack and a processor are possible, even including an approximately equal division.

The present invention also includes embodiments in which reagents are stored in a reagent pack in non-liquid forms. For example, a reagent may be stored in a solid form that is readily miscible with an appropriate solvent. Then the reagent pack would contain a reservoir with the solid form and a reservoir with the solvent (liquid), and when called upon to dispense the particular reagent to a microfluidic processor, the pack would provide for flow of the solvent to the reagent reservoir and then to an outlet port. The solid form would then mix, dissolve, or otherwise disperse into the solvent. In particular, the readily-miscible solid form may be a lyophilized reagent and the solvent may be water. Such solid-form storage may be particularly useful for readily-decomposable reagents or for long-term storage. For a further example, a reagent may be stored in a gaseous form and may be made available by dissolving in a solvent, or may simply be dispensed as a gas. Reagent packs are also adaptable to other convenient methods of reagent storage and preservation.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior art to the invention of the subject matter claimed herein.

What is claimed is:

1. A microprocessor-based method for controlling a microfluidic device, the method comprising:
    selecting a micro-droplet processing request from a preselected group of micro-droplet processing requests,
        wherein each request in the group specifies the creation or transformation of at least one micro-droplet confined in at least one microchannel in the microfluidic device, and
        wherein the microfluidic device comprises at least one resistive temperature detector which provides a sense signal indicative of a result of performing at least one selected micro-droplet processing request, wherein the microfluidic device is configured to perform two or more different processes relating to the micro-droplet processing requests on the micro-droplet contained in the microchannel,
        wherein the result comprises a temperature or a position of a micro-droplet;
    in response to each selected processing request, generating one or more control signals that, when applied to the microfluidic device, cause the device to perform the micro-droplet creation or the micro-droplet transformation specified by the processing request;
    for each sense signal provided for the at least one selected micro-droplet processing request, determining one or more of a position or a temperature of a micro-droplet, wherein selecting the micro-droplet processing request next after the at least one selected request is conditional upon the result of performing the at least one selected request, and
    repeating the selecting, the generating, and as applicable the determining, until the process is completed.

2. The method of claim 1 wherein the micro-droplet processing requests each specify one or more micro-droplet manipulations selected from the group consisting of: (i) creating at least one additional micro-droplet, (ii) moving at least one micro-droplet from a first position to a next position, (iii) combining at least two micro-droplets to form at least one additional micro-droplet, (iv) mixing or dissolving one or more reagents in at least one micro-droplet, (v) metering at least one micro-droplet from a fluid reservoir, (vi) sealing at least one micro-droplet at a position in the at least one microchannel, and (vii) stimulating a reaction in a micro-droplet trapped in the at least one microchannel.

3. The method of claim 2 wherein control signals generated in response to a request for moving a micro-droplet comprise signals for activating a controllable gas pressure generator.

4. The method of claim 2 wherein the moving at least one micro-droplet from a first position to a next position is such that the next position is selected from a plurality of possible next positions.

5. The method of claim 4 wherein, in response to a processing request specifying a move to a selected next position, control signals are generated either to cause obstruction of microchannels from the first position to all the plurality of possible next positions except the selected next position, or to open only a selected microchannel from a plurality of possible selected next positions.

6. The method of claim 5 wherein microchannels are either obstructed by a meltable material that is melted in response to at least one control signal, or are opened by withdrawing a meltable material in response to at least one control signal.

7. The method of claim 1 wherein the microfluidic device further comprises at least one heater for locally heating the microfluidic device, and wherein the control signals comprise signals for activating the heater.

8. The method of claim 1 wherein the process comprises a chemical process to be carried out in at least one micro-droplet.

9. The method of claim 8 wherein the control signals cause:
    formation of the at least one micro-droplet wherein the at least one micro-droplet has a composition suitable for the chemical process; and
    the chemical process to be carried out in the micro-droplet.

10. The method of claim 9 wherein the causing formation of the micro-droplet comprises combining a plurality of micro-droplets of reagents used in the chemical process.

11. The method of claim 9 wherein the causing the chemical process to be carried out in the micro-droplet further comprises:
(i) waiting for a time sufficient for occurrence of the process, or
(ii) exciting the micro-droplet.

12. The method of claim 11 wherein exciting the micro-droplet comprises applying heat or light thereto.

13. The method of claim 1 wherein the micro-droplet processing requests further comprise requests for creating a micro-droplet by contacting a gel, viscous liquid, semi-solid, or solid-form of a reagent with a liquid solvent so that the reagent disperses in the liquid.

14. The method of claim 13 wherein the solid-form disperses in the liquid by dissolving.

15. The method of claim 1, wherein the at least one resistive temperature detector is configured to sense a position of a micro-droplet by measuring a local specific heat.

16. The method of claim 1, wherein the at least one resistive temperature detector is configured with two pairs of control leads.

17. The method of claim 1, wherein the at least one resistive temperature detector is operatively coupled to a resistive heater.

18. The method of claim 1, wherein the microfluidic device further comprises a Peltier device.

19. The method of claim 1, wherein the microfluidic device further comprises a switching component.

20. A method for controlling a microfluidic device, the method comprising:
selecting a process from a plurality of predetermined processes,
wherein each predetermined process is associated with a group of micro-droplet processing requests for carrying out the predetermined process, and
wherein each micro-droplet processing request specifies the creation or transformation of at least one micro-droplet confined at least one microchannel in the microfluidic device,
selecting a micro-droplet processing request from the group of requests associated with the selected process,
wherein the microfluidic device comprises at least one resistive temperature detector which provides a sense signal indicative of a result of performing at least one selected micro-droplet processing request, wherein the result comprises a temperature or a position of a micro-droplet, and wherein the microfluidic device is configured to perform two or more different processes relating to the micro-droplet processing requests on the micro-droplet contained in the microchannel;
in response to each selected processing request, generating one or more control signals that, when applied to the microfluidic device, cause the device to perform the micro-droplet creation or the micro-droplet transformation specified by the selected processing request;
for each sense signal provided for the at least one selected micro-droplet processing request, determining one or more of a position or a temperature of a micro-droplet, wherein selecting the micro-droplet processing request next after the at least one selected request is conditional upon the result of performing the at least one selected request; and
repeating the selecting a processing request, the generating, and as applicable the determining, until the process is completed.

21. The method of claim 20 wherein the selecting a process further comprises:
displaying to a user indicia representing the predetermined processes available for selection; and
accepting user input representing selection of one of the predetermined processes, whereby the user-selected process is then performed by the microfluidic device.

22. The method of claim 20, further comprising:
displaying indicia representing one or more types of microfluidic devices capable of performing the micro-droplet processing requests in the group of processing requests associated with each process, and
requesting that a microfluidic device of one of the types be made available.

23. The method of claim 20, further comprising:
displaying indicia representing one or more types of reagent packs comprising aliquots of reagents used in the predetermined process,
wherein a reagent pack comprises at least one reservoir in fluid communication with at least one outlet port, wherein the reagent pack can be mated with the microfluidic device so that the outlet port is in fluid communication with an inlet port of the device, and whereby a reagent in the reservoir can be supplied to the microfluidic device, and
requesting that a reagent pack of one of the associated types be made available.

24. The method of claim 20, wherein the at least one resistive temperature detector is configured to sense a position of a micro-droplet by measuring a local specific heat.

25. The method of claim 20, wherein the at least one resistive temperature detector is configured with two pairs of control leads.

26. The method of claim 20, wherein the at least one resistive temperature detector is operatively coupled to a resistive heater.

27. The method of claim 20, wherein the microfluidic device further comprises a Peltier device.

28. The method of claim 20, wherein the microfluidic device further comprises a switching component.

* * * * *